United States Patent
Sohn et al.

(10) Patent No.: US 11,278,393 B2
(45) Date of Patent: *Mar. 22, 2022

(54) ACCOMMODATIVE INTRAOCULAR LENS

(71) Applicant: RAINBOW MEDICAL LTD., Herzliya (IL)

(72) Inventors: Zev Sohn, Ginot Shomron (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 99 days.

This patent is subject to a terminal disclaimer.

(21) Appl. No.: 16/841,037

(22) Filed: Apr. 6, 2020

(65) Prior Publication Data

US 2020/0253724 A1 Aug. 13, 2020

Related U.S. Application Data

(63) Continuation of application No. 15/896,340, filed on Feb. 14, 2018, now Pat. No. 10,646,330, which is a
(Continued)

(51) Int. Cl.
*A61F 2/16* (2006.01)

(52) U.S. Cl.
CPC .......... *A61F 2/1648* (2013.01); *A61F 2/1629* (2013.01); *A61F 2/1651* (2015.04);
(Continued)

(58) Field of Classification Search
CPC .... A61F 2/1624; A61F 2/1629; A61F 2/1648; A61F 2002/1682; A61F 2002/169; A61F 2002/16902
See application file for complete search history.

(56) References Cited

U.S. PATENT DOCUMENTS

| 4,704,125 A | 11/1987 | Ruminson |
| 4,711,638 A | 12/1987 | Lindstrom |

(Continued)

FOREIGN PATENT DOCUMENTS

| CN | 201015617 | 2/2008 |
| EP | 0337390 | 2/1993 |

(Continued)

OTHER PUBLICATIONS

Invitation to Pay Additional Fees dated Oct. 9, 2015, which issued during the prosecution of Applicant's PCT/IB2015/054730.
(Continued)

*Primary Examiner* — Leslie Lopez
(74) *Attorney, Agent, or Firm* — Sughrue Mion, PLLC

(57) ABSTRACT

An accommodating intraocular lens implant includes an anterior floating lens unit, a posterior lens unit, an anterior rim complex disposed such that the anterior floating lens unit is movable toward and away from the anterior rim complex. A plurality of levers are in jointed connection with: the anterior floating lens unit at respective first longitudinal sites along the levers, the anterior rim complex at respective second longitudinal sites along the levers, and the posterior lens unit at respective third longitudinal sites along the levers. The respective second longitudinal sites are longitudinally between the respective first and the respective third longitudinal sites. The levers are arranged (a) such that the third longitudinal sites serve as respective fulcrums for the plurality of levers, and (b) to move the anterior floating lens unit toward and away from the anterior rim complex, in the anterior-posterior direction. Other embodiments are also described.

12 Claims, 29 Drawing Sheets

Related U.S. Application Data continuation of application No. 14/315,301, filed on Jun. 25, 2014, now Pat. No. 9,925,039, which is a continuation-in-part of application No. 14/139,579, filed on Dec. 23, 2013, now abandoned.

(60) Provisional application No. 61/745,851, filed on Dec. 26, 2012.

(52) U.S. Cl.
CPC ............... *A61F 2002/1681* (2013.01); *A61F 2002/1682* (2015.04)

(56) References Cited

U.S. PATENT DOCUMENTS

| | | | |
|---|---|---|---|
| 4,778,463 A | 10/1988 | Hetland | |
| 4,863,465 A | 9/1989 | Kelman | |
| 4,950,289 A | 8/1990 | Krasner | |
| 5,275,623 A | 1/1994 | Sarfarazi | |
| 5,674,282 A | 10/1997 | Cumming | |
| 5,824,074 A | 10/1998 | Koch | |
| 5,968,094 A | 10/1999 | Werblin et al. | |
| 6,013,101 A | 1/2000 | Israel | |
| 6,117,171 A | 9/2000 | Skottun | |
| 6,231,603 B1 | 5/2001 | Lang et al. | |
| 6,423,094 B1 | 7/2002 | Sarfarazi | |
| 6,464,725 B2 | 10/2002 | Skottun | |
| 6,488,708 B2 | 12/2002 | Sarfarazi | |
| 6,524,340 B2 | 2/2003 | Israel | |
| 6,660,035 B1 | 12/2003 | Lang et al. | |
| 6,767,363 B1 | 7/2004 | Bandhauer et al. | |
| 6,884,263 B2 | 4/2005 | Valyunin et al. | |
| 7,223,288 B2 | 5/2007 | Zhang et al. | |
| 7,238,201 B2 | 7/2007 | Portney et al. | |
| 7,416,562 B2 | 8/2008 | Gross | |
| 7,871,437 B2 | 1/2011 | Hermans et al. | |
| 9,925,039 B2 | 3/2018 | Sohn et al. | |
| 10,646,330 B2 | 5/2020 | Sohn et al. | |
| 2002/0107568 A1 | 8/2002 | Zadno-Azizi et al. | |
| 2002/0111678 A1 | 8/2002 | Zadno-Azizi et al. | |
| 2003/0109925 A1 | 6/2003 | Ghazizadeh et al. | |
| 2003/0204255 A1 | 10/2003 | Peng et al. | |
| 2003/0204256 A1 | 10/2003 | Peng et al. | |
| 2004/0082993 A1 | 4/2004 | Woods | |
| 2004/0148023 A1 | 7/2004 | Shu | |
| 2005/0085907 A1* | 4/2005 | Hanna | A61F 2/1613 623/6.37 |
| 2006/0001186 A1 | 1/2006 | Richardson et al. | |
| 2007/0118216 A1 | 5/2007 | Pynson | |
| 2007/0156236 A1 | 7/2007 | Stenger | |
| 2008/0051886 A1 | 2/2008 | Lin | |
| 2008/0097461 A1 | 4/2008 | Boukhny et al. | |
| 2009/0030425 A1 | 1/2009 | Smiley et al. | |
| 2009/0204210 A1 | 8/2009 | Pynson | |
| 2009/0228101 A1 | 9/2009 | Zadno-Azizi | |
| 2011/0071628 A1* | 3/2011 | Gross | A61F 2/1629 623/6.51 |
| 2011/0295368 A1* | 12/2011 | Betser | A61F 2/1629 623/6.43 |
| 2013/0184816 A1 | 7/2013 | Hayes | |
| 2013/0197636 A1 | 8/2013 | Haefliger | |
| 2013/0304206 A1 | 11/2013 | Pallikaris et al. | |
| 2013/0317608 A1 | 11/2013 | Hermans et al. | |
| 2014/0052246 A1 | 2/2014 | Kahook et al. | |
| 2014/0180407 A1 | 6/2014 | Sohn et al. | |
| 2014/0309734 A1 | 10/2014 | Sohn et al. | |
| 2014/0309735 A1 | 10/2014 | Sohn et al. | |
| 2018/0221139 A1 | 8/2018 | Sohn et al. | |

FOREIGN PATENT DOCUMENTS

| | | |
|---|---|---|
| EP | 2364671 | 9/2011 |
| WO | 1999/03427 | 1/1999 |
| WO | 2009/021326 | 2/2009 |
| WO | 2009/021327 | 2/2009 |
| WO | 2010/089689 | 8/2010 |
| WO | 2013/016804 | 2/2013 |
| WO | 2013/126986 | 9/2013 |
| WO | 2015/198236 | 12/2015 |
| WO | 2016/161519 | 10/2016 |
| WO | 2017/181295 | 10/2017 |
| WO | 2017/208230 | 12/2017 |

OTHER PUBLICATIONS

International Search Report and Written Opinion in PCT/IB2015/054730, dated Dec. 28, 2015.
An Office Action dated Feb. 2, 2015, which issued during the prosecution of U.S. Appl. No. 14/139,579.
McLeod SD et al., "Synchrony dual-optic accomodating intraocular lens Part 1: Optical and biomechanical principles and design considerations," J Cataract Refract Surg. 2007; 33:37-46.
An Office Action dated Jan. 8, 2018, which issued during the prosecution of U.S. Appl. No. 15/170,417.
Ossma IL et al., "Synchrony Dual-Optic Accommodating Intraocular Lens Part 2: Pilot Clinical Evaluation," J Cataract Refract Surg. 2007; 33:47-52.
An Office Action dated Aug. 27, 2018, which issued during the prosecution of U.S. Appl. No. 15/393,947.
Crystalens 5.0 (Model AT-50SE), Mar. 2007.
Crystalens, Don't just see. See better, pp. 1-3, Sep. 2009.
U.S. Appl. No. 61/150,762, filed Feb. 8, 2009.
An International Search Report dated Jun. 18, 2010, which issued during the prosecution of Applicant's PCT/IB2010/050421.
StabilEyes® Capsular Tension Ring, Abbott Medical Optics, http://www.amo-inc.com/products/cataract/supportsystems/stabileyes-capsular-tension-ring, downloaded Mar. 9, 2014.
An Office Action dated Aug. 2, 2011, which issued during the prosecution of U.S. Appl. No. 12/566,029.
An Office Action dated Jan. 29, 2018, which issued during the prosecution of U.S. Appl. No. 15/125,916.
An Office Action dated Jan. 27, 2012, which issued during the prosecution of U.S. Appl. No. 12/566,029.
An International Search Report and a Written Opinion both dated Aug. 30, 2017, which issued during the prosecution of Applicant's PCT/IL2017/050594.
An Office Action dated May 26, 2016, which issued during the prosecution of U.S. Appl. No. 14/315,301.
An Office Action dated Oct. 30, 2015, which issued during the prosecution of U.S. Appl. No. 14/315,301.
European Search Report dated Jan. 4, 2018 which issued during the prosecution of Applicant's European App No. 15811584.0.
Still image excerpts from Modular IOL Video, ClarVista Medical, posted to YouTube.com on Dec. 5, 2013 (https://www.youtube.com/watch?v=-dAAPFHOqRQ).
TECNIS® 3-Piece IOL, Abbott Medical Optics, http://www.amo-inc.com/products/cataract/monofocal-iols/tecnisaspheric-iol, downloaded Mar. 9, 2014.
Krader CG, "Modular IOL system begins clinical evaluation," Ophthalmology Times, Jan. 2014.
An Interview Summary dated Jul. 6, 2017, which issued during the prosecution of U.S. Appl. No. 14/315,301.
An Interview Summary dated Jan. 10, 2017, which issued during the prosecution of U.S. Appl. No. 14/315,301.
An Office Action dated May 5, 2017, which issued during the prosecution of U.S. Appl. No. 14/315,301.
An Advisory Action dated Oct. 27, 2016, which issued during the prosecution of U.S. Appl. No. 14/315,301.
U.S. Appl. No. 61/745,851, filed Dec. 26, 2012.
An Office Action dated Nov. 16, 2018, which issued during the prosecution of U.S. Appl. No. 15/125,916.
An Office Action dated Aug. 7, 2018, which issued during the prosecution of U.S. Appl. No. 15/170,417.
An Office Action dated Jun. 28, 2018, which issued during the prosecution of U.S. Appl. No. 15/125,916.

(56) References Cited

OTHER PUBLICATIONS

An International Search Report and a Written Opinion both dated Feb. 26, 2018, which issued during the prosecution of Applicant's PCT/IL2017/051317.

An Office Action together with the English translation dated Oct. 29, 2019, which issued during the prosecution of Chinese Patent Application No. 201580043981.0.

An Office Action dated Apr. 18, 2019, which issued during the prosecution of U.S. Appl. No. 15/896,340.

An Office Action dated Oct. 30, 2019, which issued during the prosecution of U.S. Appl. No. 15/896,340.

An Office Action dated Apr. 17, 2019, which issued during the prosecution of U.S. Appl. No. 15/393,947.

* cited by examiner

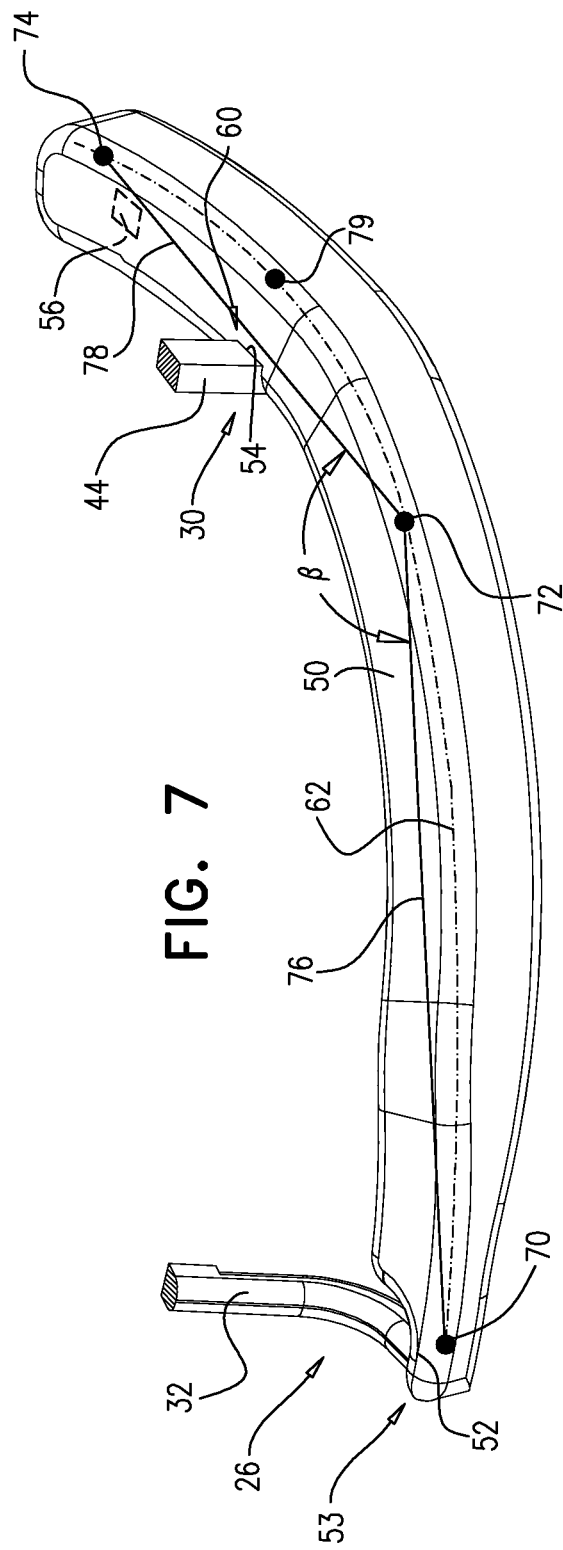

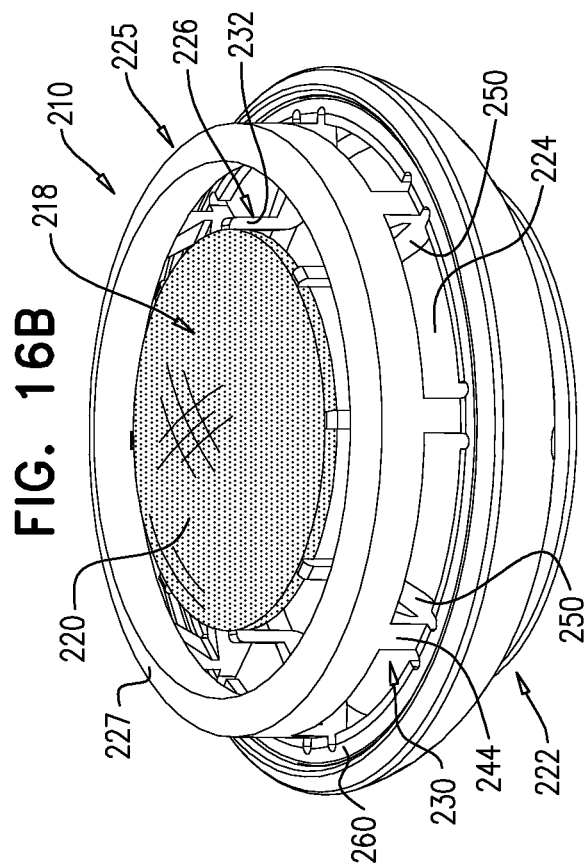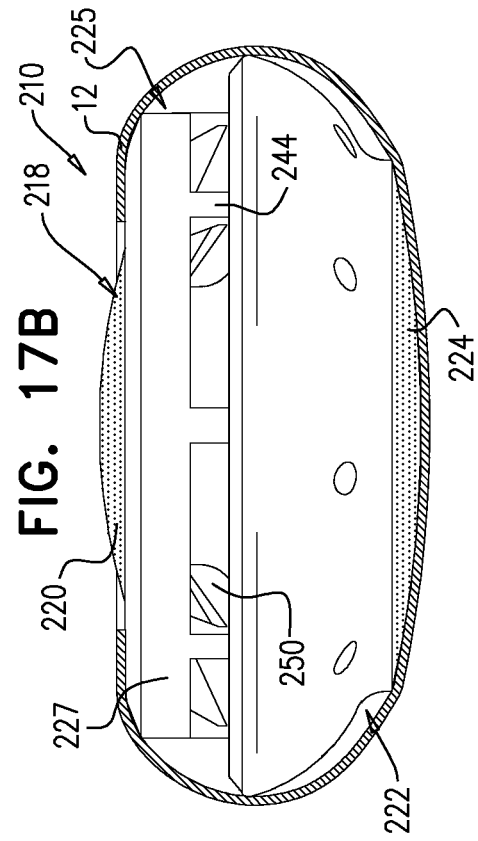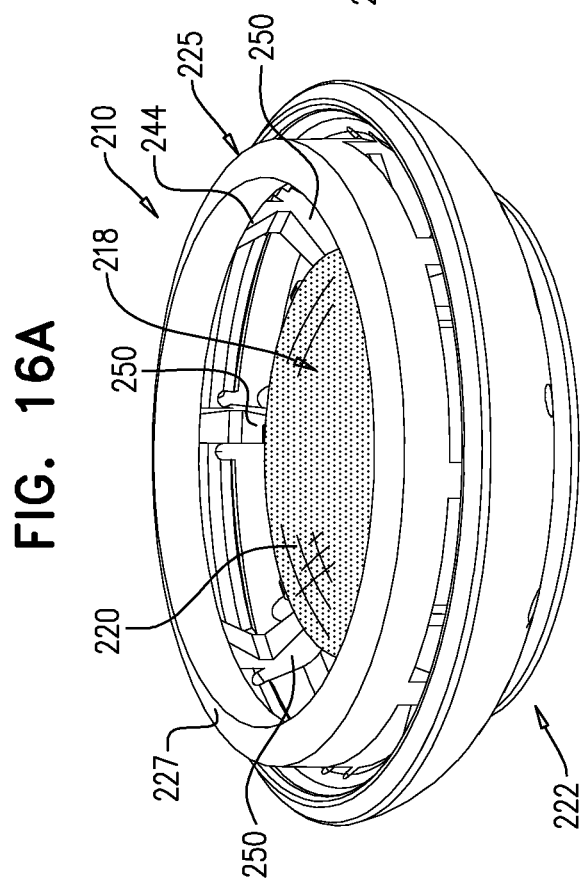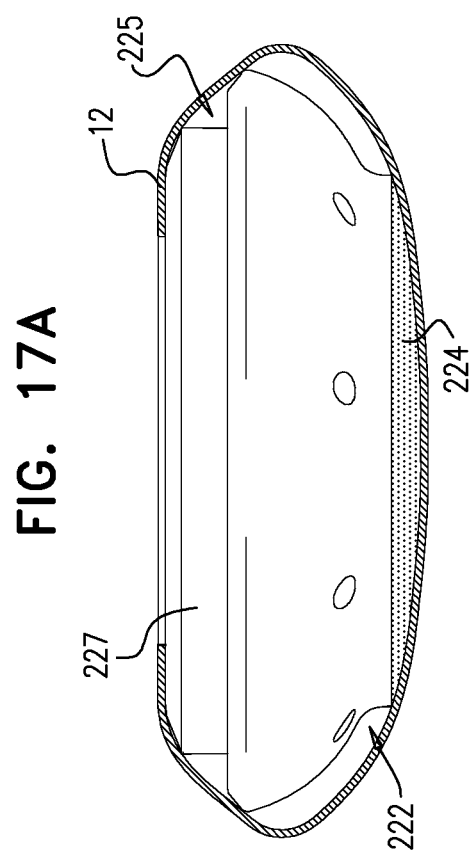

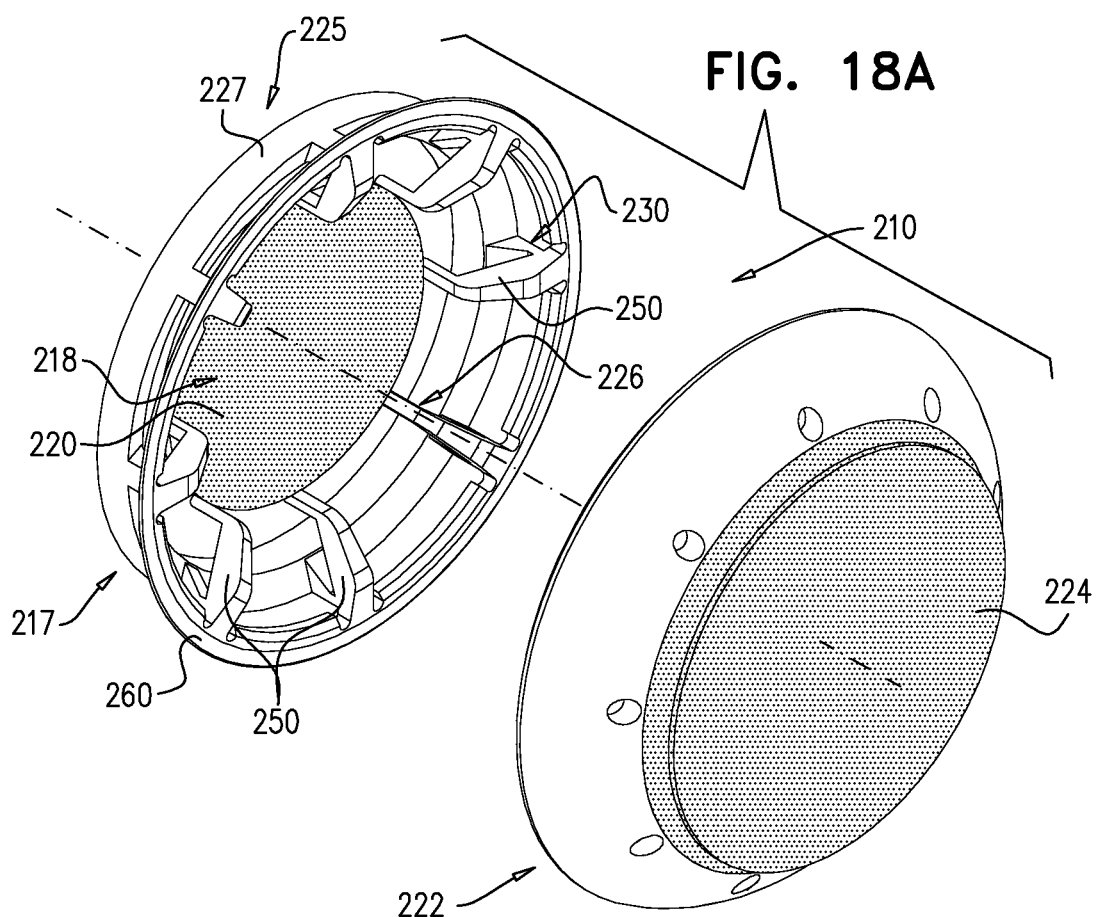
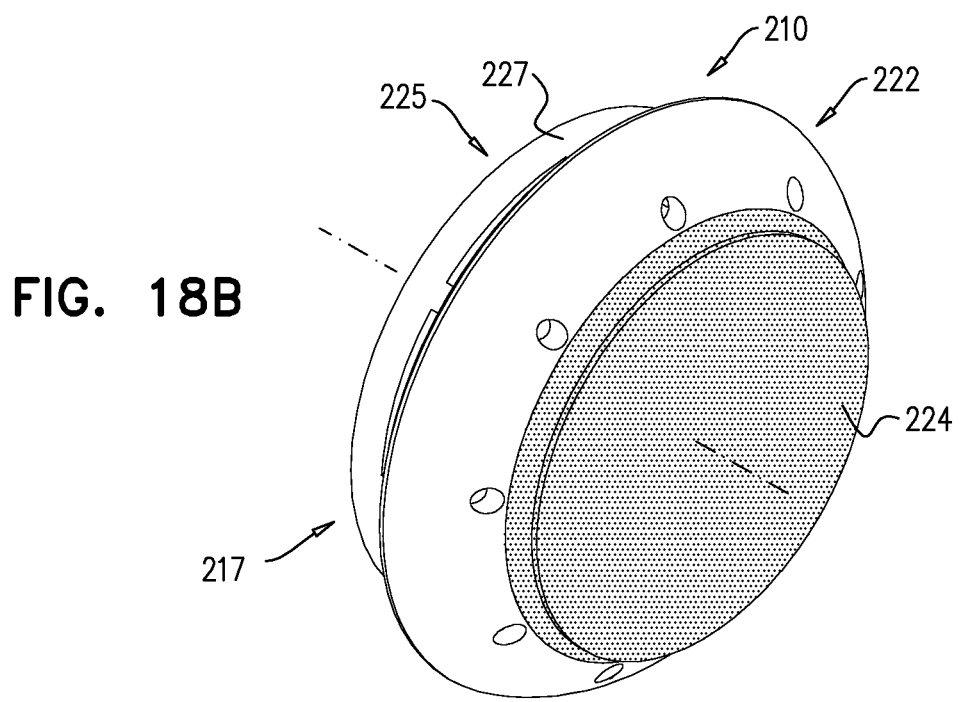

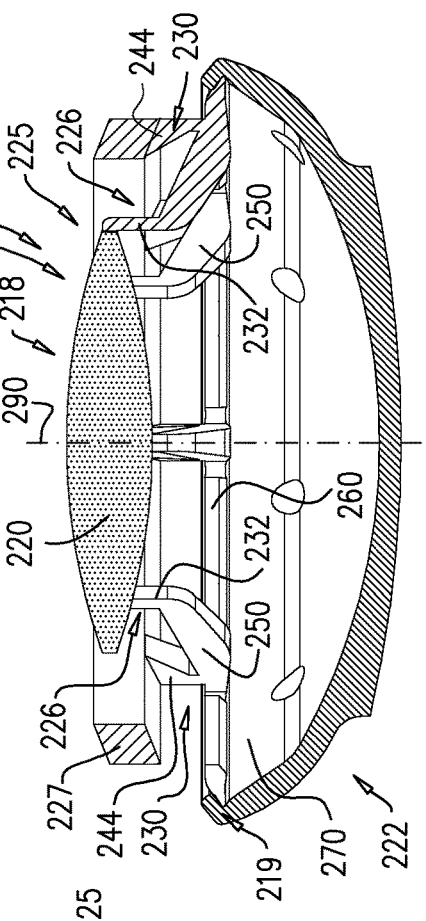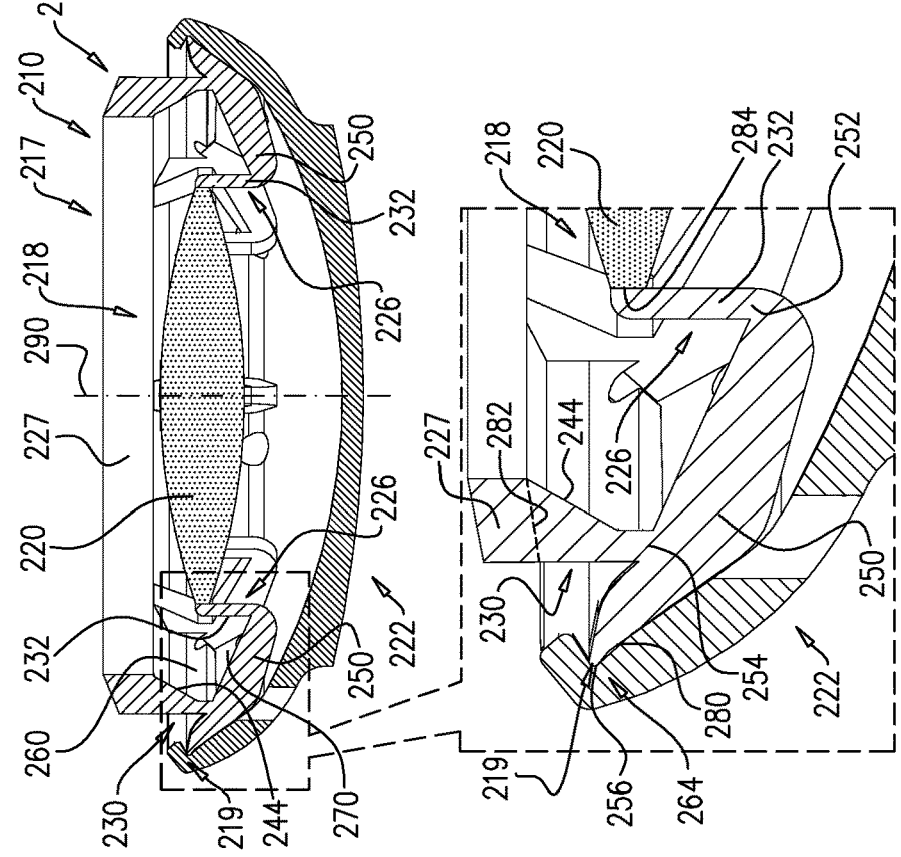

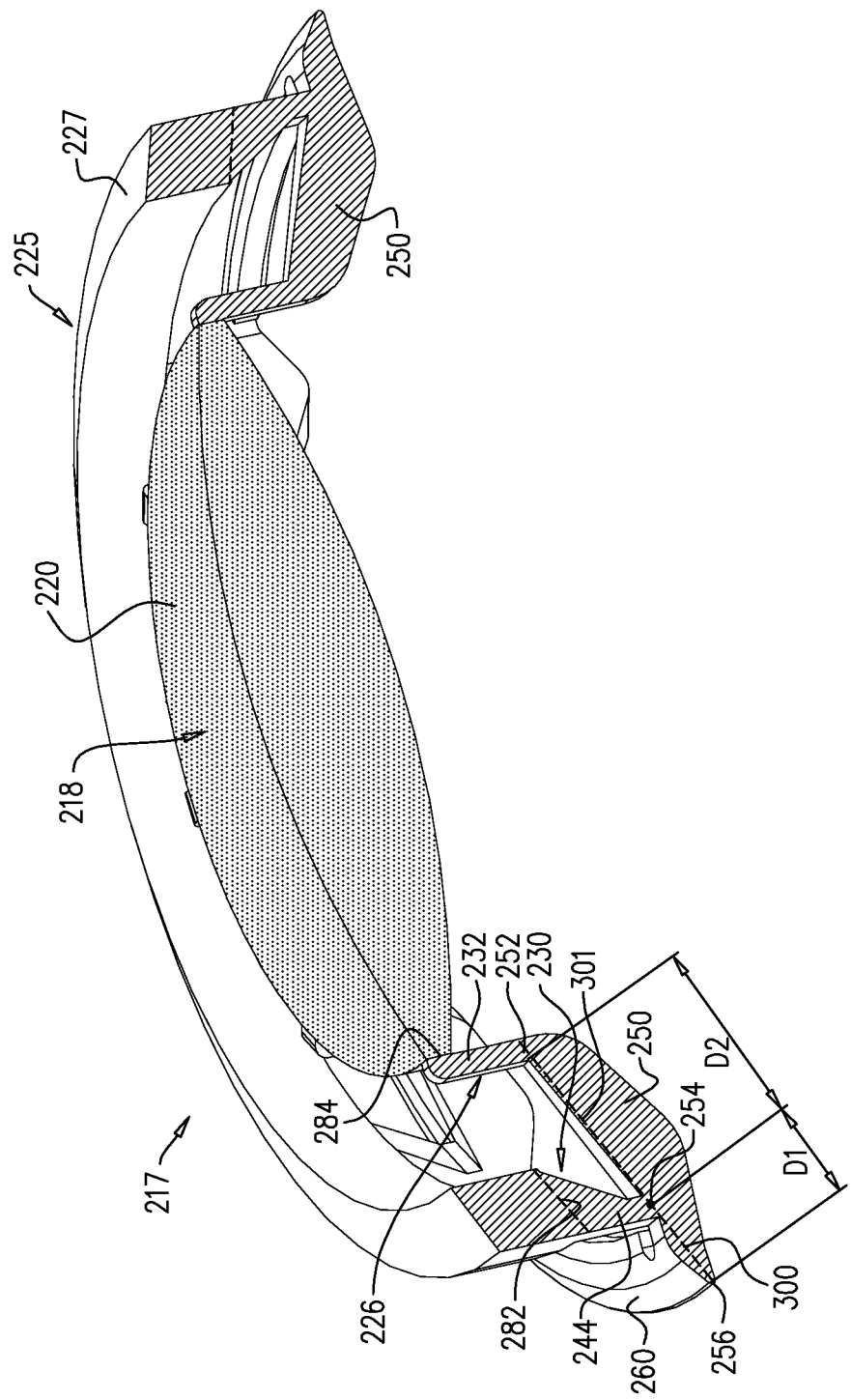

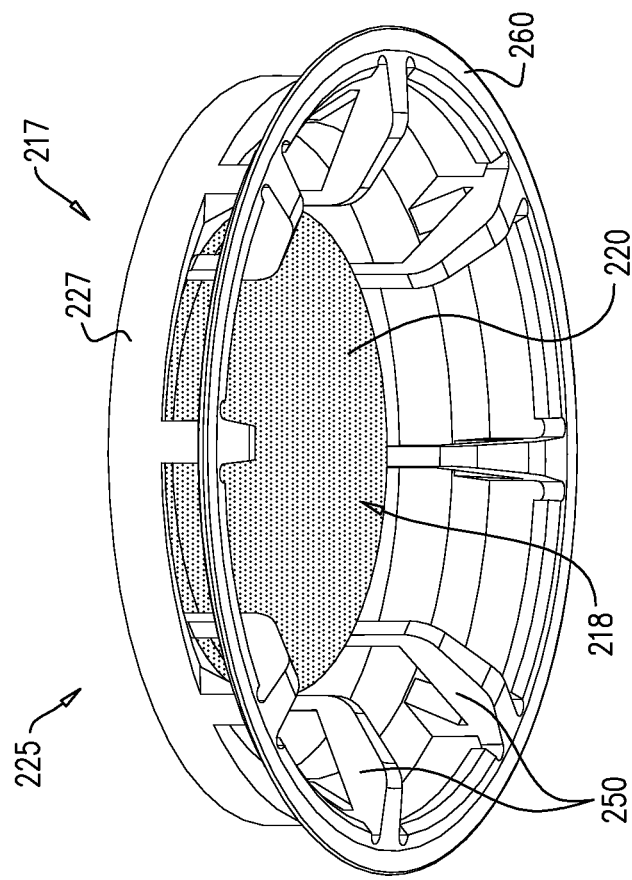
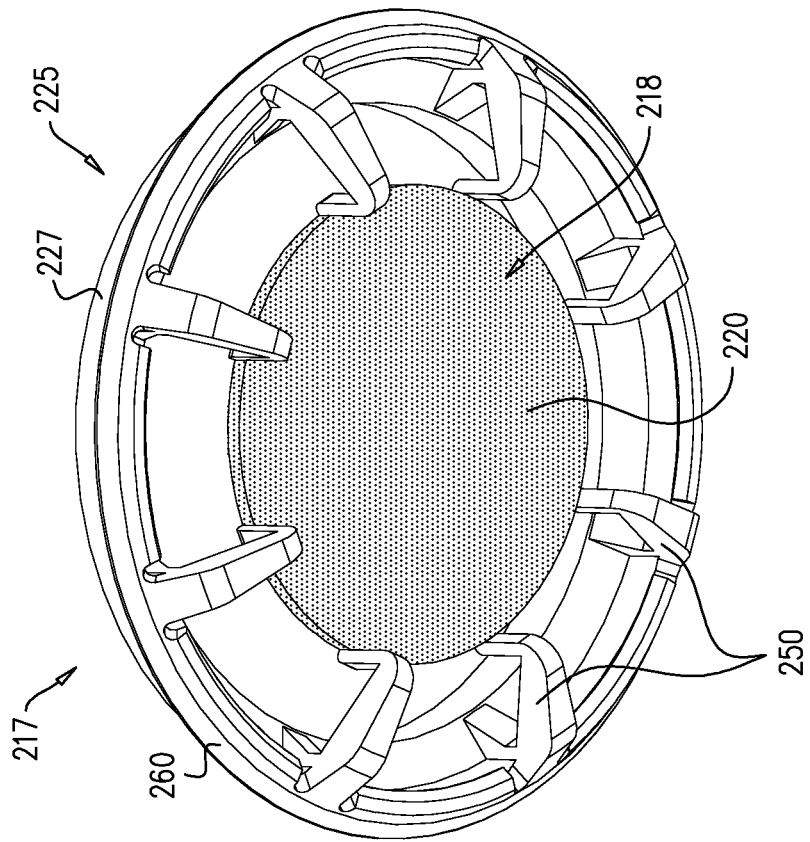

ACCOMMODATIVE INTRAOCULAR LENS

CROSS-REFERENCE TO RELATED APPLICATIONS

The present application is a continuation of U.S. application Ser. No. 15/896,340, filed Feb. 14, 2018, now U.S. Pat. No. 10,646,330, which is a continuation of U.S. application Ser. No. 14/315,301, filed Jun. 25, 2014, now U.S. Pat. No. 9,925,039, which is a continuation-in-part of U.S. application Ser. No. 14/139,579, filed Dec. 23, 2013, now abandoned, which claims the benefit of U.S. Provisional Application 61/745,851, filed Dec. 26, 2012, all of which applications are assigned to the assignee of the present application and are incorporated herein by reference.

FIELD OF THE APPLICATION

The present invention relates generally to implantable medical devices, and specifically to intraocular lenses.

BACKGROUND OF THE APPLICATION

Accommodating intraocular lenses (AIOLs) allow the eye to focus at different distances. The Crystalens® (Bausch & Lomb, Rochester, N.Y., USA) is an AIOL that has received FDA approval in the United States.

US Patent Application Publication 2011/0071628 to Gross et al. describes an accommodating intraocular lens (AIOL) implant that includes at least an anterior floating lens complex and a posterior lens complex, each of which comprises one or more optical elements, and a frame comprising one or more levers, which are coupled to the frame and the anterior floating lens complex. The levers are configured to leverage motion of the frame to move the anterior floating lens complex with respect to the posterior lens complex. Other embodiments are also described.

SUMMARY OF THE APPLICATION

In some applications of the present invention, an accommodative intraocular lens implant comprises an anterior floating lens unit and a posterior lens unit. The lens implant is configured such that the distance between the lens units (in the anterior-posterior direction) changes in response to the natural accommodation mechanism of the eye, thereby adjusting the focal length of the lens implant. The lens implant comprises one or more levers, which magnify the relatively small change in the width of the lens implant caused by the natural change in the shape of the natural capsular bag, in order to move the anterior floating lens unit a greater distance with respect to the posterior lens unit. Because of this distance magnification, the lens implant provides a high level of accommodation that mimics that of the natural eye.

The lens implant further comprises an anterior rim complex disposed such that the anterior floating lens unit is movable toward and away from the anterior rim complex, in the anterior-posterior direction. As the width (in the anterior-posterior direction) of the natural capsular bag changes, the anterior rim complex moves with respect to the posterior lens unit, thereby changing the distance therebetween. The levers are connected to the anterior floating lens unit, the anterior rim complex, and the posterior lens unit by respective links. The levers are configured to magnify the relatively small change in the distance between the anterior rim complex and the posterior lens unit, in order to move the anterior floating lens unit by a greater distance with respect to the posterior lens unit. The lens implant typically further comprises haptics, which provide a variable anterior-posterior distance between (a) an anterior ring of the anterior rim complex and (b) the posterior lens unit, and help position the lens implant properly in the capsular bag. Typically, the levers are not coupled to any of the haptics.

As mentioned above, the lens implant comprises a plurality of links. More particularly, the lens implant comprises:
  one or more anterior lens links, which comprise respective anterior lens jointed elements;
  one or more posterior lens links, which comprise respective posterior lens jointed elements; and
  one or more anterior rim links, which comprise respective anterior rim jointed elements.

Each of the levers of the lens implant is connected:
  at a first longitudinal site along the lever, to the anterior floating lens unit by one of the anterior lens links,
  at a second longitudinal site along the lever, to the anterior rim complex by one of the anterior rim links, and
  at a third longitudinal site along the lever, to the posterior lens unit by one of posterior lens links.

The second site of each lever is longitudinally between the first and third sites along the lever, such that the second site serves as a fulcrum for the lever. Typically, the fulcrum (the second site) is closer to the third site than to the first site. The lever is a first-class lever that pivots at the fulcrum. Because the fulcrum is closer to the third site than to the first site, the lever magnifies the anterior-posterior motion of the first site, resulting in greater anterior-posterior motion of the anterior floating lens unit. The lever is typically fairly stiff, such that it substantially does not change shape as it pivots during accommodation of the lens implant during normal implanted use.

Each of the jointed elements joins respective pairs of elements of the lens implant so as to permit relative motion (particularly rotational motion) between the joined elements. Typically, the posterior lens jointed elements and the anterior rim jointed elements are configured to minimize non-rotational motion, such as radial motion, between their respective joined elements to the extent possible given other design constraints, while still allowing a small amount of radial motion. The anterior lens jointed elements are typically configured to allow a small amount of radial motion between the lever and the anterior floating lens unit.

For some applications, each of the posterior lens links comprises exactly one posterior lens jointed element, each of the anterior rim links comprises exactly one anterior rim jointed element, and/or each of the anterior lens links comprises exactly one anterior lens jointed element. Typically, the anterior rim complex is not itself jointed, and/or the posterior lens unit is not itself jointed.

The arrangement of the levers and links provides stability to the lens implant, in combination with a high level of leverage for accommodation. In particular, in applications in which each of one or more of the links comprises exactly one jointed element, the arrangement reduces the number of degrees of freedom of motion of the components of the lens implant with respect to one another, thereby increasing stability of the lens implant. Stability is further increased in configurations in which the implant comprises at least three levers distributed around the circumference of the implant. Stability is still further increased by minimizing the number of links used to connect the anterior floating lens unit, the posterior lens unit, and the anterior rim complex, such as to one link per lever to each of these three elements.

The lens implant's accommodation typically provides a continuous range of focus, including near, distance, and intermediate distances. The lens implant exploits the natural accommodation mechanism of the eye, which reacts in order to sharpen the image on the retina. The lens implant thus typically reduces the need for glasses, which are generally required by patients with conventional IOLs. The lens implant is typically implanted in the eye after natural lens removal because of cataract, or for Refractive Lens Exchange (RLE), using well-known IOL implantation techniques, including making a small incision.

In some embodiments of the present invention, an accommodative intraocular lens implant comprises an anterior floating lens unit and a posterior lens unit. The lens implant is configured such that the distance between the lens units (in the anterior-posterior direction) changes in response to the natural accommodation mechanism of the eye, thereby adjusting the focal length of the lens implant. The lens implant comprises one or more levers, which magnify the relatively small change in the width of the lens implant caused by the natural change in the shape of the natural capsular bag, in order to move the anterior floating lens unit a greater distance with respect to the posterior lens unit. Because of this distance magnification, the lens implant provides a high level of accommodation that mimics that of the natural eye.

The lens implant further comprises an anterior rim complex disposed such that the anterior floating lens unit is movable toward and away from the anterior rim complex, in the anterior-posterior direction. The anterior rim complex comprises an anterior ring. As the width (in the anterior-posterior direction) of the capsular bag changes, the anterior rim complex moves with respect to the posterior lens unit, thereby changing the distance between the anterior rim complex and the posterior lens unit. The levers are connected to the anterior floating lens unit and the anterior rim complex, for example by respective anterior lens links and anterior rim links. The levers are also in jointed connection with the posterior lens unit. Typically, the lens implant comprises at least six levers (e.g., exactly six levers), such as more than six levers, e.g., at least eight levers (e.g., exactly eight levers), and, typically, a corresponding number of each of the anterior lens links and anterior rim links. For some applications, the levers are evenly circumferentially distributed around the lens implant. The levers are configured to magnify the relatively small change in the distance between the anterior rim complex and the posterior lens unit, in order to move the anterior floating lens unit by a greater distance with respect to the posterior lens unit. For some applications, the lens implant does not comprise any haptics. Alternatively, for some applications, the lens implant comprises haptics, which are not configured to transmit motion to the levers.

For some applications, the lens implant comprises two components that are initially separate from each other, and are typically assembled together in situ during implantation of the lens implant: (1) the posterior lens unit and (2) an anterior component. In this configuration, the posterior lens unit and the anterior component are distinct from each other and not permanently fixed to each other, and are shaped so as to be assemblable together in situ in a human eye. When assembled together, the posterior lens unit and the anterior component contact each other at one or more interfaces. Typically, when the posterior lens unit and the anterior component are assembled together, the levers are pivotable about the one or more interfaces.

For some applications, the lens implant (typically the anterior component thereof) further comprises a circumferential rim. The levers:
  at respective first longitudinal sites along the levers, are in jointed connection with the anterior floating lens unit, and
  at respective third longitudinal sites along the levers, are (a) fixed to the circumferential rim at respective, different circumferential locations around the rim, and (b) in jointed connection with the posterior lens unit.

For some applications, the anterior component comprises the following components:
  the anterior floating lens unit, which comprises an anterior lens;
  the anterior rim complex, which comprises the anterior ring;
  the levers;
  optionally, the anterior lens links; and
  optionally, the anterior rim links.

The levers are in jointed connection with:
  the anterior floating lens unit at the respective first longitudinal sites along the levers;
  the anterior rim complex at the respective second longitudinal sites along the levers; and
  the posterior lens unit at the respective third longitudinal sites along the levers.

For some applications, the lens implant comprises a plurality of anterior lens links, which typically comprise respective anterior lens jointed elements; and a plurality of anterior rim links, which typically comprise respective anterior rim jointed elements. For some applications, the levers are in the jointed connection:
  at the respective first longitudinal sites along the levers, with the anterior floating lens unit by the respective anterior lens links, and
  at the respective second longitudinal sites along the levers, with the anterior rim complex (typically with the anterior ring of the anterior rim complex) by the respective anterior rim links.

In addition, each of the levers, at a third longitudinal site along the lever, is in jointed connection with the posterior lens unit.

For each of the levers, the second longitudinal site is longitudinally between the first and third longitudinal sites along the lever, such that the third longitudinal site serves as a fulcrum for the lever. Typically, the second longitudinal sites are disposed radially inward from the third longitudinal sites, respectively. Typically, the first longitudinal sites are disposed radially inward from the second longitudinal sites and the third longitudinal sites, respectively.

Each of the jointed elements joins respective pairs of elements of the lens implant so as to permit relative motion (particularly rotational motion) between the joined elements. The anterior lens jointed elements are typically configured to allow a small amount of radial motion between the levers and the anterior floating lens unit. The anterior lens jointed elements are shaped and sized to rotate slightly to absorb this radial motion.

For some applications, the posterior lens unit is concave (e.g., bowl-shaped) and has an inner surface that defines an interface region, a portion of which defines a local maximum radius from a central optical axis of the posterior lens. Typically, the circumferential rim is in jointed connection with the interface region of the inner surface. For some applications, the posterior lens unit is shaped so as to define a lip anteriorly adjacent to the portion of the interface region. The lip is shaped so as to inhibit anterior motion of the circumferential rim. Typically, the inner surface slopes smoothly toward the interface region. For some applications, the lens implant is shaped such that the inner surface limits posterior motion of the anterior floating lens unit.

For some applications, for each of the levers, (a) a line defined by the second longitudinal site of the lever and the third longitudinal site of the lever, if projected onto a plane defined by a radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees, such as between 85 and 95 degrees, e.g., 90 degrees.

These embodiments allow for the use of a maximum number of levers and therefore provide more efficient use of the zonular tension that is circumferentially distributed around the lens capsule. These embodiments also provide a design with the shortest possible levers which contributes to easier folding and unfolding of the lens implant during insertion.

The lens implant's accommodation typically provides a continuous range of focus, including near, distance, and intermediate distances. The lens implant exploits the natural accommodation mechanism of the eye, which reacts in order to sharpen the image on the retina. The lens implant thus typically reduces the need for glasses, which are generally required by patients with conventional IOLs. The lens implant is typically implanted in the eye after natural lens removal because of cataract, or for Refractive Lens Exchange (RLE), using well-known IOL implantation techniques, including making a small incision.

There is therefore provided, in accordance with an application of the present invention, apparatus comprising an accommodating intraocular lens implant, which comprises:

an anterior floating lens unit, which comprises an anterior lens;

a posterior lens unit, which comprises a posterior lens;

an anterior rim complex disposed such that the anterior floating lens unit is movable toward and away from the anterior rim complex, in an anterior-posterior direction;

an anterior lens link, which comprises an anterior lens jointed element;

an anterior rim link, which comprises an anterior rim jointed element; and a lever, which is connected:
  at a first longitudinal site along the lever, to the anterior floating lens unit by the anterior lens link, and
  at a second longitudinal site along the lever, to the anterior rim complex by the anterior rim link,
wherein the lever, at a third longitudinal site along the lever, is in jointed connection with the posterior lens unit, and
wherein the second longitudinal site is longitudinally between the first and the third longitudinal sites along the lever.

For some applications, the lever is arranged such that the second longitudinal site serves as a fulcrum for the lever.

For some applications, the lens implant further comprises a posterior lens link, which comprises a posterior lens jointed element, and the lever, at the third longitudinal site, is in jointed connection with the posterior lens unit via the posterior lens link.

For some applications, the lever is arranged such that the third longitudinal site serves as a fulcrum for the lever.

For some applications, the lens implant comprises a plurality of levers, which (a) are in jointed connection with (i) the anterior floating lens unit at respective first longitudinal sites along the levers, (ii) the anterior rim complex at respective second longitudinal sites along the levers, and (iii) the posterior lens unit at respective third longitudinal site along the levers, and (b) are arranged to move the anterior floating lens unit toward and away from the anterior rim complex, in the anterior-posterior direction.

For some applications, for each of the levers, (a) a line defined by the second longitudinal site of the lever and the third longitudinal site of the lever, if projected onto a plane defined by the radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees.

For some applications, the second longitudinal sites are disposed radially inward from the third longitudinal sites, respectively. For some applications, the first longitudinal sites are disposed radially inward from the second longitudinal sites and the third longitudinal sites, respectively.

For some applications, for each of the levers, (a) a line defined by the first longitudinal site of the lever and the third longitudinal site of the lever, if projected onto the plane defined by the radially-outer perimeter of the lens implant, and (b) the line tangential to the radially-outer perimeter of the lens implant at the circumferential site of the perimeter circumferentially corresponding to the third longitudinal site of the lever, form an angle of between 75 and 105 degrees.

For some applications, the levers are evenly circumferentially distributed around the lens implant.

For some applications:
  the lens implant comprises an anterior component, which comprises the anterior floating lens unit, the anterior rim complex, and the lever,
  the posterior lens unit and the anterior component are distinct from each other and not permanently fixed to each other, and which are shaped so as to be assemblable together in situ in a human eye, and
  when the posterior lens unit and the anterior component are assembled together, the posterior lens unit and the anterior component contact each other at one or more interfaces.

For some applications, when the posterior lens unit and the anterior component are assembled together, the lever is pivotable about one of the one or more interfaces.

For some applications, the lens implant comprises six levers. Alternatively, for some applications, the lens implant comprises more than six levers.

For some applications, the lens implant comprises:
  a circumferential rim; and
  a plurality of levers, which (a) at respective first longitudinal sites along the levers, are in jointed connection with the anterior floating lens unit, and (b) at respective third longitudinal sites along the levers, are (i) fixed to the circumferential rim at respective, different circumferential locations around the rim, and (ii) in jointed connection with the posterior lens unit.

For some applications, the posterior lens unit is concave and has an inner surface that defines an interface region, a portion of which defines a local maximum radius from a central optical axis of the posterior lens, and the circumferential rim is in jointed connection with the interface region of the inner surface.

For some applications, the posterior lens unit is shaped so as to define a lip anteriorly adjacent to the portion of the interface region, which lip is shaped so as to inhibit anterior motion of the circumferential rim.

For some applications, the inner surface slopes smoothly toward the interface region.

For some applications, the circumferential rim has an outer radius that is greater than or equal to the local maximum radius of the inner surface of the posterior lens unit.

For some applications, the outer radius of the circumferential rim equals between 100% and 105% of the local maximum radius of the inner surface of the posterior lens unit.

For some applications, the third longitudinal site is at an end-most site of the lever.

For some applications, the second longitudinal site is closer to the third longitudinal site than to the first longitudinal site.

For some applications, a first distance between the second and the third longitudinal sites is at least 10% of a second distance between the first and the second longitudinal sites.

For some applications, a first distance between the second and the third longitudinal sites is less than 70% of a second distance between the first and the second longitudinal sites. For some applications, the first distance is less than 30% of the second distance.

For some applications, a straight line segment between the second longitudinal site and the third longitudinal site defines an angle of less than 15 degrees with a plane perpendicular to a central optical axis of the anterior lens at some point during a transition between fully-accommodated and fully-unaccommodated states of the lens implant. For some applications, the straight line segment is parallel to the plane at some point during the transition.

For some applications, a straight line segment between the second longitudinal site and the third longitudinal site rotates between 10 and 35 degrees as the lens implant transitions between fully-accommodated and fully-unaccommodated states.

For some applications, a straight line segment between the second longitudinal site and the first longitudinal site defines an angle of less than 15 degrees with a plane perpendicular to a central optical axis of the anterior lens at some point during a transition between fully-accommodated and fully-unaccommodated states of the lens implant. For some applications, the straight line segment is parallel to the plane at some point during the transition.

For some applications, a straight line segment between the second longitudinal site and the third longitudinal site defines an angle of less than 15 degrees with a plane perpendicular to a central optical axis of the anterior lens at a midpoint of rotation of the line segment as the lens implant transitions between fully-accommodated and fully-unaccommodated states. For some applications, the straight line segment is parallel to the plane at the midpoint of the rotation.

For some applications, a straight line segment between the second longitudinal site and the first longitudinal site defines an angle of less than 15 degrees with a plane perpendicular to a central optical axis of the anterior lens at a midpoint of rotation of the line segment as the lens implant transitions between fully-accommodated and fully-unaccommodated states. For some applications, the straight line segment is parallel to the plane at the midpoint of the rotation.

For some applications, a first straight line segment between the second longitudinal site and the third longitudinal site defines an angle of greater than 120 degrees with a second straight line segment between the second longitudinal site and the first longitudinal site. For some applications, the angle is greater than 150 degrees.

For some applications, a first distance between the second and the third longitudinal sites is at least 500 microns.

For some applications:
the posterior lens link is connected to the posterior lens unit at a posterior-lens-complex-connection site of the posterior lens unit,
the anterior rim link is connected to the anterior rim complex at an anterior-rim-complex-connection site of the anterior rim complex, and
the posterior-lens-complex-connection and the anterior-rim-complex-connection sites are circumferentially offset from each other with respect to a central optical axis of the anterior lens.

For some applications, the posterior-lens-complex-connection and the anterior-rim-complex-connection sites are circumferentially offset from each other by at least 15 degrees around the central optical axis. For some applications, posterior-lens-complex-connection and the anterior-rim-complex-connection sites are circumferentially offset from each other by less than 30 degrees around the central optical axis.

For some applications, the lens implant is configured such that a greatest change in distance between any portion of the lever and a central optical axis of the anterior lens is less than 500 microns as the lens implant transitions between fully-accommodated and fully-unaccommodated states.

For some applications, the lens implant is configured such that a greatest change in distance between any portion of the lever and a central optical axis of the anterior lens is less than 10% of a diameter of the anterior lens as the lens implant transitions between fully-accommodated and fully-unaccommodated states.

For some applications, the lens implant is configured such that a change in distance between the second longitudinal site and a central optical axis of the anterior lens is less than 500 microns as the lens implant transitions between fully-accommodated and fully-unaccommodated states.

For some applications, the lens implant is configured such that a change in distance between the third longitudinal site and a central optical axis of the anterior lens is less than 500 microns as the lens implant transitions between fully-accommodated and fully-unaccommodated states.

For some applications, the lens implant is configured such that, as the lens implant transitions between fully-accommodated and fully-unaccommodated states, (a) a change in distance between the second longitudinal site and a central optical axis of the anterior lens is less than 500 microns, and (b) a change in distance between the third longitudinal site and the central optical axis is less than 500 microns.

For some applications, the lens implant is configured such that a greatest change in distance between any portion of the posterior lens link and a central optical axis of the anterior lens is less than 500 microns as the lens implant transitions between fully-accommodated and fully-unaccommodated states.

For some applications, the posterior lens link comprises exactly one posterior lens jointed element. For some applications, the anterior rim link comprises exactly one anterior rim jointed element. For some applications, the anterior lens link comprises exactly one anterior lens jointed element.

For some applications, the anterior rim link comprises exactly one anterior rim jointed element.

For some applications, the anterior lens link comprises exactly one anterior lens jointed element.

For some applications, the anterior rim link is connected to the anterior rim complex at an anterior-rim-complex-connection site of the anterior rim complex, and a location of the second longitudinal site relative to the anterior rim complex changes by less than 500 microns as the lens implant transitions between fully-accommodated and fully-unaccommodated states. For some applications, the location of the second longitudinal site relative to the anterior rim complex changes by less than 200 microns as the lens implant transitions between the fully-accommodated and the fully-unaccommodated states.

For some applications, the anterior lens link is connected to the anterior floating lens unit at an anterior-lens-complex-connection site of the anterior floating lens unit, and a location of the first longitudinal site relative to the anterior floating lens unit changes by less than 500 microns as the lens implant transitions between fully-accommodated and fully-unaccommodated states.

For some applications, the location of the first longitudinal site relative to the anterior floating lens unit changes by less than 200 microns as the lens implant transitions between the fully-accommodated and the fully-unaccommodated states.

For some applications, the posterior lens link is connected to the posterior lens unit at a posterior-lens-complex-connection site of the posterior lens unit, and a location of the third longitudinal site relative to the posterior lens unit changes by less than 500 microns as the lens implant transitions between fully-accommodated and fully-unaccommodated states. For some applications, the location of the third longitudinal site relative to the posterior lens unit changes by less than 200 microns as the lens implant transitions between the fully-accommodated and the fully-unaccommodated states.

For some applications, a length of the anterior lens jointed element is less than 1000 microns. For some applications, the length of the anterior lens jointed element is less than 500 microns. For some applications, the length of the anterior lens jointed element is less than 300 microns.

For some applications, a length of the posterior lens jointed element is less than 1000 microns. For some applications, the length of the posterior lens jointed element is less than 500 microns. For some applications, the length of the posterior lens jointed element is less than 300 microns.

For some applications, a length of the anterior rim jointed element is less than 1000 microns. For some applications, the length of the anterior rim jointed element is less than 500 microns. For some applications, the length of the anterior rim jointed element is less than 300 microns.

For some applications, the lever, at each of all longitudinal locations therealong longitudinally between the first and the third longitudinal sites, is shaped so as to have a respective shape feature selected from the group of shape features consisting of: the lever is straight at the longitudinal location, the lever is curved at the longitudinal location, and the lever defines an angle of at least 120 degrees at the longitudinal location. For some applications, the lever, at each of the longitudinal locations at which the lever is curved, has a radius of curvature of at least 50% of a radius of the anterior lens.

For some applications, the anterior floating lens unit further comprises an attachment element, and the lever is connected to the attachment element by the anterior lens link. For some applications, the attachment element comprises an anterior lens post, and the lever is connected to the anterior lens post by the anterior lens link. For some applications, the attachment element comprises an anterior lens rim, and the lever is connected to the anterior lens rim by the anterior lens link.

For some applications, the anterior rim complex further comprises an attachment element, and the lever is connected to the attachment element by the anterior rim link. For some applications, the attachment element comprises an anterior post, and the lever is connected to the anterior post by the anterior rim link.

For some applications, the posterior lens unit further comprises an attachment element, and the lever is connected to the attachment element by the posterior lens link. For some applications, the attachment element comprises a posterior post, and the lever is connected to the posterior post by the posterior lens link. For some applications, the attachment element comprises a posterior lens rim, and the lever is connected to the posterior lens rim by the posterior lens link. For some applications, the attachment element further comprises a posterior post which is connected to the posterior lens rim, and the lever is connected to the posterior post by the posterior lens link.

For some applications, the anterior rim complex is not jointed.

For some applications, the posterior lens unit is not jointed.

For some applications, the lens implant is configured such that the lever moves the anterior floating lens unit by a first anterior-posterior distance with respect to the posterior lens unit when the anterior rim complex moves a second anterior-posterior distance with respect to the posterior lens unit, which first distance is greater than the second distance. For some applications, the first distance equals at least 1.5 times the second distance.

For some applications, the lens implant is configured such that the anterior rim complex rotates with respect to the posterior lens unit as the anterior floating lens unit moves toward and away from the anterior rim complex in the anterior-posterior direction.

For some applications, the anterior rim complex comprises an inner anterior ring, and the lever is connected at the second longitudinal site to the inner anterior ring by the anterior rim link.

For some applications, the anterior rim complex further comprises an outer anterior ring; the lens implant further comprises one or more haptics, which couple the outer anterior ring to the posterior lens unit, and provide a variable anterior-posterior distance between the outer anterior ring and the posterior lens unit; and the lever is not coupled to any of the haptics. For some applications, the inner anterior ring is shaped so as to define one or more anterior inner rim extensions which extend outwardly beyond the rest of the anterior inner rim, and are in contact with the outer anterior ring.

For some applications, the lens implant further comprises: (i) an outer anterior ring that is shaped so as to define a central opening generally concentric with the anterior lens; and (ii) one or more haptics, which are coupled to (a) the outer anterior ring at respective anterior coupling sites and (b) the posterior lens unit, and provide a variable anterior-posterior distance between the outer anterior ring and the posterior lens unit, and the outer anterior ring is shaped so as to define, in addition to central opening, one or more smaller openings disposed within 500 microns of the anterior coupling sites, respectively.

For some applications, the anterior lens, posterior lens, and anterior rim jointed elements comprise respective non-sliding joints.

For some applications, the anterior lens, posterior lens, and anterior rim jointed elements comprise respective rotating joints.

For some applications:
the anterior lens link is a first one of a plurality of anterior lens links, which further comprise a second anterior lens link, which comprises a second anterior lens jointed element;
the posterior lens link is a first one of a plurality of posterior lens links, which further comprise a second posterior lens link, which comprises a second posterior lens jointed element;
the anterior rim link is a first one of plurality of anterior rim links, which further comprise a second anterior rim link, which comprises a second anterior rim jointed element, and
the lever is a first one of plurality of levers, which further comprise a second lever, which is connected:
at a first longitudinal site along the second lever, to the anterior floating lens unit by the second anterior lens link,
at a second longitudinal site along the second lever, to the anterior rim complex by the second anterior rim link, and
at a third longitudinal site along the second lever, to the posterior lens unit by the second posterior lens link,
the second site is longitudinally between the first and the third sites along the second lever, such that the second site serves as a fulcrum for the second lever.

For some applications, the lens implant is configured such that a straight line segment between two points on a central longitudinal axis of the lever longitudinally at the first and the third sites, respectively, defines an angle with a plane perpendicular to a central optical axis of the anterior lens, which angle increases as the lens implant transitions from a fully-unaccommodated state to a fully-accommodated state.

For some applications, the lens implant is configured such that: when the lens implant is in a fully-unaccommodated state, the third longitudinal site along the lever is closer to the anterior rim complex than the first longitudinal site along the lever is to anterior rim complex: and when the lens implant is in a fully-accommodated state, the first longitudinal site is closer to the anterior rim complex 25 than the second longitudinal site is to the anterior rim complex.

For some applications, the lens implant is configured such that the anterior rim complex rotates with respect to the posterior lens unit as the anterior floating lens unit moves toward and away from the anterior rim complex in the anterior-posterior direction. For some applications, the lens implant is configured such that the anterior rim complex rotates with respect to the posterior lens unit by at least 1 degree around a central optical axis of the anterior lens as the lens implant transitions from a fully-unaccommodated state to a fully-accommodated state.

There is further provided, in accordance with an application of the present invention, apparatus comprising an accommodating intraocular lens implant, which comprises:
an anterior floating lens unit, which comprises an anterior lens;
a posterior lens unit, which comprises a posterior lens;
an anterior rim complex disposed such that the anterior floating lens unit is movable toward and away from the anterior rim complex, in an anterior-posterior direction; and
a lever, which is connected to the anterior floating lens unit, the anterior rim complex, and the posterior lens unit,
wherein the lens implant is configured such that a greatest change in distance between any portion of the lever and a central optical axis of the anterior lens is less than 10% of a diameter of the anterior lens as the lens implant transitions between fully-accommodated and fully-unaccommodated states.

For some applications, the lens implant is configured such that the greatest change in distance between any portion of the lever and the central optical axis is less than 5% of the diameter of the anterior lens as the lens implant transitions between the fully-accommodated and the fully-unaccommodated states For some applications, the lens implant is configured such that the greatest change in distance between any portion of the lever and the central optical axis is less than 500 microns as the lens implant transitions between the fully-accommodated and the fully-unaccommodated states. For some applications, the lens implant is configured such that the greatest change in distance between any portion of the lever and the central optical axis is less than 250 microns as the lens implant transitions between the fully-accommodated and the fully-unaccommodated states.

For some applications:
the lens implant further comprises:
an anterior lens link, which comprises an anterior lens jointed element;
a posterior lens link, which comprises a posterior lens jointed element; and
an anterior rim link, which comprises an anterior rim jointed element, the lever is connected:
at a first longitudinal site along the lever, to the anterior floating lens unit by the anterior lens link,
at a second longitudinal site along the lever, to the anterior rim complex by the anterior rim link, and
at a third longitudinal site along the lever, to the posterior lens unit by the posterior lens link, and
the second longitudinal site is longitudinally between the first and the third longitudinal sites along the lever, such that the second longitudinal site serves as a fulcrum for the lever.

For some applications, the lens implant is configured such that a change in distance between the second longitudinal site and the central optical axis is less than 500 microns as the lens implant transitions between the fully-accommodated and the fully-unaccommodated states.

For some applications, the lens implant is configured such that a change in distance between the second longitudinal site and the central optical axis is less than 250 microns as the lens implant transitions between the fully-accommodated and the fully-unaccommodated states.

For some applications, the lens implant is configured such that a change in distance between the second longitudinal site and the central optical axis is less than 10% of the diameter of the anterior lens as the lens implant transitions between the fully-accommodated and the fully-unaccommodated states.

For some applications, the lens implant is configured such that a change in distance between the third longitudinal site and the central optical axis is less than 500 microns as the lens implant transitions between the fully-accommodated and the fully-unaccommodated states.

For some applications, the lens implant is configured such that a change in distance between the third longitudinal site and the central optical axis is less than 250 microns as the lens implant transitions between the fully-accommodated and the fully-unaccommodated states.

For some applications, the lens implant is configured such that a change in distance between the third longitudinal site and the central optical axis is less than 10% of the diameter of the anterior lens as the lens implant transitions between the fully-accommodated and the fully-unaccommodated states.

For some applications, the lens implant is configured such that, as the lens implant transitions between the fully-accommodated and the fully-unaccommodated states, (a) a change in distance between the second longitudinal site and the central optical axis is less than 500 microns, and (b) a change in distance between the third longitudinal site and the central optical axis is less than 500 microns.

For some applications, the lens implant is configured such that a greatest change in distance between any portion of the posterior lens link and the central optical axis is less than 500 microns as the lens implant transitions between the fully-accommodated and the fully-unaccommodated states.

For some applications, the second longitudinal site is closer to the third longitudinal site than to the first longitudinal site.

There is still further provided, in accordance with an application of the present invention, a method comprising:
providing an accommodating intraocular lens implant, which includes:
an anterior floating lens unit, which includes an anterior lens;
a posterior lens unit, which includes a posterior lens;
an anterior rim complex disposed such that the anterior floating lens unit is movable toward and away from the anterior rim complex, in an anterior-posterior direction;
an anterior lens link, which includes an anterior lens jointed element;
an anterior rim link, which includes an anterior rim jointed element; and
a lever, which is connected:
at a first longitudinal site along the lever, to the anterior floating lens unit by the anterior lens link, and
at a second longitudinal site along the lever, to the anterior rim complex by the anterior rim link,
wherein the lever, at a third longitudinal site along the lever, is in jointed connection with the posterior lens unit, and
wherein the second longitudinal site is longitudinally between the first and the third longitudinal sites along the lever; and implanting the lens implant in a natural capsular bag of a patient.

There is additionally provided, in accordance with an application of the present invention, a method comprising:
providing an accommodating intraocular lens implant, which includes:
an anterior floating lens unit, which includes an anterior lens;
a posterior lens unit, which includes a posterior lens;
an anterior rim complex disposed such that the anterior floating lens unit is movable toward and away from the anterior rim complex, in an anterior-posterior direction; and
a lever, which is connected to the anterior floating lens unit, the anterior rim complex, and the posterior lens unit,
wherein the lens implant is configured such that a greatest change in distance between any portion of the lever and a central optical axis of the anterior lens is less than 10% of a diameter of the anterior lens as the lens implant transitions between fully-accommodated and fully-unaccommodated states; and
implanting the lens implant in a natural capsular bag of a patient.

There is yet additionally provided, in accordance with an application of the present invention, apparatus comprising an accommodating intraocular lens implant, which has a radially-outer perimeter and comprises:
an anterior floating lens unit, which comprises an anterior lens;
a posterior lens unit, which comprises a posterior lens;
an anterior rim complex; and
a plurality of levers, which (a) are in jointed connection with (i) the anterior floating lens unit at respective first longitudinal sites along the levers, (ii) the anterior rim complex at respective second longitudinal sites along the levers, and (iii) the posterior lens unit at respective third longitudinal sites along the levers, and (b) are arranged to move the anterior floating lens unit toward and away from the anterior rim complex, in an anterior-posterior direction,
wherein for each of the levers:
(a) a line defined by the second longitudinal site of the lever and the third longitudinal site of the lever, if projected onto a plane defined by the radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees, and
the second longitudinal site is longitudinally between the first and the third longitudinal sites along the lever, such that the third longitudinal site serves as a fulcrum for the lever.

For some applications, the angle is between 85 and 95 degrees.

For some applications, the angle equals 90 degrees.

For some applications, the radially-outer perimeter of the lens implant is defined by the posterior lens unit.

For some applications:
the lens implant further comprises:
a plurality of anterior lens links, which comprise respective anterior lens jointed elements; and
a plurality of anterior rim links, which comprise respective anterior rim jointed elements, and
the levers are in the jointed connection:
at the respective first longitudinal sites along the levers, with the anterior floating lens unit by the respective anterior lens links, and
at the respective second longitudinal sites along the levers, with the anterior rim complex by the respective anterior rim links.

For some applications, the levers are evenly circumferentially distributed around the lens implant.

For some applications, the third longitudinal sites are at respective end-most sites of the respective levers.

For some applications, the plurality of levers comprises at least six of the levers.

For some applications, each of the levers would not be curved if it were to be projected onto a plane defined by the radially-outer perimeter of the lens implant.

For some applications, the second longitudinal sites are disposed radially inward from the third longitudinal sites, respectively. For some applications, the first longitudinal sites are disposed radially inward from the second longitudinal sites and the third longitudinal sites, respectively.

For some applications, the lens implant is configured such that, for each of the levers, a greatest change in distance between any portion of the lever and a central optical axis of the anterior lens is less than 10% of a diameter of the anterior lens as the lens implant transitions between fully-accommodated and fully-unaccommodated states. For some applications, the lens implant is configured such that, for each of the levers, the greatest change in distance between any portion of the lever and the central optical axis of the anterior lens is less than 5% of the diameter of the anterior lens as the lens implant transitions between the fully-accommodated and the fully-unaccommodated states.

For some applications:

the lens implant comprises an anterior component, which comprises the anterior floating lens unit, the anterior rim complex, and the levers, the posterior lens unit and the anterior component are distinct from each other and not permanently fixed to each other, and which are shaped so as to be assemblable together in situ in a human eye, and when the posterior lens unit and the anterior component are assembled together, the posterior lens unit and the anterior component contact each other at one or more interfaces.

For some applications, when the posterior lens unit and the anterior component are assembled together, the levers are pivotable about the one or more interfaces.

For some applications, the lens implant further comprises a circumferential rim, to which the levers are fixed at respective, different circumferential locations around the rim, and the levers are in jointed connection with the posterior lens unit at the circumferential rim. For some applications, the posterior lens unit is concave and has an inner surface that defines an interface region, a portion of which defines a local maximum radius from a central optical axis of the posterior lens, and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

There is also provided, in accordance with an application of the present invention, apparatus comprising an accommodating intraocular lens implant, which comprises:

a posterior lens unit, which comprises a posterior lens; and an anterior component, which comprises (a) an anterior floating lens unit, which comprises an anterior lens, and (b) a plurality of levers, each of which is in jointed connection with the anterior floating lens unit, wherein the posterior lens unit and the anterior component are distinct from each other and not permanently fixed to each other, and which are shaped so as to be assemblable together in situ in a human eye, and wherein when the posterior lens unit and the anterior component are assembled together:

the posterior lens unit and the anterior component contact each other at one or more interfaces, and the levers are pivotable about the one or more interfaces, and are arranged to move the anterior floating lens unit toward and away from the posterior lens unit in an anterior-posterior direction.

For some applications, the lens implant further comprises a plurality of anterior lens links, which comprise respective anterior lens jointed elements, and the levers are in the jointed connection, at respective first longitudinal sites along the levers, with the anterior floating lens unit by the respective anterior lens links.

For some applications, the one or more interfaces comprise exactly one circumferential interface, and the posterior lens unit and the anterior component contact each other at the exactly one circumferential interface when the posterior lens unit and the anterior component are assembled together.

For some applications, the apparatus further comprises:

a first introducer tube, in which the posterior lens unit is removably disposed; and a second introducer tube, in which the anterior component is removably disposed, wherein the first and the second introducer tubes are distinct and separate from each other.

For some applications, the apparatus further comprises an introducer tube having a distal end, the posterior lens unit and the anterior component are in the introducer tube, and a distal-most portion of the anterior component is proximal to a proximal-most portion of the posterior lens unit.

For some applications, the plurality of levers comprises at least six of the levers.

For some applications, each of the levers is in jointed connection with the posterior lens unit at an end-most site of the lever, when the posterior lens unit and the anterior component are assembled together.

For some applications, the anterior component further comprises a circumferential rim, to which the levers are fixed at respective, different circumferential locations around the rim. For some applications, the circumferential rim of the anterior component contacts the posterior lens unit at the one or more interfaces when the posterior lens unit and the anterior component are assembled together. For some applications, the circumferential rim is pivotable about the one or more interfaces when the posterior lens unit and the anterior component are assembled together. For some applications, the one or more interfaces comprise exactly one circumferential interface, and the circumferential rim contacts the posterior lens unit at the exactly one circumferential interface when the posterior lens unit and the anterior component are assembled together. For some applications, the levers are in jointed connection with the posterior lens unit at the circumferential rim; the posterior lens unit is concave and has an inner surface that defines an interface region, a portion of which defines a local maximum radius from a central optical axis of the posterior lens; and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

For some applications, the anterior component further comprises an anterior rim complex, and each of levers is in jointed connection with the anterior floating lens unit and the anterior rim complex, and the levers are arranged to move the anterior floating lens unit toward and away from the anterior rim complex, in the anterior-posterior direction.

For some applications:
the anterior component further comprises:
a plurality of anterior lens links, which comprise respective anterior lens jointed elements; and a plurality of anterior rim links, which comprise respective anterior rim jointed elements, and
the levers are in the jointed connection:
at respective first longitudinal sites along the levers, with the anterior floating lens unit by the respective anterior lens links, and
at respective second longitudinal sites along the levers, with the anterior rim complex by the respective anterior rim links.

For some applications, when the posterior lens unit and the anterior component are assembled together:
the levers are in the jointed connection with (a) the anterior floating lens unit at respective first longitudinal sites along the levers, (ii) the anterior rim complex at respective second longitudinal sites along the levers, and (iii) the posterior lens unit at respective third longitudinal sites along the levers, and
for each of the levers, (a) a line defined by the second longitudinal site of the lever and the third longitudinal site of the lever, if projected onto a plane defined by a radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees.

For some applications, the second longitudinal sites are disposed radially inward from the third longitudinal sites, respectively. For some applications, the first longitudinal sites are disposed radially inward from the second longitudinal sites and the third longitudinal sites, respectively. For some applications, for each of the levers, (a) a line defined by the first longitudinal site of the lever and the third longitudinal site of the lever, if projected onto the plane defined by the radially-outer perimeter of the lens implant, and (b) the line tangential to the radially-outer perimeter of the lens implant at the circumferential site of the perimeter circumferentially corresponding to the third longitudinal site of the lever, form an angle of between 75 and 105 degrees. For some applications, the radially-outer perimeter of the lens implant is defined by the posterior lens unit. For some applications, the levers are evenly circumferentially distributed around the lens implant. For some applications, for each of the levers, the second longitudinal site is longitudinally between the first and the third longitudinal sites along the lever, such that the third longitudinal site serves as a fulcrum for the lever.

There is further provided, in accordance with an application of the present invention, apparatus comprising an accommodating intraocular lens implant, which comprises:
an anterior floating lens unit, which comprises an anterior lens;
a posterior lens unit, which comprises a posterior lens;
an anterior rim complex; and
six levers, each of which is in jointed connection with the anterior floating lens unit, the anterior rim complex, and the posterior lens unit, wherein the levers are arranged to move the anterior floating lens unit toward and away from the anterior rim complex, in an anterior-posterior direction.

For some applications, the lens implant comprises more than six of the levers.

For some applications,
the lens implant further comprises:
a plurality of anterior lens links, which comprise respective anterior lens jointed elements; and
a plurality of anterior rim links, which comprise respective anterior rim jointed elements, and
the levers are in the jointed connection:
at respective first longitudinal sites along the levers, with the anterior floating lens unit by the respective anterior lens links, and
at respective second longitudinal sites along the levers, with the anterior rim complex by the respective anterior rim links.

For some applications, each of the levers is in jointed connection with the posterior lens unit at an end-most site of the lever.

For some applications:
the levers are in jointed connection with (a) the anterior floating lens unit at respective first longitudinal sites along the levers, (b) the anterior rim complex at respective second longitudinal sites along the levers, and (c) the posterior lens unit at respective third longitudinal sites along the levers, and
for each of the levers, (a) a line defined by the second longitudinal site of the lever and the third longitudinal site of the lever, if projected onto a plane defined by a radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees.

For some applications, the second longitudinal sites are disposed radially inward from the third longitudinal sites, respectively. For some applications, the first longitudinal sites are disposed radially inward from the second longitudinal sites and the third longitudinal sites, respectively. For some applications, for each of the levers, (a) a line defined by the first longitudinal site of the lever and the third longitudinal site of the lever, if projected onto the plane defined by the radially-outer perimeter of the lens implant, and (b) the line tangential to the radially-outer perimeter of the lens implant at the circumferential site of the perimeter circumferentially corresponding to the third longitudinal site of the lever, form an angle of between 75 and 105 degrees. For some applications, the radially-outer perimeter of the lens implant is defined by the posterior lens unit. For some applications, the levers are evenly circumferentially distributed around the lens implant. For some applications, for each of the levers, the second longitudinal site is longitudinally between the first and the third longitudinal sites along the lever, such that the third longitudinal site serves as a fulcrum for the lever.

For some applications:
the lens implant comprises an anterior component, which comprises the anterior floating lens unit and the levers,
the posterior lens unit and the anterior component are distinct from each other and not permanently fixed to each other, and which are shaped so as to be assemblable together in situ in a human eye, and
when the posterior lens unit and the anterior component are assembled together, the posterior lens unit and the anterior component contact each other at one or more interfaces.

For some applications, when the posterior lens unit and the anterior component are assembled together, the levers are pivotable about the one or more interfaces.

For some applications, the lens implant further comprises a circumferential rim, to which the levers are fixed at respective, different circumferential locations around the rim; and the levers are in jointed connection with the posterior lens unit at the circumferential rim. For some applications, the posterior lens unit is concave and has an inner surface that defines an interface region, a portion of which defines a local maximum radius from a central optical axis of the posterior lens; and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

There is still further provided, in accordance with an application of the present invention, apparatus comprising an accommodating intraocular lens implant, which comprises:

a posterior lens unit, which comprises a posterior lens;

an anterior floating lens unit, which comprises an anterior lens; and a plurality of levers, each of which is in jointed connection with the anterior floating lens unit, wherein the levers are arranged to move the anterior floating lens unit toward and away from the posterior lens unit, in an anterior-posterior direction, wherein the lens implant is characterized by one of the group of characteristics consisting of:

the lens implant does not comprise any haptics, and the lens implant comprises haptics, which are not configured to transmit motion to the levers.

For some applications, the lens implant does not comprise any haptics.

For some applications, the lens implant further comprises a plurality of anterior lens links, which comprise respective anterior lens jointed elements; and the levers are in the jointed connection, at respective first longitudinal sites along the levers, with the anterior floating lens unit by the respective anterior lens links.

For some applications, the plurality of levers comprises at least six of the levers.

For some applications, each of the levers is in jointed connection with the posterior lens unit at an end-most site of the lever.

For some applications, the lens implant further comprises an anterior rim complex, and each of levers is in jointed connection with the anterior floating lens unit and the anterior rim complex, and the levers are arranged to move the anterior floating lens unit toward and away from the anterior rim complex, in the anterior-posterior direction. For some applications:

the lens implant further comprises:

a plurality of anterior lens links, which comprise respective anterior lens jointed elements; and a plurality of anterior rim links, which comprise respective anterior rim jointed elements, and the levers are in the jointed connection:

at respective first longitudinal sites along the levers, with the anterior floating lens unit by the respective anterior lens links, and at respective second longitudinal sites along the levers, with the anterior rim complex by the respective anterior rim links.

For some applications:

the levers are in jointed connection with (a) the anterior floating lens unit at respective first longitudinal sites along the levers, (ii) the anterior rim complex at respective second longitudinal sites along the levers, and (iii) the posterior lens unit at respective third longitudinal sites along the levers, and for each of the levers, (a) a line defined by the second longitudinal site of the lever and the third longitudinal site of the lever, if projected onto a plane defined by a radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees.

For some applications, the second longitudinal sites are disposed radially inward from the third longitudinal sites, respectively. For some applications, the first longitudinal sites are disposed radially inward from the second longitudinal sites and the third longitudinal sites, respectively. For some applications, for each of the levers, (a) a line defined by the first longitudinal site of the lever and the third longitudinal site of the lever, if projected onto the plane defined by the radially-outer perimeter of the lens implant, and (b) the line tangential to the radially-outer perimeter of the lens implant at the circumferential site of the perimeter circumferentially corresponding to the third longitudinal site of the lever, form an angle of between 75 and 105 degrees. For some applications, the radially-outer perimeter of the lens implant is defined by the posterior lens unit. For some applications, the levers are evenly circumferentially distributed around the lens implant. For some applications, for each of the levers, the second longitudinal site is longitudinally between the first and the third longitudinal sites along the lever, such that the third longitudinal site serves as a fulcrum for the lever.

For some applications:

the lens implant comprises an anterior component, which comprises the anterior floating lens unit and the levers, the posterior lens unit and the anterior component are distinct from each other and not permanently fixed to each other, and which are shaped so as to be assemblable together in situ in a human eye, and when the posterior lens unit and the anterior component are assembled together, the posterior lens unit and the anterior component contact each other at one or more interfaces.

For some applications, when the posterior lens unit and the anterior component are assembled together, the levers are pivotable about the one or more interfaces.

For some applications, the lens implant further comprises a circumferential rim, to which the levers are fixed at respective, different circumferential locations around the rim; and the levers are in jointed connection with the posterior lens unit at the circumferential rim. For some applications, the posterior lens unit is concave and has an inner surface that defines an interface region, a portion of which defines a local maximum radius from a central optical axis of the posterior lens; and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

For some applications, the lens implant comprises haptics, which are not configured to transmit motion to the levers. For some applications, the levers are indirectly connected to the haptics by one or more other elements of the lens implant.

There is additionally provided, in accordance with an application of the present invention, apparatus comprising:
an accommodating intraocular lens implant, which comprises an anterior component, which comprises:
   an anterior floating lens unit, which (a) comprises an anterior lens and a circumferential rim that radially surrounds the anterior lens, and (b) has a central longitudinal axis that intersects a radial center of the anterior lens and is perpendicular to a plane defined by the circumferential rim; and
   a plurality of levers, which are (a) fixed to the circumferential rim at respective circumferential sites, and (b) in jointed connection with the anterior floating lens unit; and
an introducer tube, in which the anterior component is removably disposed while folded or rolled about a line that (a) intersects (i) the central longitudinal axis and (ii) a point on the circumferential rim that is circumferentially between two circumferentially-adjacent ones of the circumferential sites, and (b) is parallel to the plane defined by the circumferential rim.

For some applications, the point is circumferentially offset from each of the two circumferentially-adjacent circumferential sites by at least 18 degrees.

For some applications, the point on the circumferential rim is circumferentially offset from each of the two circumferentially-adjacent circumferential sites by 40% to 60% of a circumferential offset between the two circumferentially-adjacent circumferential sites.

For some applications, the anterior component further comprises a plurality of anterior lens links, which comprise respective anterior lens jointed elements; and the levers are in the jointed connection, at respective first longitudinal sites along the levers, with the anterior floating lens unit by the respective anterior lens links.

For some applications, the plurality of levers comprises at least six of the levers.

For some applications, the lens implant further comprises a posterior lens unit, which is distinct from and not permanently fixed to the anterior component, the posterior lens unit and the anterior component are shaped so as to be assemblable together in situ in a human eye; the posterior lens unit comprises a posterior lens; and when the posterior lens unit and the anterior component are assembled together, the posterior lens unit and the anterior component contact each other at one or more interfaces. For some applications, when the posterior lens unit and the anterior component are assembled together, the levers are pivotable about the one or more interfaces, and are arranged to move the anterior floating lens unit toward and away from the posterior lens unit in an anterior-posterior direction. For some applications, the introducer tube is an anterior-component introducer tube; the apparatus further comprises a posterior-lens-unit introducer tube, in which the posterior lens unit is removably disposed; and the anterior-component and the posterior-lens-unit introducer tube are distinct and separate from each other. For some applications, the introducer tube has a distal end, and the posterior lens unit and the anterior component are in the introducer tube, and a distal-most portion of the anterior component is proximal to a proximal-most portion of the posterior lens unit.

For some applications, the lens implant further comprises a circumferential rim, to which the levers are fixed at respective, different circumferential locations around the rim; and the levers are in jointed connection with the posterior lens unit at the circumferential rim.

For some applications, the posterior lens unit is concave and has an inner surface that defines an interface region, a portion of which defines a local maximum radius from a central optical axis of the posterior lens; and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

For some applications, the anterior component further comprises an anterior rim complex, and each of levers is in jointed connection with the anterior floating lens unit and the anterior rim complex, and the levers are arranged to move the anterior floating lens unit toward and away from the anterior rim complex, in the anterior-posterior direction, when the anterior component is not disposed in the introducer tube.

For some applications:
the lens implant further comprises:
a plurality of anterior lens links, which comprise respective anterior lens jointed elements; and
a plurality of anterior rim links, which comprise respective anterior rim jointed elements, and
the levers are in the jointed connection:
at respective first longitudinal sites along the levers, with the anterior floating lens unit by the respective anterior lens links, and
at respective second longitudinal sites along the levers, with the anterior rim complex by the respective anterior rim links.

There is yet additionally provided, in accordance with an application of the present invention, apparatus comprising an accommodating intraocular lens implant, which comprises:
a concave posterior lens unit, which comprises a posterior lens, and has an inner surface;
an anterior floating lens unit, which comprises an anterior lens;
a plurality of levers, which (a) are in jointed connection with the anterior floating lens unit and the posterior lens unit, and (b) are arranged to move the anterior floating lens unit toward and away from the posterior lens unit, in an anterior-posterior direction, the lens implant is shaped such that the inner surface limits posterior motion of the anterior floating lens unit.

For some applications, the levers and the inner surface of the posterior lens unit are shaped such that the inner surface limits the posterior motion of the anterior floating lens unit by the inner surface touching the levers.

For some applications, the plurality of levers comprises at least six of the levers.

For some applications, each of the levers is in jointed connection with the posterior lens unit at an end-most site of the lever.

For some applications, the anterior component further comprises a plurality of anterior lens links, which comprise respective anterior lens jointed elements; and the levers are in the jointed connection, at respective first longitudinal sites along the levers, with the anterior floating lens unit by the respective anterior lens links.

For some applications, the anterior component further comprises an anterior rim complex disposed such that the anterior floating lens unit is movable toward and away from the anterior rim complex, in the anterior-posterior direction; and each of levers is in jointed connection with the floating lens unit, the anterior rim complex, and the posterior lens unit.

For some applications:
the lens implant further comprises:
a plurality of anterior lens links, which comprise respective anterior lens jointed elements; and
a plurality of anterior rim links, which comprise respective anterior rim jointed elements, and
the levers are in the jointed connection:
at respective first longitudinal sites along the levers, with the anterior floating lens unit by the respective anterior lens links, and
at respective second longitudinal sites along the levers, with the anterior rim complex by the respective anterior rim links.

For some applications:
the levers are in the jointed connection with (a) the anterior floating lens unit at respective first longitudinal sites along the levers, (ii) the anterior rim complex at respective second longitudinal sites along the levers, and (iii) the posterior lens unit at respective third longitudinal sites along the levers, and
for each of the levers, (a) a line defined by the second longitudinal site of the lever and the third longitudinal site of the lever, if projected onto a plane defined by a radially-outer perimeter of the lens implant, and (b) a line tangential to the radially-outer perimeter of the lens implant at a circumferential site of the perimeter circumferentially corresponding to the third longitudinal site of the lever, form an angle of between 75 and 105 degrees.

For some applications, the second longitudinal sites are disposed radially inward from the third longitudinal sites, respectively. For some applications, the first longitudinal sites are disposed radially inward from the second longitudinal sites and the third longitudinal sites, respectively. For some applications, for each of the levers, (a) a line defined by the first longitudinal site of the lever and the third longitudinal site of the lever, if projected onto the plane defined by the radially-outer perimeter of the lens implant, and (b) the line tangential to the radially-outer perimeter of the lens implant at the circumferential site of the perimeter circumferentially corresponding to the third longitudinal site of the lever, form an angle of between 75 and 105 degrees. For some applications, the radially-outer perimeter of the lens implant is defined by the posterior lens unit. For some applications, the levers are evenly circumferentially distributed around the lens implant. For some applications, for each of the levers, the second longitudinal site is longitudinally between the first and the third longitudinal sites along the lever, such that the third longitudinal site serves as a fulcrum for the lever.

For some applications:
the lens implant comprises an anterior component, which comprises the anterior floating lens unit and the levers,
the posterior lens unit and the anterior component are distinct from each other and not permanently fixed to each other, and which are shaped so as to be assemblable together in situ in a human eye, and
when the posterior lens unit and the anterior component are assembled together, the posterior lens unit and the anterior component contact each other at one or more interfaces.

For some applications, when the posterior lens unit and the anterior component are assembled together, the levers are pivotable about the one or more interfaces.

For some applications, the lens implant further comprises a circumferential rim, to which the levers are fixed at respective, different circumferential locations around the rim; and the levers are in jointed connection with the posterior lens unit at the circumferential rim. For some applications, the posterior lens unit is concave and has an inner surface that defines an interface region, a portion of which defines a local maximum radius from a central optical axis of the posterior lens; and the circumferential rim is in jointed connection with the interface region of the inner surface. For some applications, the posterior lens unit is shaped so as to define a lip anteriorly adjacent to the portion of the interface region, which lip is shaped so as to inhibit anterior motion of the circumferential rim. For some applications, the inner surface slopes smoothly toward the interface region. For some applications, the circumferential rim has an outer radius that is greater than or equal to the local maximum radius of the inner surface of the posterior lens unit. For some applications, the outer radius of the circumferential rim equals between 100% and 105% of the local maximum radius of the inner surface of the posterior lens unit.

There is also provided, in accordance with an application of the present invention, apparatus comprising an accommodating intraocular lens implant, which has a radially-outer perimeter and comprises:
an anterior floating lens unit, which comprises an anterior lens;
a posterior lens unit, which comprises a posterior lens;
an anterior rim complex; and
a plurality of levers, each of which in jointed connection with the anterior floating lens unit, the anterior rim complex, and the posterior lens unit, wherein the levers are arranged to move the anterior floating lens unit toward and away from the anterior rim complex, in an anterior-posterior direction,
wherein each of the levers would not be curved if it were to be projected onto a plane defined by the radially-outer perimeter of the lens implant.

There is further provided, in accordance with an application of the present invention, apparatus comprising an accommodating intraocular lens implant, which comprises:
an anterior floating lens unit, which comprises an anterior lens;
a posterior lens unit, which comprises a posterior lens;
an anterior rim complex disposed such that the anterior floating lens unit is movable toward and away from the anterior rim complex, in an anterior-posterior direction; and a plurality of levers, each of which in jointed connection with the anterior floating lens unit, the anterior rim complex, and the posterior lens unit, wherein the levers are arranged to move the anterior floating lens unit toward and away from the anterior rim complex, in an anterior-posterior direction, wherein the lens implant is configured such that a greatest possible anterior-posterior stroke distance of the anterior rim complex is at least 0.875 mm.

For some applications, the lens implant is configured such that the greatest possible anterior-posterior stroke distance of the anterior rim complex is at least 1.05 mm.

The present invention will be more fully understood from the following detailed description of embodiments thereof, taken together with the drawings, in which:

BRIEF DESCRIPTION OF THE DRAWINGS

FIG. 7 is a schematic view of a lever of the lens implant of FIGS. 1A-3B, in accordance with an application of the present invention;

FIGS. 16A-B are isometric schematic illustrations of yet another accommodative intraocular lens implant, in fully-unaccommodated and fully-accommodated states, respectively, in accordance with an application of the present invention;

FIGS. 17A-B are side views of the lens implant of FIGS. 16A-B, showing the lens implant implanted in a natural capsular bag of the eye, in fully-unaccommodated and fully-accommodated states, respectively, in accordance with an application of the present invention;

FIGS. 18A and 18B are schematic illustrations of a two-part assembly configuration of the lens implant of FIGS. 16A-B, in disassembled and assembled states, respectively, in accordance with an application of the present invention;

FIGS. 19A-B are schematic cross-sectional illustrations of the lens implant of FIGS. 16A-B in the fully-unaccommodated state and fully-accommodated state, respectively, in accordance with an application of the present invention:

FIGS. 21A-C are schematic illustrations of an anterior component of the lens implant of FIGS. 16A-B in the fully-accommodated state, in accordance with an application of the present invention;

FIGS. 23A-B provide an additional view of an anterior component of the lens implant of FIGS. 16A-B, in the fully-unaccommodated and the fully-accommodated states, respectively, in accordance with an application of the present invention;

DETAILED DESCRIPTION OF APPLICATIONS

Figure 1A:
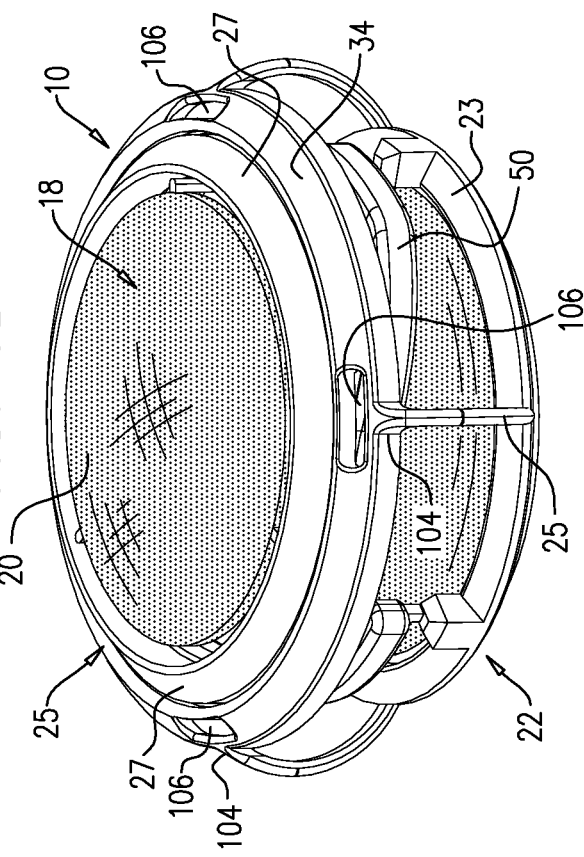
FIGS. 1A-B are schematic isometric illustrations of an accommodative intraocular lens implant, in fully-unaccommodated and fully-accommodated states, respectively, in accordance with an application of the present invention.
Figure 1B:
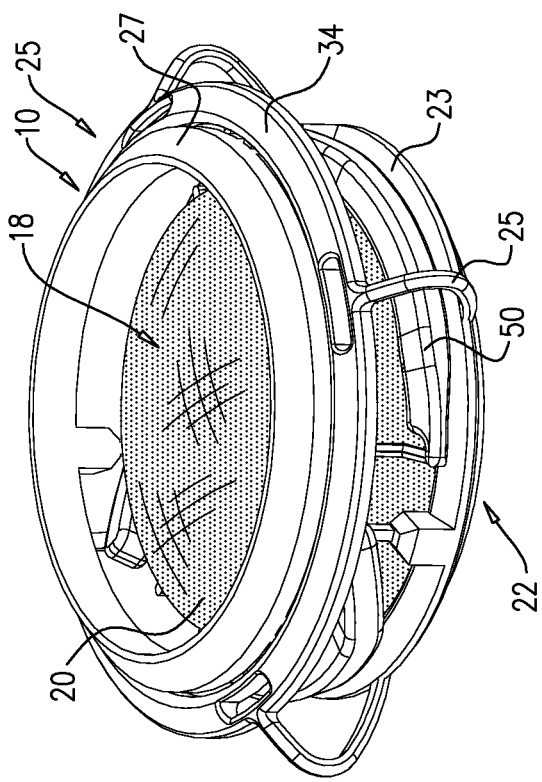
Figure 2A:
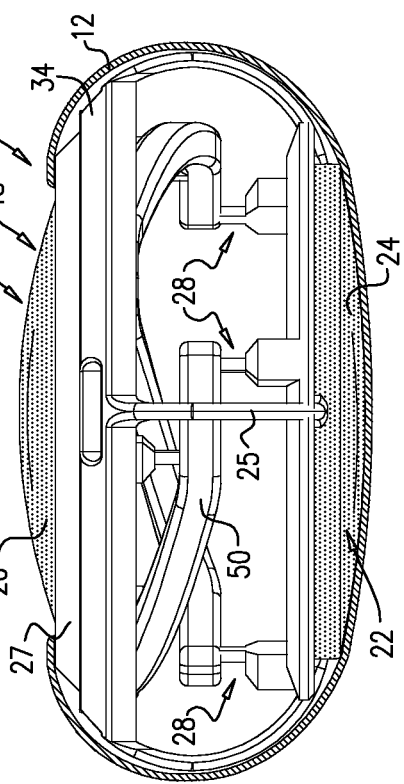
FIGS. 2A-B are side views of the lens implant of FIGS. 1A-B, showing the lens implant implanted in a natural capsular bag of the eye, in fully-unaccommodated and fully-accommodated states, respectively, in accordance with an application of the present invention.
Figure 2B:
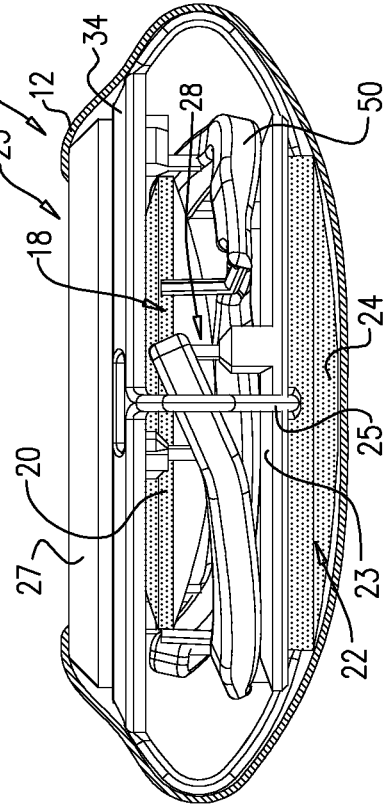

FIGS. 1A-B and 2A-B are schematic illustrations of an accommodative intraocular lens implant 10, in accordance with an application of the present invention. FIGS. 1A-B are isometric views of the lens implant. FIGS. 2A-B are side views showing the lens implant implanted in a natural capsular bag 12 of the eye. FIGS. 1A and 2A show lens implant 10 in a fully-unaccommodated state, while FIGS. 1B and 2B show the lens implant in a fully-accommodated state. Although only these two states are shown in these and the other figures, lens implant 10 is configured to assume a continuous range of accommodation between the fully-unaccommodated state and the fully-accommodated state. The fully-accommodated state provides near vision, the fully-unaccommodated state provides distance vision, and partially-accommodated states therebetween provide intermediate vision. The lens implant is configured to reach the fully-accommodated state responsively to the natural accommodation mechanism of the eye, without the need for external power.

Lens implant 10 comprises (a) an anterior floating lens unit 18, which comprises an anterior lens 20, and (b) a posterior lens unit 22, which comprises a posterior lens 24, and, typically, a posterior lens rim 23. Posterior lens unit 22 remains generally motionless with respect to the posterior portion of natural capsular bag 12 of the eye during accommodation of the lens implant. The lens implant is configured such that anterior floating lens unit 18 moves with respect to posterior lens unit 22 in response to the natural accommodation mechanism of the eye. The natural accommodation mechanism of the eye changes the shape of natural capsular bag 12, as shown in FIGS. 2A-B. In the fully-unaccommodated state shown in FIG. 2A, the ciliary muscle is relaxed and the zonular fibers are therefore tensed, causing the capsular bag to assume a relatively narrow width (in an anterior-posterior direction) and relatively large diameter. Thus shaped, the capsular bag squeezes the lens implant in the anterior-posterior direction. In contrast, in the fully-accommodated state shown in FIG. 2B, the ciliary muscle contracts, thereby releasing the tension of the zonular fibers on the capsular bag, causing the capsular bag to assume a relatively large width and relative small diameter. This shape of the capsular bag allows the lens implant to expand in the anterior-posterior direction. (As used herein, the diameter of the capsular bag means the greatest diameter of the capsular bag when viewed from its posterior aspect.)

Lens implant 10 further comprises an anterior rim complex 25 disposed such that anterior floating lens unit 18 is movable toward and away from anterior rim complex 25, in the anterior-posterior direction. Anterior rim complex 25 comprises an inner anterior ring 27 and an outer anterior ring 34. As the width (in the anterior-posterior direction) of the capsular bag changes, anterior rim complex 25 moves with respect to posterior lens unit 22, thereby changing the distance therebetween.

As described in detail hereinbelow with reference to FIGS. 4A-B, lens implant 10 further comprises one or more levers 50, which are connected to anterior floating lens unit 18, anterior rim complex 25, and posterior lens unit 22 by respective links 26, 30, and 28 (shown more clearly in FIGS. 4A-B, described hereinbelow). For example, lens implant 10 may comprise two, three (as shown in the figures), four, five, or six levers 50, and, typically, a corresponding number of each of links 26, links 30, and links 28.

Levers 50 are configured to magnify the relatively small change in the distance between anterior rim complex 25 and posterior lens unit 22, in order to move anterior floating lens unit 18 by a greater distance with respect to posterior lens unit 22. In other words, lens implant 10 is configured such that levers 50 move anterior floating lens unit 18 by a first anterior-posterior distance with respect to posterior lens unit 22 when anterior rim complex 25 moves a second anterior-posterior distance with respect to posterior lens unit 22, which first distance is greater than the second distance. Because of this distance magnification, the lens implant provides a high level of accommodation that mimics that of the natural eye. Typically, the first distance is at least 1.4 times the second distance, i.e., the lever provides a gain of at least 1.4. For example, the first distance may be at least 1.5 (e.g., at least 1.8, such as between 1.8 and 3) times the second distance.

The anterior and posterior movement of anterior floating lens unit 18 changes the distance between the anterior and posterior lens units, thereby adjusting the focal length of the lens implant. In the fully-accommodated state, which provides near vision, lens implant 10 is relatively wide (in the anterior-posterior direction), with a large separation between the anterior and posterior lens units, creating a large free space between the complexes. In the fully-unaccommodated state, which provides distance vision, the implant is relatively narrow, with a small separation between anterior and posterior complexes. Anterior floating lens unit 18 typically shifts at least 1 mm between the fully-unaccommodated and fully-accommodated states. Typical movement of the anterior lens relative to the posterior lens is between 0.5 and 2.0 mm, such as between 1 and 1.5 mm, as the lens implant transitions between the fully-unaccommodated and fully-accommodated states.

Anterior floating lens unit 18 moves within an interior space of lens implant 10, which is typically open to the natural fluid within the eye. The floating lens unit is configured to create minimum drag during movement, while maintaining the optical performance of the combined lens structure. For example, the floating lens unit may have a smooth shape, and/or may be coated with a hydrophobic coating such as silicone. Typically, the anterior and posterior lens units are configured to together create an optical structure having a total power that varies between +15D and +25D, as selected by the physician implanting the lens implant.

As mentioned above, anterior floating lens unit 18 comprises anterior lens 20, and posterior lens unit 22 comprises posterior lens 24. Each of lens units 18 and 22 may comprise one or more additional optical elements, such as additional lenses (e.g., convex lenses, concave lenses, biconvex lenses, biconcave lenses, spherical lenses, aspheric lenses, and/or astigmatic lenses), fixed power optics, deformable optics, aberration free optics, doublets, triplets, filtered optics, or combinations of these lenses, as is known in the optical arts. For some applications, anterior lens 20 is the only optical element of anterior floating lens unit 18, and/or posterior lens 24 is the only optical element of posterior lens unit 22. For some applications, one or more of lens units 18 and 22 are attached to the implant during manufacture. Alternatively or additionally, one or more of the lens units may be attached by a healthcare worker either prior to or during the implantation procedure, such as to provide the lens unit most appropriate for the particular patient.

Figure 3A:
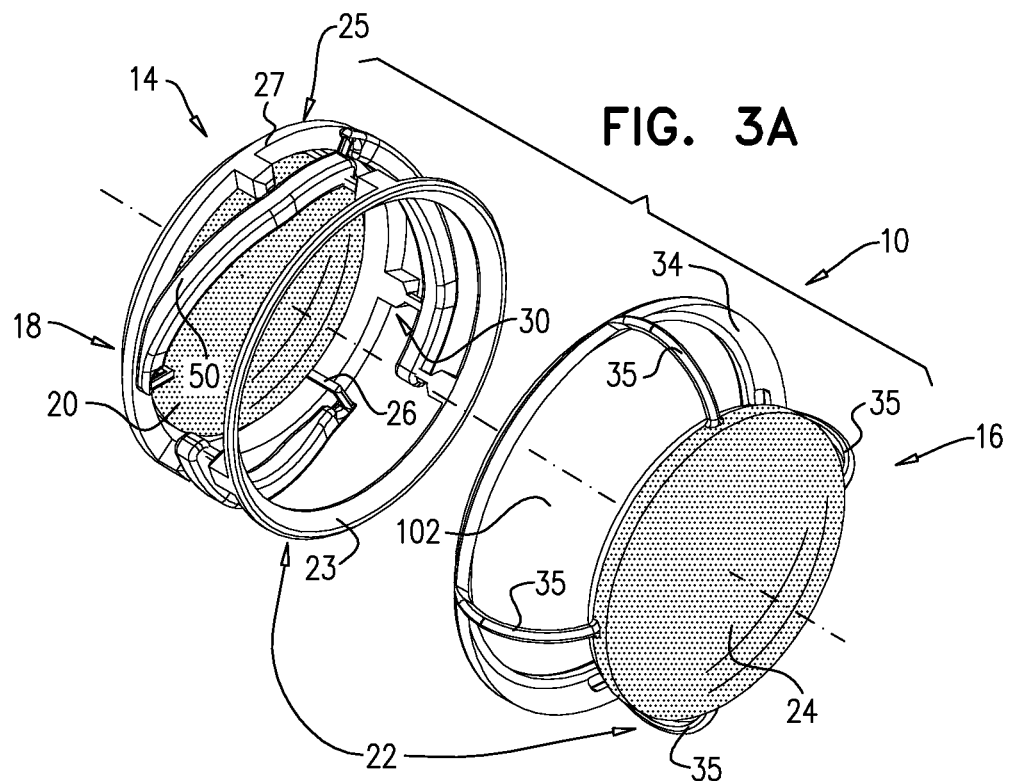
FIGS. 3A and 3B are schematic illustrations of a two-part assembly configuration of the lens implant of FIGS. 1A-2B, in disassembled and assembled states, respectively, in accordance with an application of the present invention.
Figure 3B:
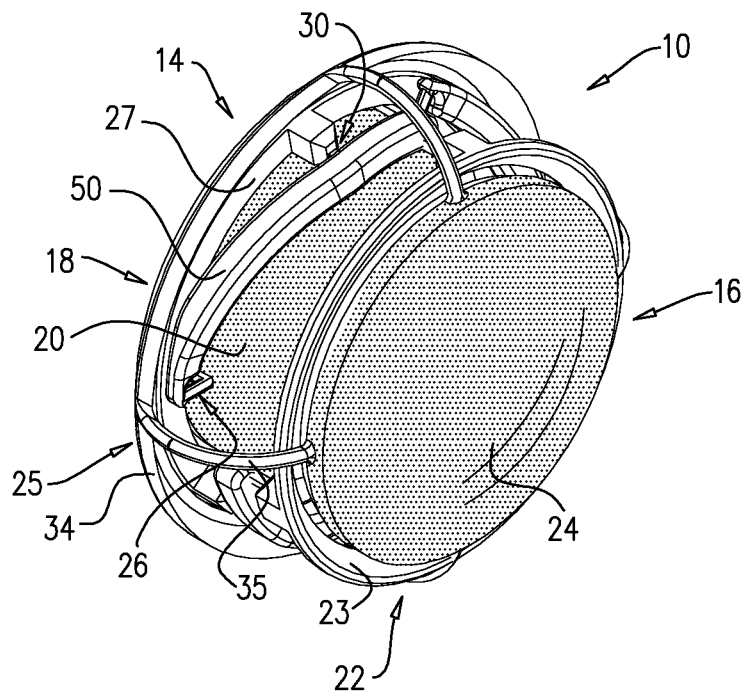

FIGS. 3A and 3B are schematic illustrations of a two-part assembly configuration of lens implant 10, in disassembled and assembled states, respectively, in accordance with an application of the present invention. In this configuration, lens implant 10 comprises two components that are initially separate from each other, and are typically assembled together in situ during implantation of the lens implant: (1) a levered complex 14 and (2) a haptic complex 16. Alternatively, lens implant 10 is manufactured as a single piece, rather than assembled in sin, such as described hereinbelow with reference to FIGS. 15A-B. Both components are shown in the fully-accommodated state in both FIGS. 3A and 3B. The resting state of the lens implant is typically the fully-accommodated state, or, optionally, slightly beyond the fully-accommodated state, such that the lens implant is always pressing the lens capsule open even when the lens implant is fully accommodated, thereby keeping the zonules in tension.

For some applications, levered complex 14 comprises the following components, each of which is described in detail hereinbelow (and perhaps can be seen more clearly in FIG. 4A, described hereinbelow):
- anterior floating lens unit 18, which comprises anterior lens 20;
- a portion of anterior rim complex 25, which portion comprises inner anterior ring 27;
- a portion of posterior lens unit 22, which portion typically comprises posterior lens rim 23;
- one or more levers 50;
- one or more anterior lens links 26;
- one or more posterior lens links 28; and
- one or more anterior rim links 30.

For some applications, haptic complex 16 comprises the following components, each of which is described in detail hereinbelow (and perhaps can be seen more clearly in FIG. 4B, described hereinbelow):
- a portion of posterior lens unit 22, which portion typically comprises posterior lens 24;
- a portion of anterior rim complex 25, which portion comprises outer anterior ring 34; and
- one or more haptics 35, which couple outer anterior ring 34 to posterior lens unit 22.

Optionally, inner anterior ring 27 and outer anterior ring 34 at least partially radially overlap upon assembly, such as at inner rim extensions 99, described hereinbelow with reference to FIGS. 13A-B.

For some applications, levered complex 14 is manufactured as single piece (such as by injection molding), and typically comprises a single material, such as silicone, acrylic, or Poly(methyl methacrylate) (PMMA). For some applications, anterior lens 20 and the other components of levered complex 14 comprise the same material (anterior lens 20 functions as a lens because of the shape thereof). Alternatively, one or more components of levered complex 14 are separately formed and coupled together during manufacture. Likewise, for some applications, haptic complex 16 is manufactured as single piece (such as by injection molding), and typically comprises a single material, such as silicone, acrylic, or Poly(methyl methacrylate) (PMMA). Alternatively, one or more components of haptic complex 16 are separately formed and coupled together during manufacture. For some applications, posterior lens 24 and the other components of haptic complex 16 comprise the same material (posterior lens 24 functions as a lens because of the shape thereof). (Although transparent, lens 20 and 24 are shaded in the figures for clarity of illustration; as mentioned above, the lenses may comprise the same material as the other components of the lens implant.)

For some applications, the material of levered complex 14 has a hardness of between 20 and 50 Shore A, and the material of haptic complex 16 has a hardness of between 20 and 50 Shore A. Thus, all components of lens implant 10 are typically flexible.

As mentioned above, levered complex 14 and haptic complex 16 are typically separately inserted into natural capsular bag 12 in a two-step insertion procedure, and assembled together in situ in the capsular bag. Haptic complex 16 is first inserted, and thereafter levered complex 14 is inserted. This two-step insertion procedure generally allows the use of a smaller incision than is necessary for a one-step insertion procedure of a single-piece implant. Upon assembly, the two portions of posterior lens unit 22 join together to form the entire posterior lens unit, as shown in FIGS. 3B and 4B. Typically, upon assembly, all of the rings and lenses of lens implant 10 are concentric.

For some applications, levered complex 14 and haptic complex 16 are preloaded into a single introducer, and separately introduced into the capsular bag from the single introducer.

For some applications, haptic complex 16 is inserted, and reshapes natural capsular bag 12. The vision of the patient is then measured. Responsively to the measured vision, a healthcare worker selects one of a plurality of available anterior floating lens units 18 having the most appropriate optical properties for the patient. A levered complex 14 having the selected anterior floating lens unit 18 is inserted into haptic complex 16. This selection procedure may provide better vision for the patient.

For some applications, for treating astigmatism, both anterior floating lens unit 18 and posterior lens unit 22 have some cylinder for treating the astigmatism. During the two-stage implantation procedure, a healthcare worker adjusts a relative angular orientation of the two lens units in order to treat the patient's astigmatism. This combination of cylinders between the two lens units allows treatment of a variety of astigmatisms with fewer different lens implants than would be necessary if separate lens implants were to be provided for each cylinder power. More generally, for some applications, anterior floating lens unit 18 and/or posterior lens unit 22 are not rotationally symmetrical. For some applications, a healthcare worker adjusts the effective diopter of lens implant 10, by rotating the lens units with respect to each other.

For some applications, for treating astigmatism, lens implant 10 has some cylinder for treating the astigmatism. Because of the cylinder, in order for the lens implant to properly correct the astigmatism, the lens implant must be properly rotationally aligned with respect to natural capsular bag 12. For some applications, in order to rotate the lens implant after insertion, the surgeon pumps (i.e., pushes anterior floating lens unit 18 in a posterior direction) to a greater extent than during normal full unaccommodation of the lens implant. Each such deep pumping action causes a slight rotation of lens implant 10 with respect to natural capsular bag 12, because when the lens implant is flat it is easier to rotate the lens implant since it is not touching the anterior capsular bag. The application of slight tangential force rotates the lens implant. Also, the levers when flattened may provide a crawling motion as they roll along the posterior of the capsular bag. The surgeon repeats this deep pumping action as many times as necessary until the desired rotational alignment is achieved. This technique optionally may be used in combination with the techniques described in the immediately preceding paragraph.

During the implantation procedure, haptic complex 16 is first inserted into natural capsular bag 12. Subsequently, levered complex 14 is inserted into the capsular bag. Posterior lens rim 23 is configured to center itself on posterior lens 24, and remain in contact with posterior lens 24, upon insertion of levered complex 14 in the capsular bag. The posterior lens rim and posterior lens thereafter stay in place together with respect to the posterior portion of capsular bag as one part, typically held together by the natural capsular bag. Outer anterior ring 34 of haptic complex 16 is configured to receive and center inner anterior ring 27 of anterior rim complex 25. After insertion, outer anterior ring 34 and inner anterior ring 27 move together in response to natural motion of the anterior portion of natural capsular bag 12. For some applications, outer anterior ring 34 and inner anterior ring 27 are both configured to come in contact with the natural capsular bag. Alternatively or additionally, for some applications, outer anterior ring 34 is configured to come in contact with the natural capsular bag, and outer anterior ring 34 and inner anterior ring 27 press against each other (optionally, using anterior inner rim extensions 99, described hereinbelow with reference to FIGS. 13A-B). Movement of the anterior portion of the capsular bag moves outer anterior ring 34, which in turn moves inner anterior ring 27. In this latter configuration, the region of contact with the capsular bag is limited to a larger diameter and thereby reduces the risk of tearing the bag (which has an anterior opening).

Haptics 35 provide a variable anterior-posterior distance between outer anterior ring 34 and posterior lens unit 22, and help position lens implant 10 properly in natural capsular bag 12. The nominal shape of the haptics is similar to or slightly wider (in the anterior-posterior direction) than the natural capsular bag when in its accommodated state. The haptics typically do not directly affect the anterior lens. The haptics typically do not directly touch anterior floating lens unit 18, including anterior lens 20 thereof. The haptics are configured to position posterior lens unit 22 in natural capsular bag 12. The forces applied by the haptics are generally insufficient to resist the shape change of natural capsular bag 12 during accommodation. Typically, levers 50 are not coupled to any of haptics 35.

Outer anterior ring 34 is shaped so as to define a central opening 102 (labeled in FIG. 3A) generally concentric with anterior lens 20. Haptics 35 are coupled to outer anterior ring 34 at respective anterior coupling sites 104 (labeled in FIG. 1B). For some applications, outer anterior ring 34 is shaped so as to define, in addition to central opening 102, one or more smaller openings 106 disposed within 500 microns of anterior coupling sites 104, respectively. These smaller openings weaken outer anterior ring 34, thereby allowing it to serve as a joint near anterior coupling sites 104; haptics 35 can thus to some degree rotate about these smaller openings. This allows outer anterior ring 34 to move in the anterior-posterior direction as lens implant 10 transitions between its fully-accommodated and fully-unaccommodated states. Outer anterior ring 34 provides a stable mount for the subsequently-implanted levered complex 14.

Figure 4A:
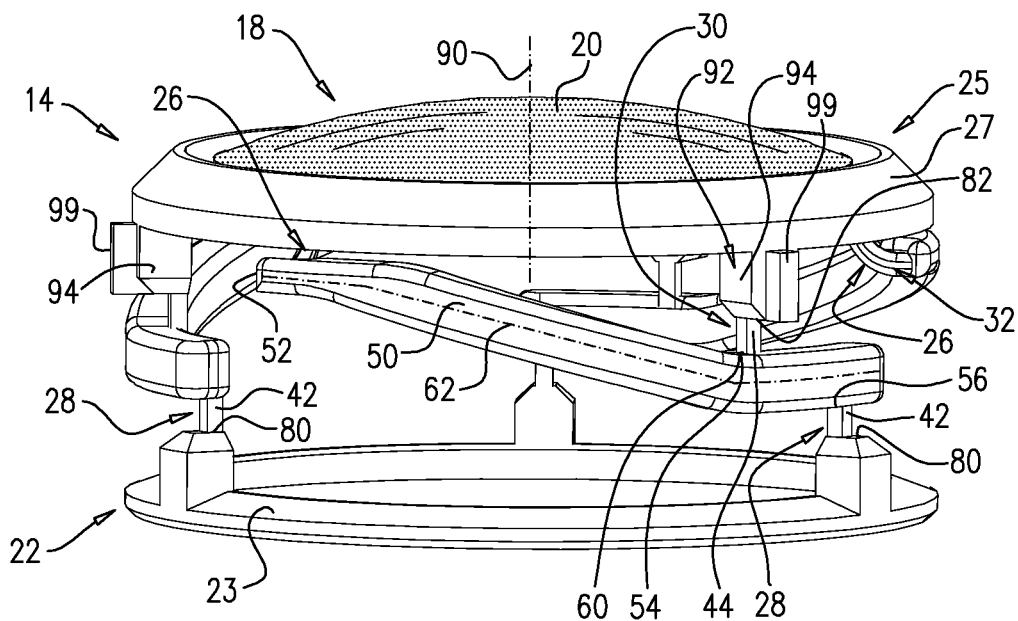
FIGS. 4A-B are schematic illustrations of the lens implant of FIGS. 1A-3B in the fully-accommodated state, in accordance with an application of the present invention.
Figure 4B:
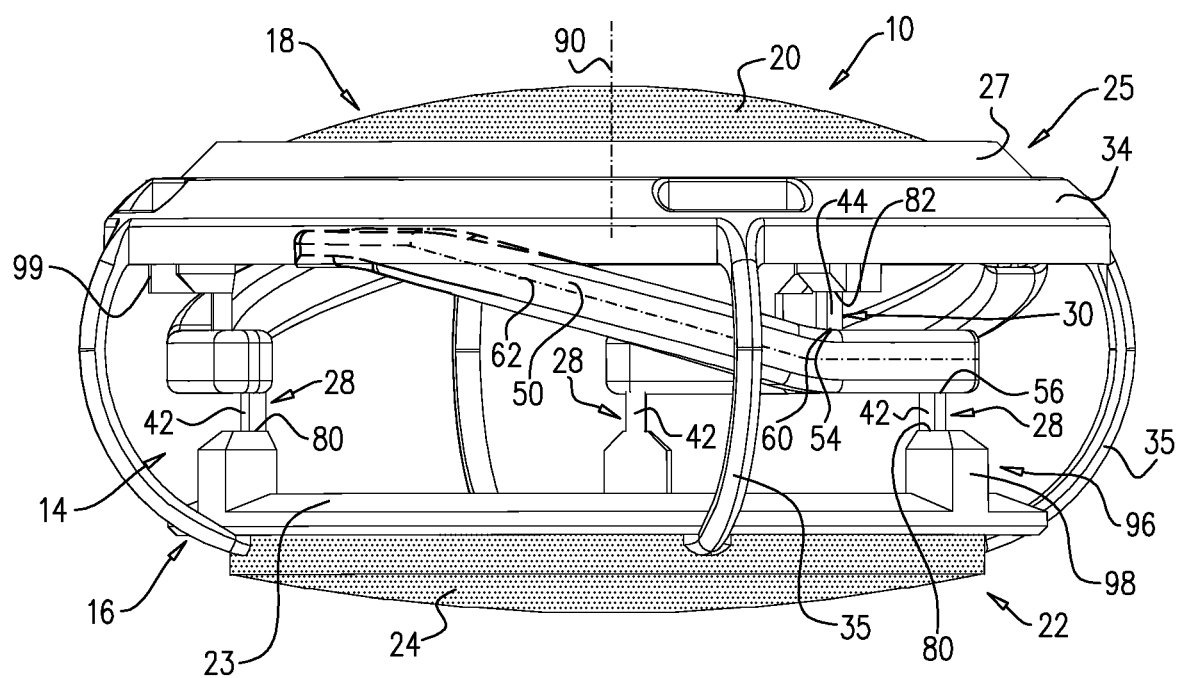

Reference is now made to FIGS. 4A-B, which are schematic illustrations of lens implant 10 in the fully-accommodated state, in accordance with an application of the present invention. FIG. 4A shows only levered complex 14, while FIG. 4B shows the fully-assembled lens implant including both levered complex 14 and haptic complex 16. (FIGS. 5C-D, described hereinbelow, show levered complex 14 in the fully-unaccommodated state.) As mentioned above with reference to FIGS. 1A-B and 2A-B, lens implant 10 comprises a plurality of links 26, 28, and 30. More particularly, lens implant 10 comprises:
  one or more anterior lens links 26, which comprise respective anterior lens jointed elements 32 (which are described in greater detail hereinbelow with reference to FIGS. 9A-D);
  one or more posterior lens links 28, which comprise respective posterior lens jointed elements 42; and
  one or more anterior rim links 30, which comprise respective anterior rim jointed elements 44.

For some applications, each of posterior lens links 28 comprises exactly one posterior lens jointed element 42. Alternatively or additionally, for some applications, each of anterior rim links 30 comprises exactly one anterior rim jointed element 44. Further alternatively or additionally, for some applications, each of anterior lens links 26 comprises exactly one anterior lens jointed element 32. Typically, anterior rim complex 25 is not itself jointed, and/or posterior lens unit 22 is not itself jointed.

Each of levers 50 is connected:
  at a first longitudinal site 52 along lever 50 (which can be better seen in FIG. 7, described hereinbelow), to anterior floating lens unit 18 by anterior lens link 26,
  at a second longitudinal site 54 along lever 50, to anterior rim complex 25 (typically to inner anterior ring 27 of the anterior rim complex) by anterior rim link 30, and
  at a third longitudinal site 56 along lever 50, to posterior lens unit 22 by posterior lens link 28.

Second longitudinal site 54 is longitudinally between first and third longitudinal sites 52 and 56 along lever 50, such that second longitudinal site 54 serves as a fulcrum 60 for lever 50. The levers, including the location of the fulcrum, are typically configured to provide a gain of at least 1.4, as described hereinabove with reference to FIGS. 1A-B and 2A-B. Lever 50 and fulcrum 60 are described in more detail hereinbelow with reference to FIGS. 8A-B.

Each of jointed elements 32, 42, and 44 joins respective pairs of elements of lens implant 10 so as to permit relative motion (particularly rotational motion) between the joined elements. Typically, posterior lens jointed elements 42 and anterior rim jointed elements 44 are configured to minimize non-rotational motion, such as radial motion, between their respective joined elements to the extent possible given other design constraints, while still allowing a small amount of radial motion. For some applications, each of posterior lens jointed elements 42 is configured to allow third longitudinal site 56 along lever 50 to move radially no more than 200 microns with respect to posterior-lens-complex-connection site 80 of posterior lens unit 22, as lens implant 10 transitions between the fully-accommodated and the fully-unaccommodated states. (As used in the present application, including in the claims, transitioning between the fully-accommodated and the fully-unaccommodated states is to be understood as meaning making a transition that begins at the fully-accommodated state and continues all the way to the fully-unaccommodated state, or vice versa.)

Anterior lens jointed elements 32 are typically configured to allow a small amount of radial motion between lever 50 and anterior floating lens unit 18, such as described hereinbelow with reference to FIGS. 9A-D. For some applications, each of anterior lens jointed elements 32 is configured to allow first longitudinal site 52 along lever 50 to move radially between 200 and 500 microns with respect to an anterior-lens-complex-connection site 84 of anterior floating lens unit 18 (labeled in FIGS. 5C-D and 8A), as lens implant 10 transitions between the fully-accommodated and the fully-unaccommodated states.

As used in the present application, including the claims, "radial" means in a direction toward or away from a central optical axis 90 of anterior lens 20 (labeled in FIGS. 4A-B).

In some configurations, each of the jointed elements comprises a small, relatively thin shaft. For these configurations, as well as for other configurations of the jointed elements, in order to minimize non-rotational motion a length of each of anterior lens jointed elements 32 is typically less than 1000 microns, such as less than 500 microns, e.g., less than 300 microns. Alternatively or additionally, a length of each of posterior lens jointed elements 42 is less than 1000 microns, such as less than 500 microns, e.g., less than 300 microns. Further alternatively or additionally, a length of each of anterior rim jointed elements is less than 1000 microns, such as less than 500 microns, e.g., less than 300 microns. Typically, each of the jointed elements has a cross-sectional area measured along the joined element perpendicular to a longitudinal axis of the jointed element that is less than 0.04 mm2, such as less than 0.03 mm2. Typically, anterior lens, posterior lens, and anterior rim jointed elements 32, 42, and 44 comprise respective non-sliding joints. Alternatively or additionally, for some applications, anterior lens, posterior lens, and anterior rim jointed elements 32, 42, and 44 comprise respective rotating joints.

Anterior rim links 30 are connected to anterior rim complex 25 at respective anterior-rim-complex-connection sites 82 of anterior rim complex 25. Anterior lens links 26 are connected to anterior floating lens unit 18 at respective anterior-lens-complex-connection sites 84 of anterior floating lens unit 18 (labeled in FIGS. 5C-D and 8A). Posterior lens links 28 are connected to posterior lens unit 22 at respective posterior-lens-complex-connection sites 80 of posterior lens unit 22.

Typically, as lens implant 10 transitions between the fully-accommodated and the fully-unaccommodated states:
- a location of each of second longitudinal sites 54 relative to anterior rim complex 25 changes by less than 500 microns, e.g., less than 200 microns, and/or by less than 50% of a distance between second longitudinal site 54 and its respective anterior-rim-complex-connection sites 82 when the lens implant is in the fully-accommodated state;
- a location of each of first longitudinal sites 52 relative to anterior floating lens unit 18 changes by less than 500 microns, e.g., less than 200 microns, and/or by less than 50% of a distance first longitudinal site 52 and its respective anterior-lens-complex-connection site 84 when the lens implant is in the fully-accommodated state; and/or
- a location of each of third longitudinal sites 56 relative to posterior lens unit 22 changes by less than 500 microns, e.g., less than 200 microns, and/or by less than 50% of a distance third longitudinal site 56 and its respective posterior-lens-complex-connection site 80 when the lens implant is in the fully-accommodated state.

Alternatively or additional, for some applications, during a change in distance between posterior lens rim 23 and anterior ring 27 during accommodation of lens implant 10:
- a location of each of second longitudinal sites 54 relative to anterior rim complex 25 changes by less than 50% of the change in distance between posterior lens rim 23 and anterior ring 27;
- a location of each of first longitudinal sites 52 relative to anterior floating lens unit 18 changes by less than 50% of the change in distance between posterior lens rim 23 and anterior ring 27; and/or
- a location of each of third longitudinal sites 56 relative to posterior lens unit 22 changes by less than 50% of the change in distance between posterior lens rim 23 and anterior ring 27.

Lens implant 10 is typically configured such that levers 50 do not move, or move only slightly, radially toward or away from central optical axis 90 of anterior lens 20, as lens implant 10 transitions between the fully-accommodated and the fully-unaccommodated states. For example, lens implant 10 may be configured such that, as lens implant 10 transitions between the fully-accommodated and the fully-unaccommodated states:
- a greatest change in distance between any portion of each of levers 50 and central optical axis 90 is less than 500 microns, e.g., less than 250 microns, and/or less than 10%, e.g., less than 5%, of a diameter of anterior lens 20;
- a change in distance between each of second longitudinal sites 54 and central optical axis 90 is less than 500 microns, e.g., less than 250 microns, and/or less than 10%, e.g., less than 5%, of the diameter of anterior lens 20;
- a change in distance between each of third longitudinal sites 56 and central optical axis 90 is less than 500 microns, e.g., less than 250 microns, and/or less than 10%, e.g., less than 5%, of the diameter of anterior lens 20; and/or
- a greatest change in distance between any portion of each of posterior lens links 28 and central optical axis 90 is less than 500 microns, e.g., less than 250 microns, and/or less than 10%, e.g., less than 5%, of the diameter of anterior lens 20.

For some applications, posterior-lens-complex-connection and anterior-rim-complex-connection sites 80 and 82 of each respective lever 50 are circumferentially offset from each other with respect to central optical axis 90, such as by at least 15 degrees (e.g., at least 20 degrees) around central optical axis 90.

For some applications, when lens implant 10 is in the fully-unaccommodated state, third longitudinal site 56 along lever 50 is closer to anterior rim complex 25 than first longitudinal site 52 along lever 50 is to anterior rim complex 25. These relative distances reverse when lens implant 10 is in the fully-accommodated state, such that first longitudinal site 52 is closer to anterior rim complex 25 than third longitudinal site 56 is to anterior rim complex 25.

For some applications, anterior floating lens unit 18 further comprises one or more attachment elements, and the lever is connected to the attachment elements by respective anterior lens links 26 (configuration not shown). For example, the attachment elements may comprise respective anterior lens posts, and the lever is connected to the anterior lens posts by respective anterior lens links 26 (configuration not shown). Alternatively, the one or more attachment elements may comprise an anterior lens rim, and the lever is connected to the anterior lens rim by the anterior lens links (configuration not shown).

For some applications, anterior rim complex 25 (e.g., inner anterior ring 27 thereof) further comprises one or more attachment elements 92, and lever 50 is connected to the attachment elements by respective anterior rim links 30. For example, attachment elements 92 may comprise respective anterior posts 94, and lever 50 is connected to anterior posts 94 by respective anterior rim links 30. Optionally, each of anterior posts 94 is oriented within 5 degrees of parallel to the anterior-posterior direction, such as parallel to the anterior-posterior direction.

For some applications, posterior lens unit 22 further comprises one or more attachment elements 96, and lever 50 is connected to the attachment elements by respective posterior lens links 28. For example, attachment elements 96 may comprise respective posterior posts 98, and lever 50 is connected to posterior posts 98 by respective posterior lens links 28. Alternatively or additionally, the one or more attachment elements may comprise posterior lens rim 23, and lever 50 is connected to posterior lens rim 23 by posterior lens links 28. For applications in which the one or more attachment elements 96 comprise both posterior posts 98 and posterior lens rim 23, posterior posts 98 are connected to posterior lens rim 23, and lever 50 is connected to posterior posts 98 by respective posterior lens links 28.

Figure 5A:
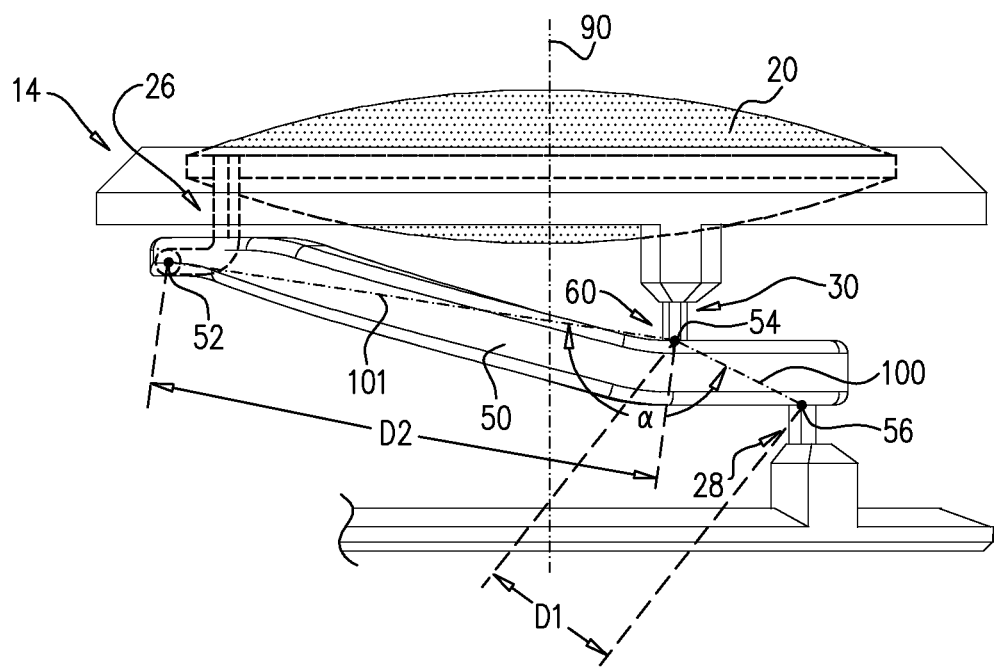
FIGS. 5A-B are schematic illustrations of a levered complex of the lens implant of FIGS. 1A-3B in the fully-accommodated and fully-unaccommodated states, respectively, in accordance with an application of the present invention.
Figure 5B:
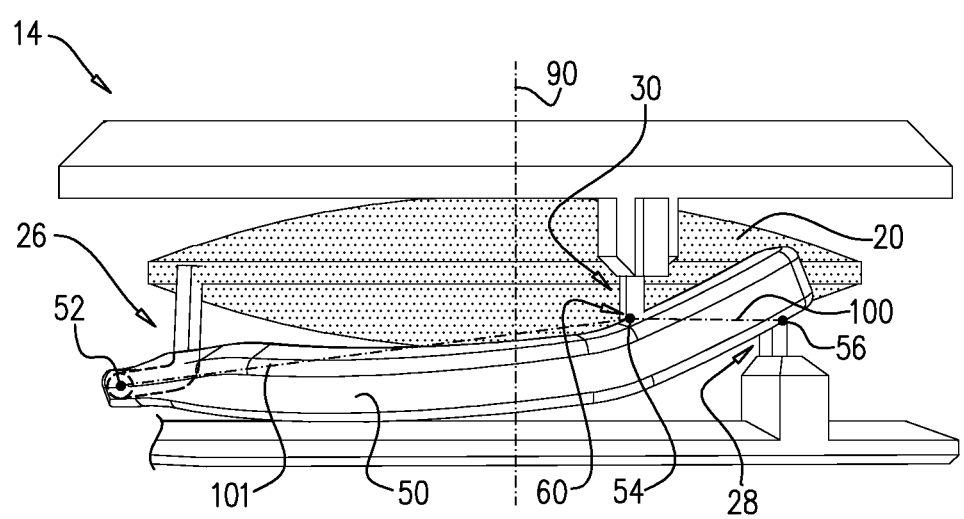

Reference is made to FIGS. 5A and 5B, which are schematic illustrations of levered complex 14 in the fully-accommodated and fully-unaccommodated states, respectively, in accordance with an application of the present invention. For clarity of illustration, only a single one of levers 50 is shown, although in practice levered complex 14 typically comprises at least three levers 50, as described above. For some applications, a first straight line segment 100 between second longitudinal site 54 along lever 50 (which serves as fulcrum 60) and third longitudinal site 56 along lever 50 is horizontal at some point during the transition between the fully-accommodated and fully-unaccommodated states, inclusive of the endpoints of the transition (i.e., the fully-accommodated and fully-unaccommodated states themselves). In other words, first line segment 100 is parallel to a plane perpendicular to central optical axis 90 during the transition. For example, first line segment 100 is shown horizontal in FIG. 5B, in which levered complex 14 is in the fully-unaccommodated state. Alternatively, first line segment 100 is nearly horizontal at some point during the transition (inclusive of the endpoints of the transition), e.g., defines an angle of less than 15 degrees, such as less than 5 degrees, with the plane perpendicular to central optical axis 90. For some applications, first line segment 100 rotates at least 10 degrees, no more than 35 degrees, and/or between 10 and 35 degrees, such as at least 18 degrees, no more than 28 degrees, and/or between 18 and 28 degrees, as lens implant 10 transitions between the fully-accommodated and fully-unaccommodated states, e.g., 24 degrees (i.e., during a full stroke of the lever). Alternatively or additionally, for some applications, at a midpoint of the rotation of first line segment 100, as lens implant 10 transitions between the fully-accommodated and fully-unaccommodated states (i.e., during a full stroke of the lever), first line segment 100 defines an angle of less than 15 degrees, such as less than 5 degrees, the plane perpendicular to central optical axis 90. e.g., is parallel to the plane.

Alternatively or additionally, for some applications, a second straight line segment 101 between second longitudinal site 54 along lever 50 (which serves as fulcrum 60) and first longitudinal site 52 along lever 50 is horizontal at some point during the transition between the fully-accommodated and fully-unaccommodated states, inclusive of the endpoints of the transition (i.e., the fully-accommodated and fully-unaccommodated states themselves). In other words, second line segment 101 is parallel to a plane perpendicular to central optical axis 90 during the transition. Alternatively, second line segment 101 is nearly horizontal at some point during the transition (inclusive of the endpoints of the transition), e.g., defines an angle of less than 15 degrees, such as less than 5 degrees, degrees with the plane perpendicular to central optical axis 90. Alternatively or additionally, for some applications, at a midpoint of the rotation of second line segment 101, as lens implant 10 transitions between the fully-accommodated and fully-unaccommodated states (i.e., during a full stroke of the lever), second line segment 101 defines an angle of less than 15 degrees, such as less than 5 degrees, the plane perpendicular to central optical axis 90, e.g., is parallel to the plane.

Typically, an angle α (alpha) between first line segment 100 and second line segment 101 is greater than 120 degrees, such as greater than 150 degrees, e.g., 180 degrees (i.e., the line segments are collinear to each other). For example, the angle may be 135 degrees. In other words, the functional portion of lever 50 is generally straight.

Typically, second longitudinal site 54 is closer to third longitudinal site 56 than to first longitudinal site 52. For some applications, a first distance D1 between second longitudinal site 54 and third longitudinal site 56 is less than 70% of a second distance D2 between first longitudinal site 52 and second longitudinal site 54; such a location of anterior rim link 30 along lever 50 typically provides a gain of at least 1.4. For some applications, first distance D1 is less than 30% of second distance D2, which typically provides a gain of at least 3.3. For some applications, first distance D1 is at least 500 microns. Typically, first distance D1 is at least 10%, typically at least 33%, of second distance D2. Typically, first longitudinal site 52 is near a first end 53 of lever 50, such as within 10% of a total length of lever 50, measured along the central longitudinal axis (as defined below), from first end 53. (First and second distances D1 and D2 are the lengths of straight line segments 100 and 101, respectively.)

(It is to be understood that first and second straight line segments 100 and 101 are not physical components of lens implant 10, but rather geometric constructs used to describe certain properties of the implant.)

Figure 5C:
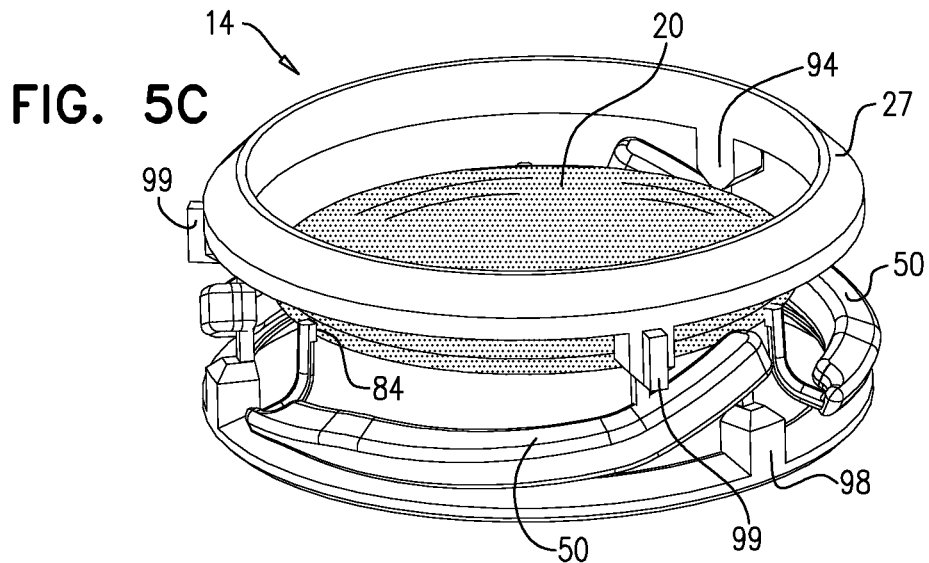
FIGS. 5C-D are schematic illustrations of a levered complex of the lens implant of FIGS. 1A-3B in the fully-unaccommodated state, in accordance with an application of the present invention.
Figure 5D:
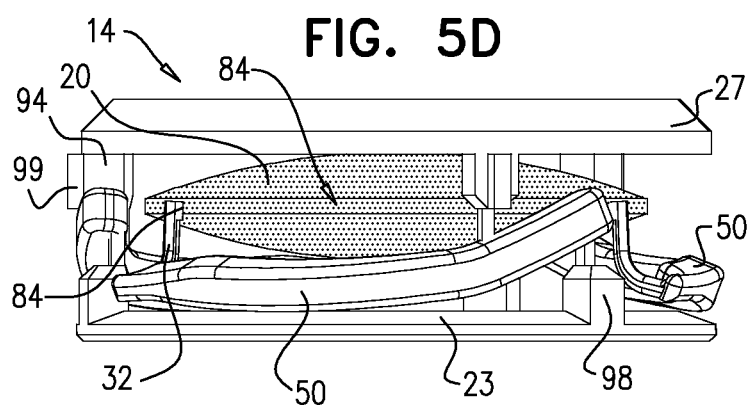

Reference is made to FIGS. 5C-D, which are schematic illustrations of levered complex 14 in the fully-unaccommodated state, in accordance with an application of the present invention. FIG. 5C is an isometric view, and FIG. 5D is a side view of levered complex 14. FIGS. 5C-D provide additional views of levered complex 14, which, unlike FIGS. 1A and 2A, are not partially blocked by haptic complex 16.

Figure 6:
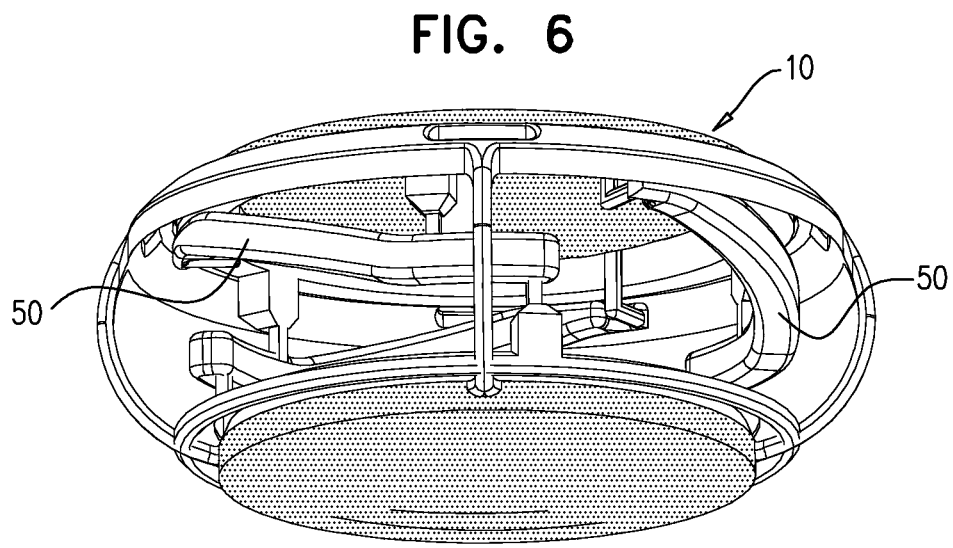
FIG. 6 is a schematic isometric view of the lens implant of FIGS. 1A-3B in the fully-accommodated state, in accordance with an application of the present invention.

Reference is made to FIG. 6, which is a schematic isometric view of lens implant 10 in the fully-accommodated state, in accordance with an application of the present invention. This view is similar to that of FIG. 1B, described hereinabove, except that in FIG. 1B lens implant 10 is shown from an anterior-lateral direction, while in FIG. 6 lens implant 10 is shown from a posterior-lateral direction.

Reference is made to FIG. 7, which is a schematic view of one of levers 50, in accordance with an application of the present invention. The view also includes one of anterior lens links 26 and one of anterior rim links 30. As used in the present application, including in the claims, the central longitudinal axis of a lever is the set of all centers of all respective minimum bounding circles at all respective longitudinal locations along the lever. Each of the minimum bounding circles is the smallest circle that completely contains therewithin the cross-section of the lever at the longitudinal location of the minimum bounding circle. (Each of the cross-sections is perpendicular to the central longitudinal axis.)

For some applications, each of levers 50 defines (a) a first point 70 on central longitudinal axis 62 (as defined hereinabove with reference to FIG. 7) longitudinally aligned with first longitudinal site 52, (b) a third point 74 on central longitudinal axis 62 longitudinally aligned with third longitudinal site 56, and (c) a plurality of second points at all respective longitudinal locations between first and third points 70 and 74 along central longitudinal axis 62. Each of levers 50 further defines a plurality of line segment pairs, which consist of (a) respective first straight line segments between first point 70 and respective ones of the second points and (b) respective second straight line segments between the respective ones of the second points and third point 74. The first and the second line segments of each of the line segment pairs define an angle therebetween of at least 120 degrees, such as at least 150 degrees. By way of example, in FIG. 7 (a) one of the second points is labeled with reference numeral 72, (b) the respective first and second line segments of second point 72 are labeled with reference numerals 76 and 78, respectively, and (c) the angle between first and second line segments 76 and 78 is labeled by β (beta). It is noted that the points and line segments described in this paragraph are not physical features of levers 50, but rather are conceptually defined by the levers in order to define certain dimensional properties of the levers. (It is also noted that the curvature of lever 50 around longitudinal axis 62 accounts for a substantial portion of these angles.)

For some applications, each of levers 50, at each of all longitudinal locations therealong longitudinally between first and third longitudinal sites 52 and 56, is shaped so as to have a respective shape feature selected from the group of shape features consisting of:

lever 50 is straight at the longitudinal location, lever 50 is curved at the longitudinal location. Typically, lever 50, at each of the longitudinal locations at which lever 50 is curved, has a radius of curvature of at least 50% of a radius of anterior lens 20, and lever 50 defines an angle of at least 120 degrees, such as 150 degrees at the longitudinal location (assuming that the lever would have an angle of 180 degrees if straight).

Figure 8A:
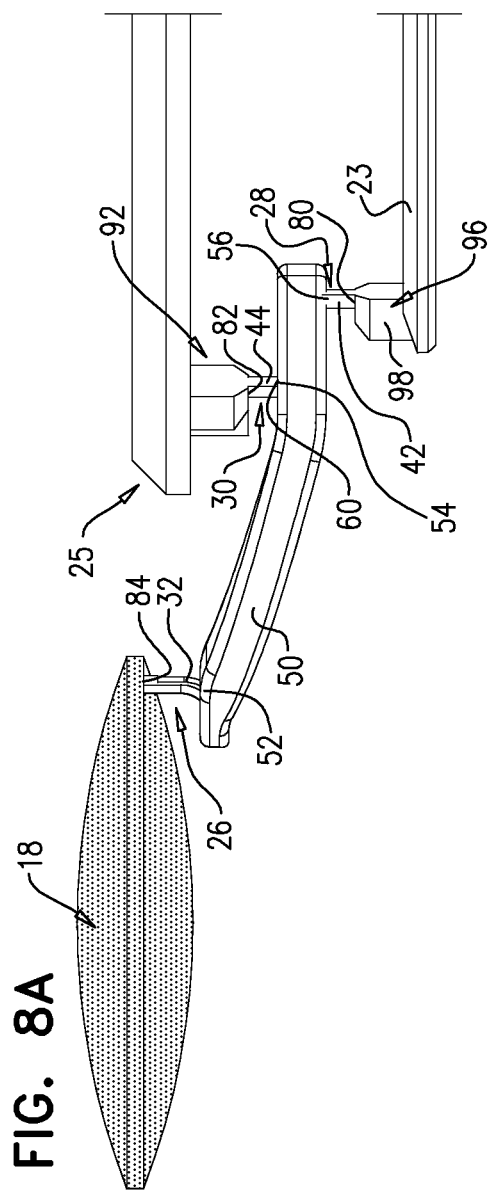
FIGS. 8A-B are schematic illustrations of a lever of the lens implant of FIGS. 1A-3B and its functional relationships to other components of the lens implant, in accordance with an application of the present invention.
Figure 8B:
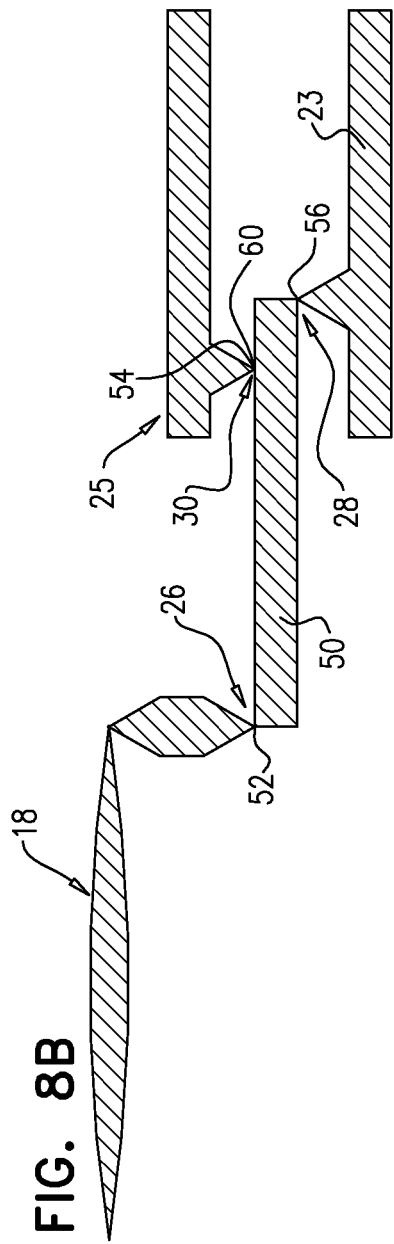

Reference is now made to FIGS. 8A-B, which are schematic illustrations of one of levers 50 and its functional relationships to other components of lens implant 10, in accordance with an application of the present invention. In these figures, some of the components of lens implant 10 are schematically arranged in order to conceptually illustrate how lever 50 functions as a first-class lever. These components of lens implant 10 are not actually arranged as shown in FIGS. 8A-B.

FIGS. 8A-B show fulcrum 60 at second longitudinal site 54, between first and third longitudinal sites 52 and 56, closer to third longitudinal site 56 than to first longitudinal site 52. Lever 50 is a first-class lever that pivots at fulcrum 60. Because fulcrum 60 is closer to third longitudinal site 56 than to first longitudinal site 52, lever 50 magnifies the anterior-posterior motion of first longitudinal site 52, resulting in greater anterior-posterior motion of anterior floating lens unit 18. Lever 50 is typically fairly stiff, such that it substantially does not change shape as it pivots during accommodation of lens implant 10 during normal implanted use. For some applications, in order to provide such stiffness, an average cross-sectional area of lever 50, measured along the lever perpendicular to central longitudinal axis 62, longitudinally between first and third longitudinal sites 52 and 56, equals at least 10 times, no more than 20 times, and/or between 10 and 20 times an average cross-sectional area of anterior lens, posterior lens, and anterior rim jointed elements 32, 42, and 44, measured therealong perpendicular to their respective longitudinal axes. Alternatively or additionally, for some applications, the average cross-sectional area of lever 50, measured along the lever perpendicular to central longitudinal axis 62, longitudinally between first and third longitudinal sites 52 and 56, is at least 0.1 mm2, such as at least 0.2 mm2.

Figure 9A:
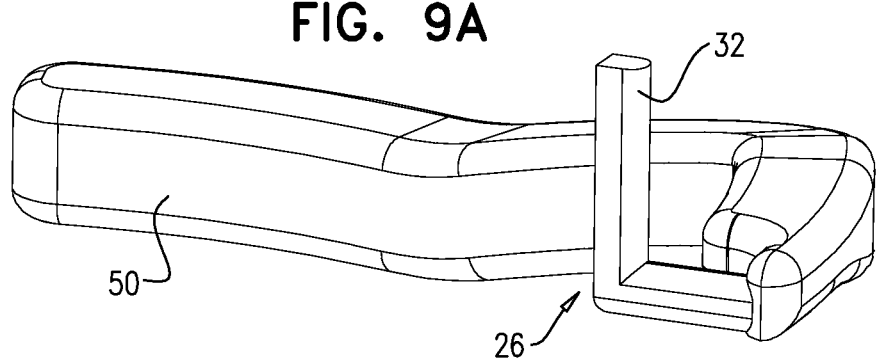
FIGS. 9A-D are schematic illustrations of components of the lens implant of FIGS. 1A-3B including anterior lens links thereof, in accordance with an application of the present invention.
Figure 9B:
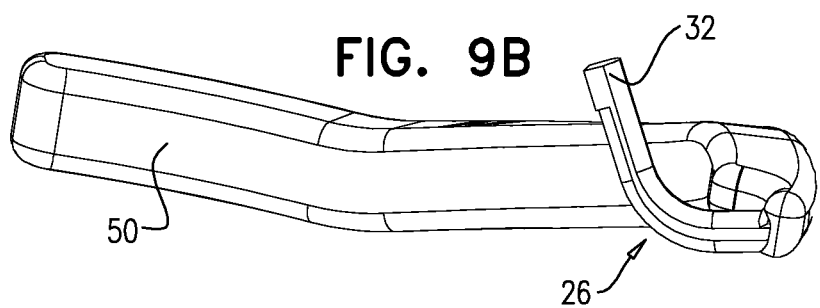

Reference is now made to FIGS. 9A-D, which are schematic illustrations of components of lens implant 10 including anterior lens links 26, in accordance with an application of the present invention. As mentioned above, anterior lens jointed elements 32 are typically configured to allow a small amount of radial motion between lever 50 and anterior floating lens unit 18. For some applications, as shown in FIG. 9B (and the other figures, other than FIG. 9A), in order to provide the radial motion, anterior lens jointed element 32 of each of anterior lens links 26 is rounded. For other applications, as shown in FIG. 9A, anterior lens jointed element 32 is L-shaped. For some applications, each of anterior lens jointed elements 32 is long enough to behave as a short link with two joints at respective ends of the element.

Figure 9C:
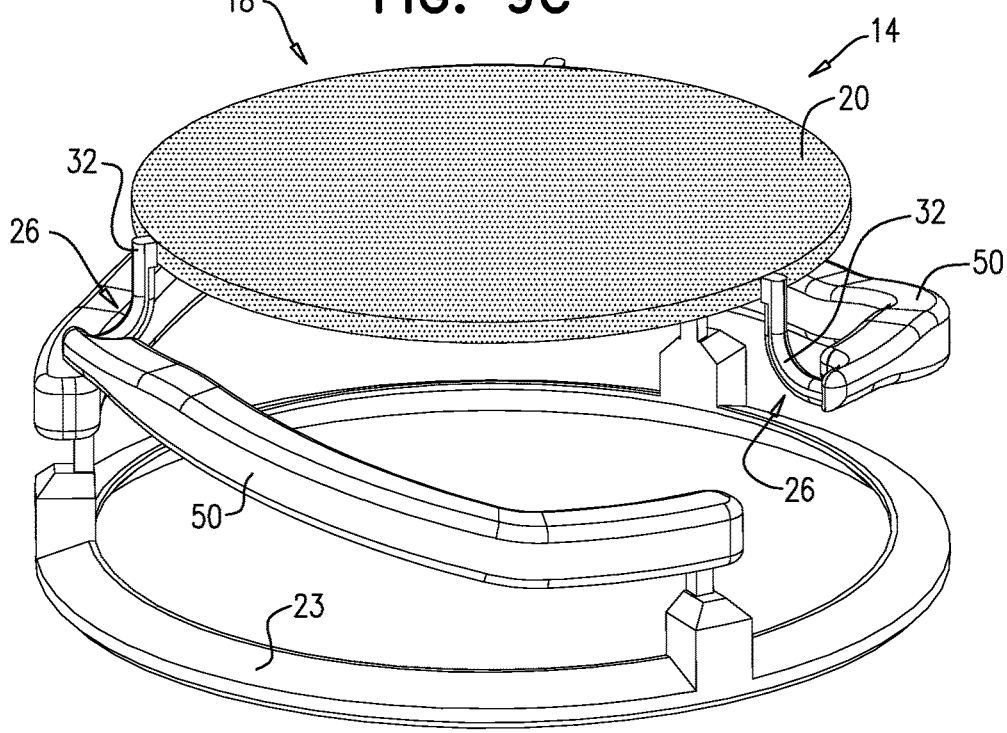
Figure 9D:
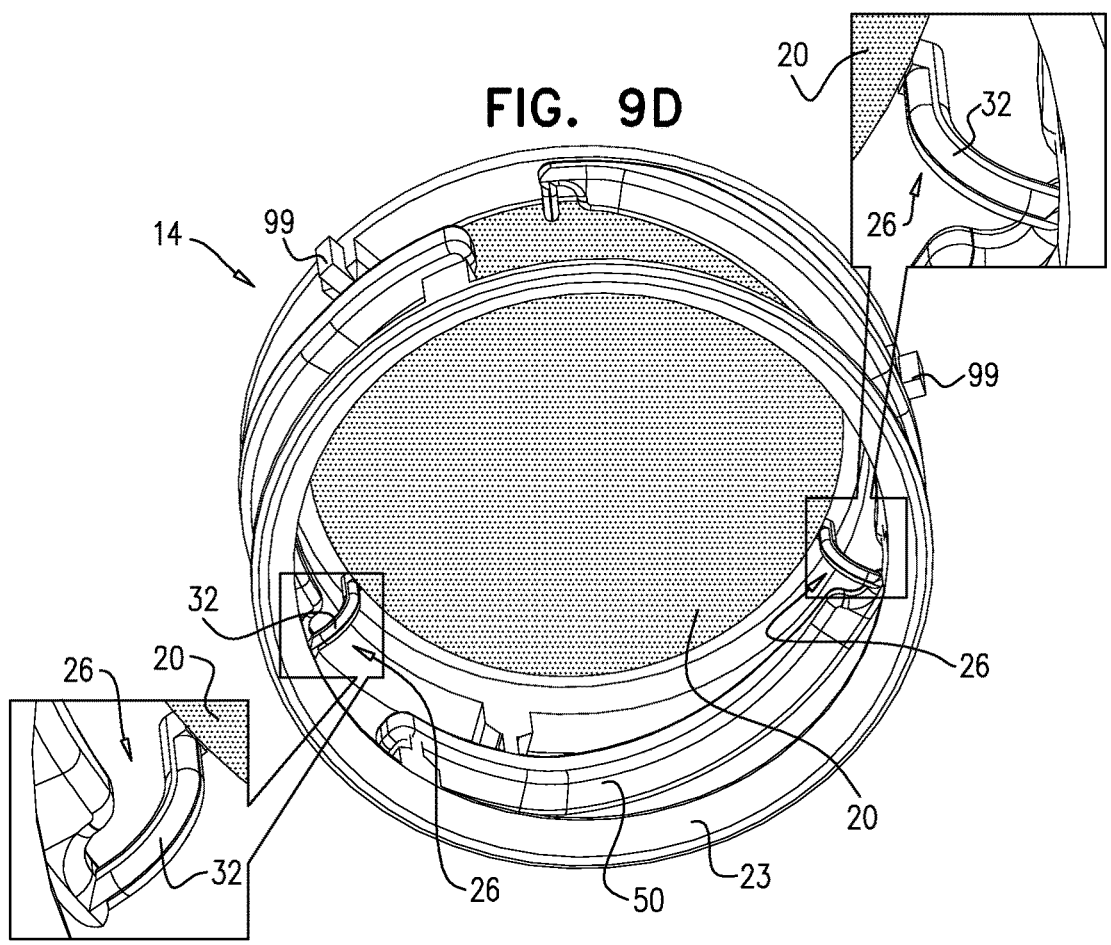

FIGS. 9C and 9D provide additional views of levered complex 14 that illustrate the connection between anterior floating lens unit 18 and levers 50 provided by anterior lens jointed elements 32 of anterior lens links 26. For clarity of illustration, to provide a clear view of levers 50 and anterior lens jointed elements 32, inner anterior ring 27, anterior posts 94, and anterior rim links 30 are not shown in FIG. 9C.

Figure 10A:
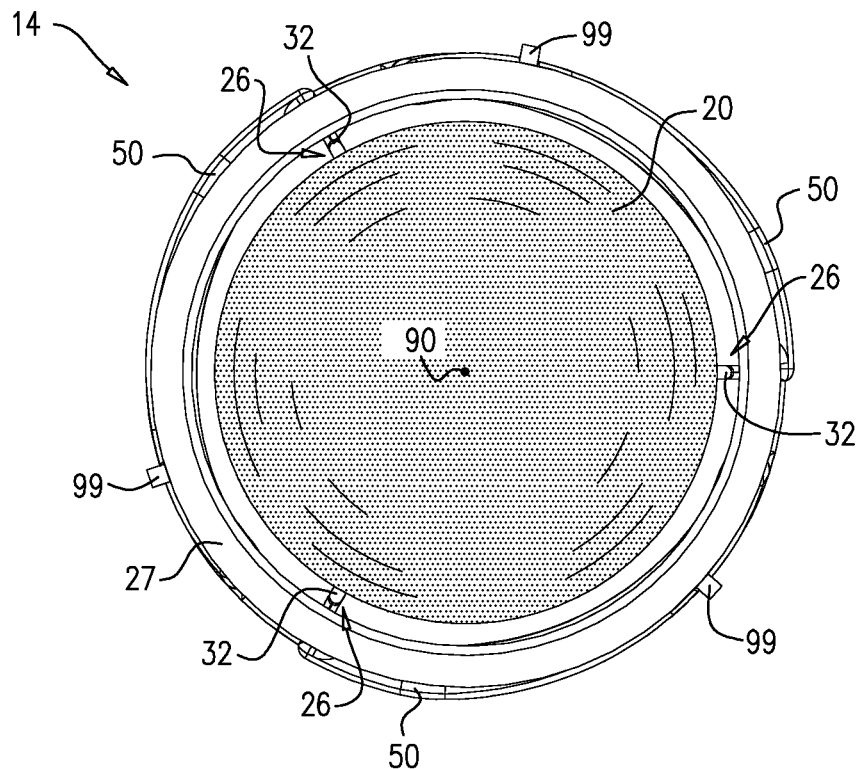
FIGS. 10A-B are schematic illustrations of a levered complex of the lens implant of FIGS. 1A-3B viewed from the anterior direction, in accordance with an application of the present invention.
Figure 10B:
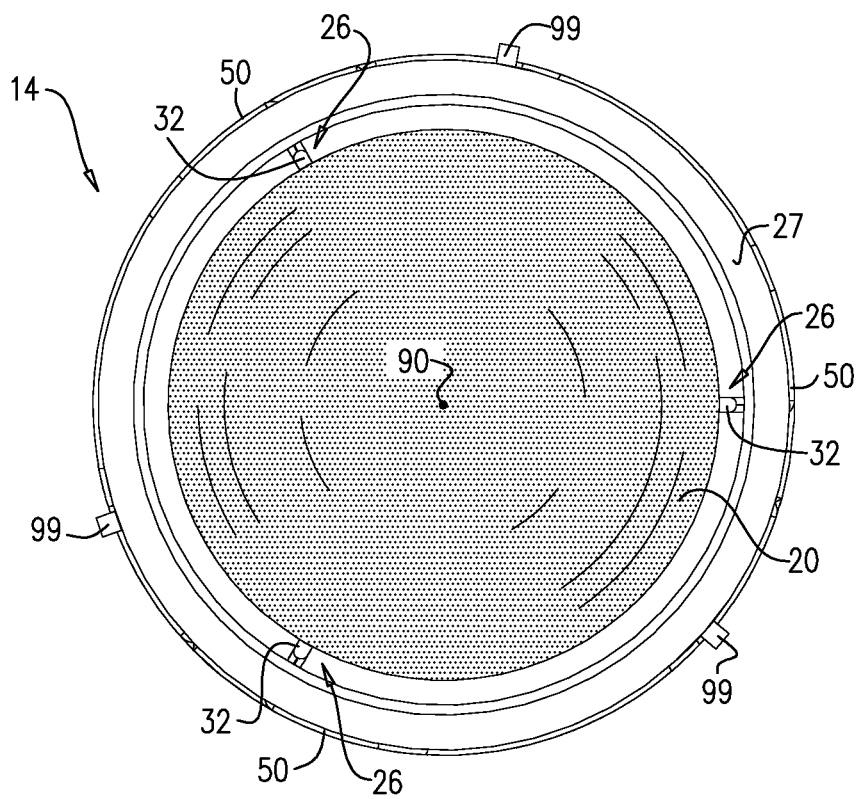
Figure 11:
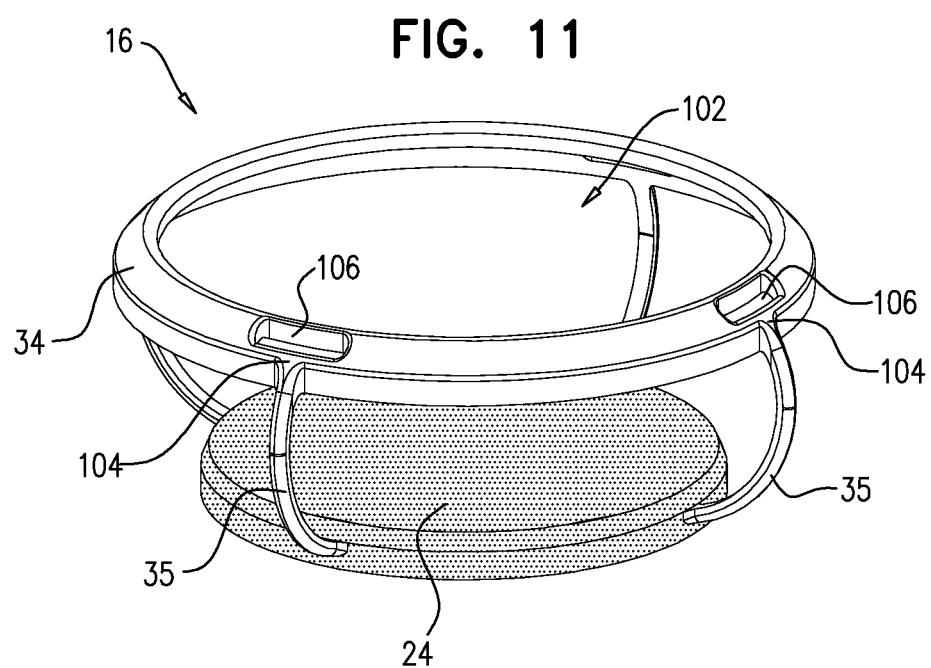
FIG. 11 is a schematic illustration of a haptic complex of the lens implant of FIGS. 1A-3B, in accordance with an application of the present invention.

Reference is made to FIGS. 10A-B, which are schematic illustrations of levered complex 14 viewed from the anterior direction, in accordance with an application of the present invention. FIG. 10A shows levered complex 14 when lens implant 10 is in the fully-unaccommodated state, while FIG. 10B shows levered complex 14 when lens implant 10 is in the fully-accommodated state. Anterior lens jointed element 32 provides articulation in two axes. During accommodation of lens implant 10, the end of lever 50 connected to anterior floating lens unit 18 moves slightly inwardly with respect to central optical axis 90 (e.g., between 100 and 200 microns of motion toward axis 90). The articulation provided by anterior lens jointed elements 32 enables such motion.

Reference is again made to FIGS. 1A-2B and 4A-B. As levers 50 pivot during accommodation of lens implant 10, the circumferential distance between jointed elements 42 and 44 changes. This change in distance is relatively small because of the predominantly horizontal orientations of levers 50, as mentioned above.

In order to accommodate this small change in distance, lens implant 10 is configured such that anterior rim complex 25 is rotatable with respect to posterior lens unit 22 to a small extent as anterior floating lens unit 18 moves toward and away from anterior rim complex 25 in the anterior-posterior direction. For example, the extent of rotation may be between 100 and 200 microns, and/or at least 1 degree, such as at least 2 degrees, and/or less than 4 degrees, such as less than 3 degrees, around central optical axis 90, as anterior floating lens unit 18 moves toward and away from anterior rim complex 25 in the anterior-posterior direction as lens implant 10 transitions from the fully-accommodated state to the fully-unaccommodated state. This minimal rotation is readily absorbed by sliding of components of lens implant 10 relative to natural capsular bag 12, by small deformation of components of lens implant 10, by sliding between levered complex 14 and haptic complex 16, and/or by flexibility in natural capsular bag 12 and/or the links and joints of lens implant 10.

Reference is now made to FIG. 1, which is a schematic illustration of haptic complex 16, in accordance with an application of the present invention. This figure shows elements of haptic complex 16 described hereinabove with reference to FIGS. 3A-B.

Figure 12A:
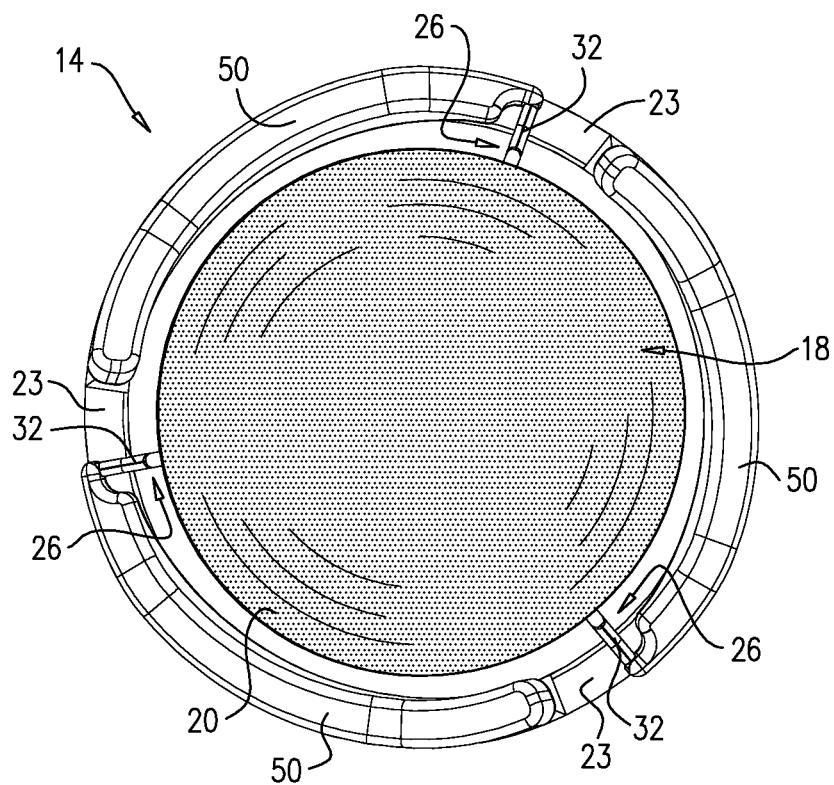
FIGS. 12A-B are schematic illustrations of the lens implant of FIGS. 1A-3B viewed from an anterior direction, in accordance with respective applications of the present invention.
Figure 12B:
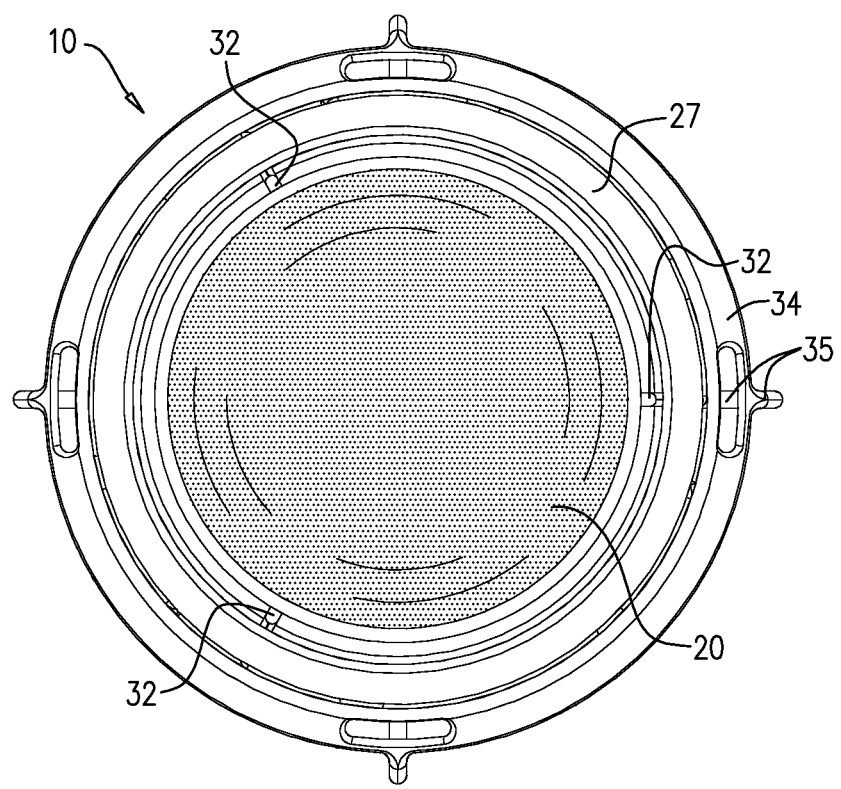

FIGS. 12A-B are schematic illustrations of lens implant 10 viewed from an anterior direction, in accordance with respective applications of the present invention. FIG. 12A shows levered complex 14; for clarity of illustration, to provide a clear view of levers 50, inner anterior ring 27, anterior posts 94, and anterior rim links 30 are not shown in the figure. In this configuration, levered complex 14 comprises exactly three levers 50, which are arranged circumferentially around anterior floating lens unit 18 (and anterior lens 20 thereof). As can be seen, levers 50 are curved around the circumference of levered complex 14, generally above respective portions of posterior lens rim 23. FIG. 12B shows assembled lens implant 10.

Figure 13A:
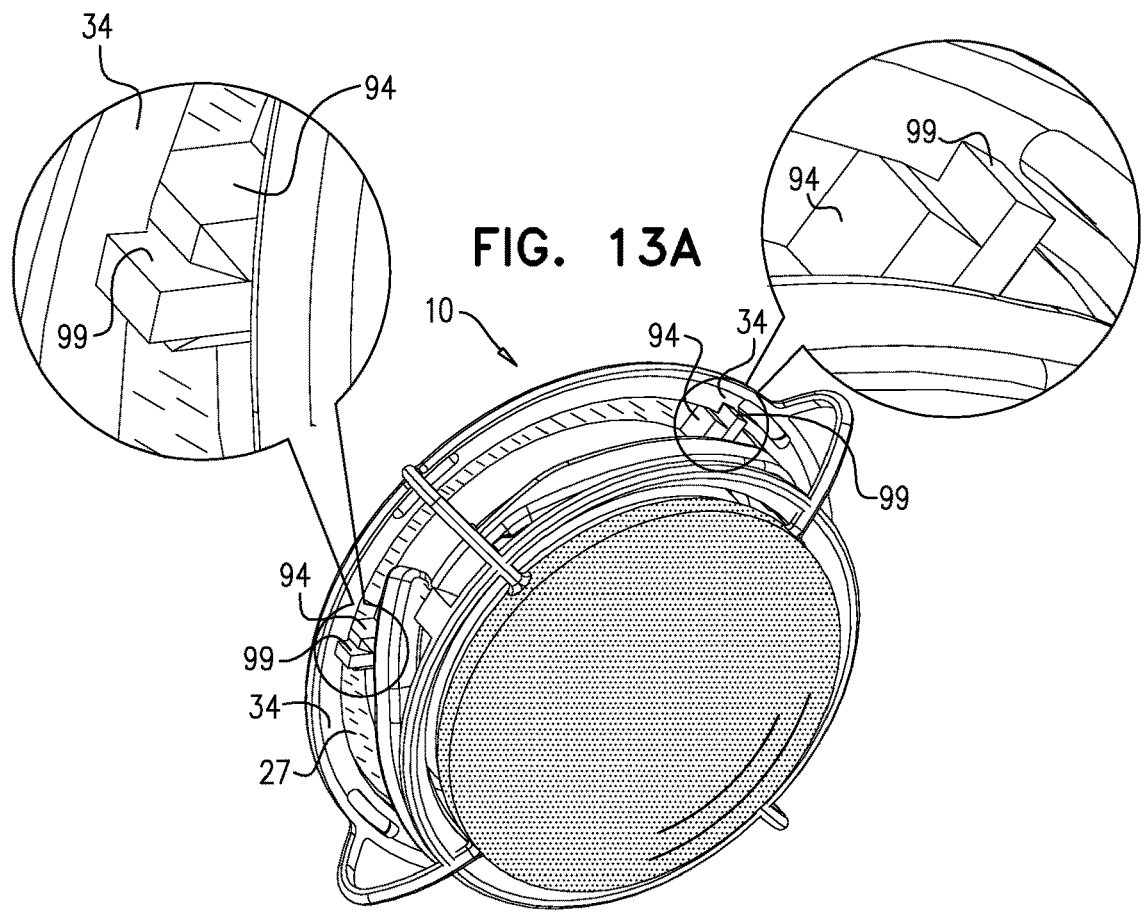
FIGS. 13A-B are schematic illustrations of the lens implant of FIGS. 1A-3B, in accordance with an application of the present invention.
Figure 13B:
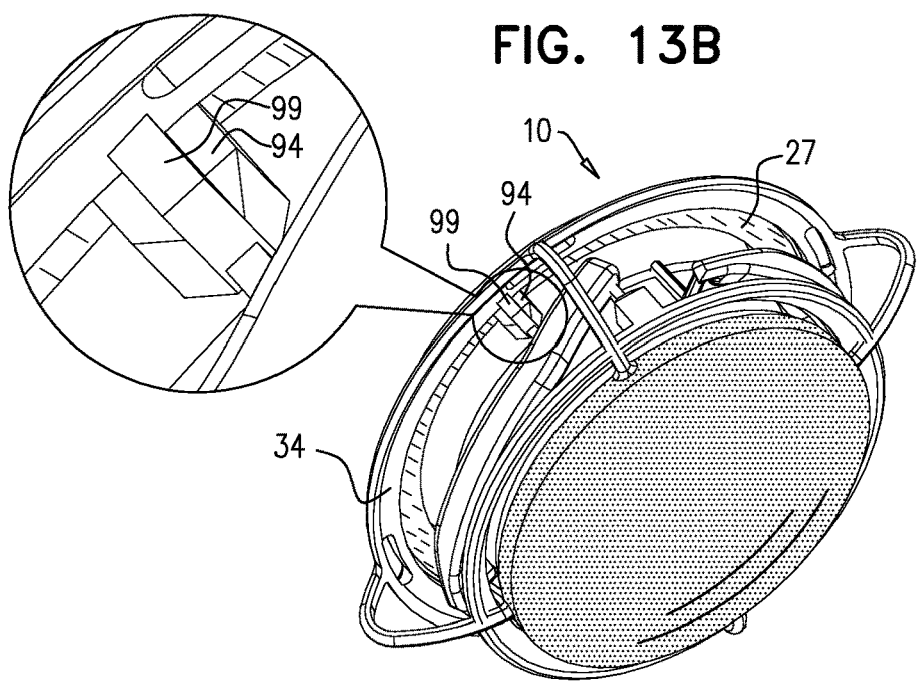

Reference is now made to FIGS. 13A-B, which are schematic illustrations of lens implant 10, in accordance with an application of the present invention. In some applications, inner anterior ring 27 is shaped so as to define one or more anterior inner rim extensions 99 which extend outwardly beyond the rest of the anterior inner rim. For example, anterior posts 94 of inner anterior ring 27 may be shaped so as to define the anterior inner rim extensions, as shown in the figures. For some applications, as shown, anterior inner rim extensions 99 are shaped as small tabs or posts. Anterior inner rim extensions 99 provide inner anterior ring 27 with an outer circumference that is greater than that of outer anterior ring 34 at at least some circumferential locations. As a result, when levered complex 14 and haptic complex 16 are assembled, as described hereinabove with reference to FIGS. 3A-B, extensions 99 of inner anterior ring 27 are in contact with and push against outer anterior ring 34 and prevent inner anterior ring 27 from moving to a more anterior position than outer anterior ring 34. Thus inner anterior ring 27 pushes only against outer anterior ring 34, but not against natural capsular bag 12, while outer anterior ring 34 pushes against the natural capsular bag. The larger outer diameter of outer anterior ring 34 reduces the risk of tearing the capsular bag. Typically, each of anterior inner rim extensions 99 extends outwardly beyond the rest of inner anterior ring 27 by at least 100 microns, no more than 500 microns, and/or between 100 and 500 microns.

Additional views of anterior inner rim extensions 99 are provided in a number of the figures, including FIGS. 5C-D, 9D, 10A-B, and 14A-C.

Figure 14A:
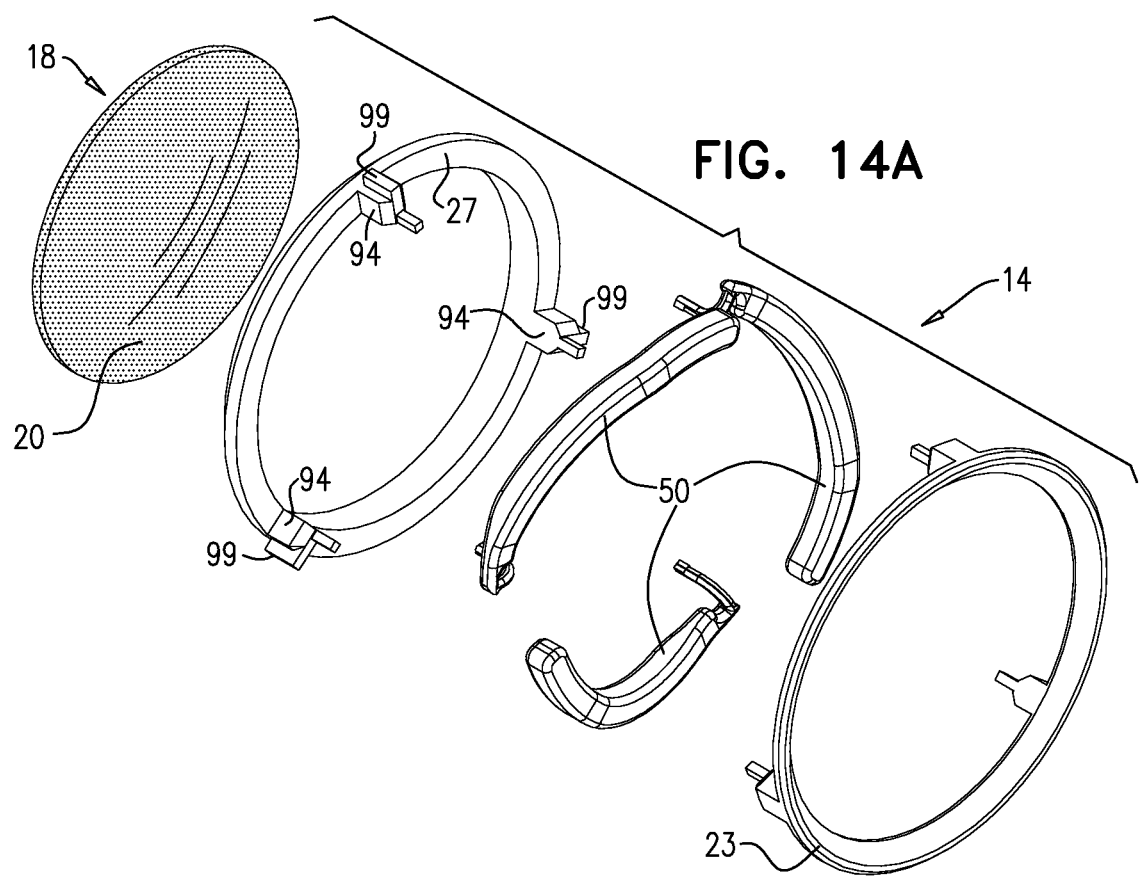
FIGS. 14A-C are schematic illustrations of a levered complex of the lens implant of FIGS. 1A-3B, in accordance with an application of the present invention.
Figure 14B:
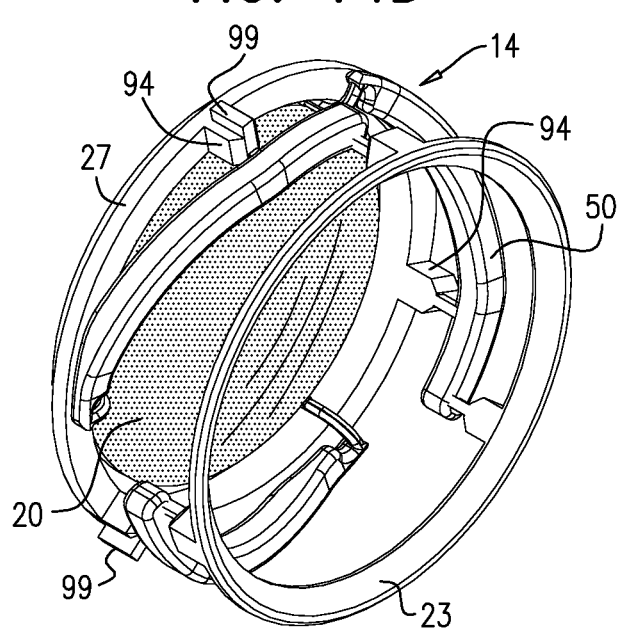
Figure 14C:
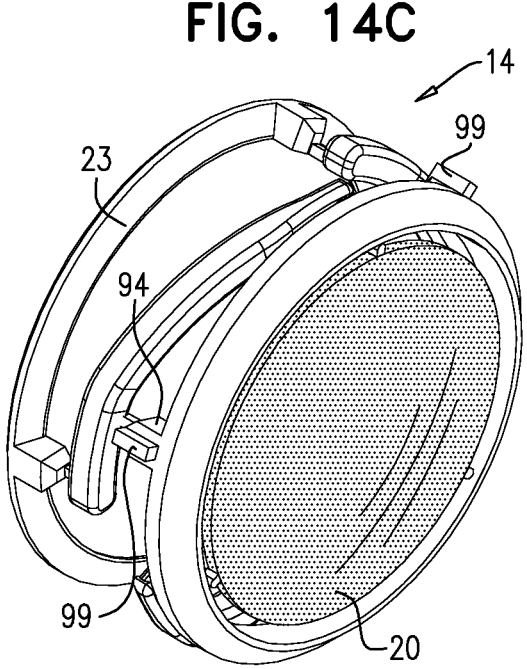

Reference is now made to FIGS. 14A-C, which are schematic illustrations of levered complex 14, in accordance with an application of the present invention. FIG. 14A separately shows components of levered complex 14. (In actual practice, these components are typically manufactured as a single element, rather than manufactured separately and coupled together.)

Figure 15A:
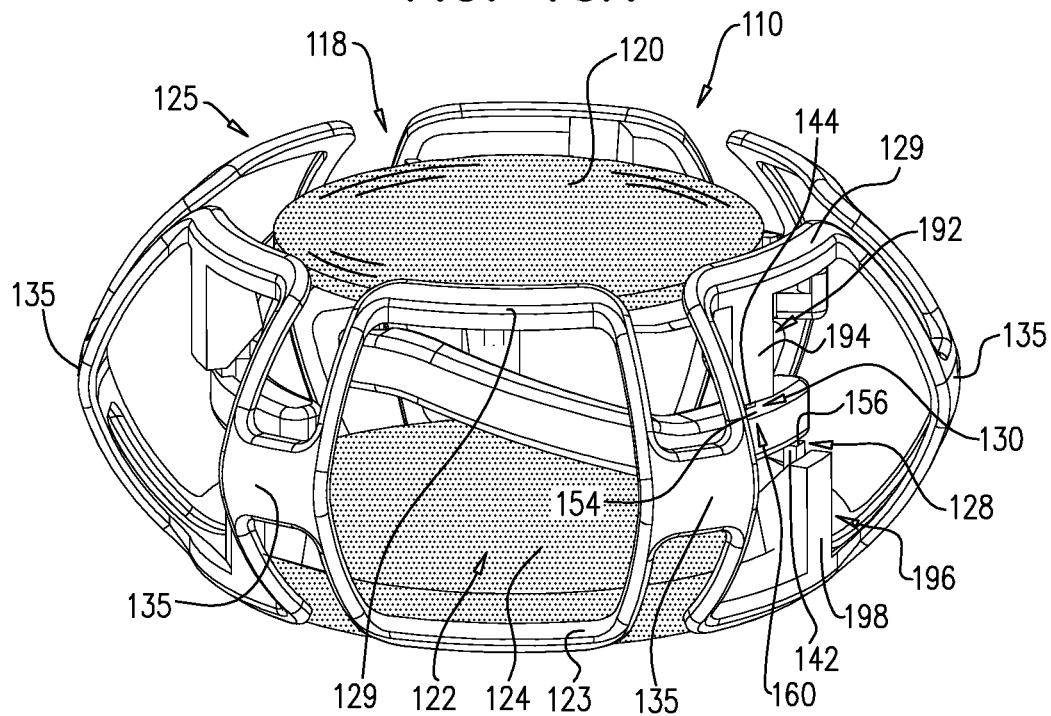
FIGS. 15A-B are schematic illustrations of a single-piece lens implant, in accordance with an application of the present invention.
Figure 15B:
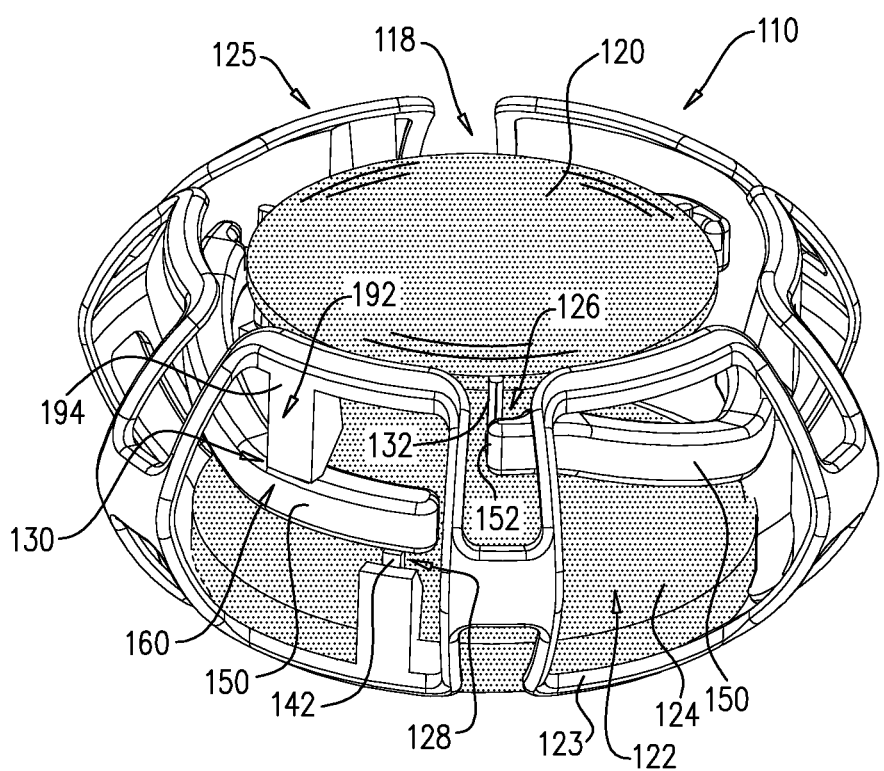

Reference is now made to FIGS. 15A-B, which are schematic illustrations of a single-piece lens implant 110, in accordance with an application of the present invention. Except as described below, lens implant 110 is similar to, and has the features of, and functions in accordance with the same principles as, lens implant 10, described hereinabove with reference to FIGS. 1A-14C. Lens implant 110 is implanted as a single piece, rather than being assembled in situ. Lens implant 110 is shown in FIGS. 15A-B in a fully-accommodated state. Lens implant 110 is configured to assume a continuous range of accommodation between the fully-accommodated state and a fully-unaccommodated state (not shown, but similar to the fully-unaccommodated state of lens implant 10, mutatis *mutandis*).

Lens implant 110 comprises (a) an anterior floating lens unit 118, which comprises an anterior lens 120, and (b) a posterior lens unit 122, which comprises a posterior lens 124, and, typically, a posterior lens rim 123, which may be circumferentially non-contiguous (as shown), or circumferentially contiguous like posterior lens rim 23 of lens implant 10 (configuration not shown in FIGS. 15A-B). (Each of lens units 118 and 122 may comprise one or more additional optical elements, such as described hereinabove regarding lens units 18 and 22. For some applications, anterior lens 120 is the only optical element of anterior floating lens unit 118, and/or posterior lens 124 is the only optical element of posterior lens unit 122.) Posterior lens unit 122 remains generally motionless with respect to the posterior portion of the natural capsular bag of the eye during accommodation of the lens implant. The lens implant is configured such that anterior floating lens unit 118 moves with respect to posterior lens unit 122 in response to the natural accommodation mechanism of the eye, as described hereinabove regarding lens implant 10.

Lens implant 110 further comprises an anterior rim complex 125 disposed such that anterior floating lens unit 118 is movable toward and away from the anterior rim complex 125, in an anterior-posterior direction. Anterior rim complex 125 comprises an anterior ring 129, which functions similar to the combination of inner and outer anterior rings 27 and 34 of lens implant 10. Anterior ring 129 may be circumferentially non-contiguous (as shown), or circumferentially contiguous like inner and outer anterior rings 27 and 34 of lens implant 10 (configuration not shown in FIGS. 15A-B). As the width (in the anterior-posterior direction) of the capsular bag changes, anterior rim complex 125 moves with respect to posterior lens unit 122, thereby changing the distance therebetween.

Lens implant 110 further comprises one or more levers 150, which are connected to anterior floating lens unit 118, anterior rim complex 125, and posterior lens unit 122 by respective links 126, 128, and 130. For example, lens implant 110 may comprise two, three (as shown in the figures), four, five, or six levers 150, and, typically, a corresponding number of each of links 126, links 128, and links 130. Typically, levers 150 are oriented predominantly horizontally, for example with the parameters described hereinabove with reference to FIGS. 1A-B and 2A-B regarding the predominantly horizontal orientation of levers 150.

Levers 150 are configured to magnify the relatively small change in the distance between anterior rim complex 125 and posterior lens unit 122, in order to move anterior floating lens unit 118 by a greater distance with respect to posterior lens unit 122. In other words, lens implant 110 is configured such that levers 150 move anterior floating lens unit 118 by a first anterior-posterior distance with respect to posterior lens unit 122 when anterior rim complex 125 moves a second anterior-posterior distance with respect to posterior lens unit 122, which first distance is greater than the second distance. Because of this distance magnification, the lens implant provides a high level of accommodation that mimics that of the natural eye. Typically, the first distance is at least 1.4 times the second distance, i.e., the lever provides a gain of at least 1.4. For example, the first distance may be at least 1.5 (e.g., at least 1.8, such as between 1.8 and 3) times the second distance. Anterior floating lens unit 118 typically shifts at least 1 mm between the fully-unaccommodated and fully-accommodated states.

For some applications, lens implant 110 is manufactured as single piece (such as by injection molding), and typically comprises a single material, such as silicone, acrylic, or Poly(methyl methacrylate) (PMMA). For some applications, lenses 120 and 124 and the other components of lens implant 110 comprise the same material (lenses 120 and 124 function as lenses because of the shapes thereof). Alternatively, one or more components of lens implant 110 are separately formed and coupled together during manufacture. For some applications, the material of lens implant 110 has a hardness of between 20 and 50 Shore A. Thus, all components of lens implant 110 are typically flexible. Typically, all of the rings and lenses of lens implant 110 are concentric.

Lens implant 110 further comprises one or more haptics 135, which couple anterior ring 129 to posterior lens unit 122. Haptics 135 provide a variable anterior-posterior distance between anterior ring 129 and posterior lens unit 122, and help position lens implant 110 properly in natural capsular bag 12. Typically, lever 150 is not coupled to any of haptics 135.

As mentioned above, lens implant 110 comprises a plurality of links 126, 128, and 130. More particularly, lens implant 110 comprises:

one or more anterior lens links 126, which comprise respective anterior lens jointed elements 132;
one or more posterior lens links 128, which comprise respective posterior lens jointed elements 142; and
one or more anterior rim links 130, which comprise respective anterior rim jointed elements 144.

For some applications, each of posterior lens links 128 comprises exactly one posterior lens jointed element 142. Alternatively or additionally, for some applications, each of anterior rim links 130 comprises exactly one anterior rim jointed element 144. Further alternatively or additionally, for some applications, each of anterior lens links 126 comprises exactly one anterior lens jointed element 132. Typically, anterior rim complex 125 is not itself jointed, and/or posterior lens unit 122 is not itself jointed.

Lever 150 is connected:
at a first longitudinal site 152 along lever 150, to anterior floating lens unit 118 by anterior lens link 126,
at a second longitudinal site 154 along lever 150, to anterior rim complex 125 by anterior rim link 130, and
at a third longitudinal site 156 along lever 150, to posterior lens unit 122 by posterior lens link 128.

Second longitudinal site 154 is longitudinally between first and third longitudinal sites 152 and 156 along lever 150, such that second longitudinal site 154 serves as a fulcrum 160 for lever 150.

Jointed elements 132, 142, and 144 function and are configured in the same manner as described hereinabove regarding jointed elements 32, 42, and 44 of lens implant 10. Jointed elements 132, 142, and 144 typically have the same dimensions as jointed elements 32, 42, and 44 of lens implant 10, as described hereinabove.

Anterior rim links 130 are connected to anterior rim complex 125 at respective anterior-rim-complex-connection sites of anterior rim complex 125. Anterior lens links 126 are connected to anterior floating lens unit 118 at respective anterior-lens-complex-connection sites of anterior floating lens unit 118. Posterior lens links 128 are connected to posterior lens unit 122 at respective posterior-lens-complex-connection sites of posterior lens unit 122. Typically, as lens implant 110 transitions between the fully-accommodated and the fully-unaccommodated states:
a location of each of second longitudinal sites 154 relative to anterior rim complex 125 changes by less than 500 microns, e.g., less than 200 microns;
a location of each of first longitudinal sites 152 relative to anterior floating lens unit 118 changes by less than 500 microns, e.g., less than 200 microns; and/or
a location of each of third longitudinal sites 156 relative to posterior lens unit 122 changes by less than 500) microns, e.g., less than 200 microns.

Lens implant 110 is typically configured such that levers 150 do not move, or move only slightly, radially toward or away from a central optical axis of anterior lens 120, as lens implant 110 transitions between the fully-accommodated and the fully-unaccommodated states of lens implant 110, such as described hereinabove regarding lens implant 10 (including the described changes in distance). For some applications, the posterior-lens-complex-connection and the anterior-rim-complex-connection sites of each respective lever 150 are circumferentially offset from each other with respect to the central optical axis, such as by at least 15 degrees (e.g., at least 20 degrees) around the central optical axis.

For some applications, anterior floating lens unit 118 further comprises one or more attachment elements, and the lever is connected to the attachment elements by respective anterior lens links 126 (configuration not shown). For example, the attachment elements may comprise respective anterior lens posts, and the lever is connected to the anterior lens posts by respective anterior lens links 126 (configuration not shown). Alternatively, the one or more attachment elements may comprise an anterior lens rim, and the lever is connected to the anterior lens rim by the anterior lens links (configuration not shown).

For some applications, anterior rim complex 125 (e.g., anterior ring 129 thereof) further comprises one or more attachment elements 192, and lever 150 is connected to the attachment elements by respective anterior rim links 130. For example, attachment elements 192 may comprise respective anterior posts 194, and lever 150 is connected to anterior posts 194 by respective anterior rim links 130. Optionally, each of anterior posts 194 is oriented within 5 degrees of parallel to the anterior-posterior direction, such as parallel to the anterior-posterior direction.

For some applications, posterior lens unit 122 further comprises one or more attachment elements 196, and lever 150 is connected to the attachment elements by respective posterior lens links 128. For example, attachment elements 196 may comprise respective posterior posts 198, and lever 150 is connected to posterior posts 198 by respective posterior lens links 128. Alternatively or additionally, the one or more attachment elements may comprise posterior lens rim 123, and lever 150 is connected to posterior lens rim 123 by posterior lens links 128. For applications in which the one or more attachment elements 196 comprise both posterior posts 198 and posterior lens rim 123, posterior posts 198 are connected to posterior lens rim 123, and lever 150 is connected to posterior posts 198 by respective posterior lens links 128.

Typically, second longitudinal site 154 is closer to third longitudinal site 156 than to first longitudinal site 152. For some applications, a first distance between second longitudinal site 154 and third longitudinal site 156 is less than 70/o of a second distance between first longitudinal site 152 and second longitudinal site 154; such a location of anterior rim link 130 along lever 150 typically provides a gain of at least 1.4. For some applications, the first distance is less than 30% of the second distance, which typically provides a gain of at least 3.3. For some applications, the first distance is at least 500 microns. Typically, the first distance is at least 10%, typically at least 33%, of the second distance. Typically, first longitudinal site 152 is near a first end of lever 150, such as within 10% of a total length of lever 150, measured along a central longitudinal axis, from the first end.

For some applications, each of levers 150, at each of all longitudinal locations therealong longitudinally between first and third longitudinal sites 152 and 156, is shaped so as to have one of the respective shape features of lever 50 described hereinabove with reference to FIG. 7.

FIGS. 16A-B and 17A-B are schematic illustrations of an accommodative intraocular lens implant 210, in accordance with an application of the present invention. FIGS. 16A-B are isometric views of the lens implant. FIGS. 17A-B are side views showing the lens implant implanted in natural capsular bag 12 of the eye. FIGS. 16A and 17A show lens implant 210 in a fully-unaccommodated state, while FIGS. 16B and 17B show the lens implant in a fully-accommodated state. Although only these two states are shown in these and the other figures, lens implant 210 is configured to assume a continuous range of accommodation between the fully-unaccommodated state and the fully-accommodated state. The fully-accommodated state provides near vision, the fully-unaccommodated state provides distance vision, and partially-accommodated states therebetween provide intermediate vision. The lens implant is configured to reach the fully-accommodated state responsively to the natural accommodation mechanism of the eye, without the need for external power.

Lens implant 210 comprises (a) an anterior floating lens unit 218, which comprises an anterior lens 220, and (b) a posterior lens unit 222, which comprises a posterior lens 224. Posterior lens unit 222 remains generally motionless with respect to the posterior portion of natural capsular bag 12 of the eye during accommodation of the lens implant. The lens implant is configured such that anterior floating lens unit 218 moves with respect to posterior lens unit 222 in response to the natural accommodation mechanism of the eye, which changes the shape of natural capsular bag 12, as shown in FIGS. 17A-B. In the fully-unaccommodated state shown in FIG. 17A, the ciliary muscle is relaxed and the zonular fibers are therefore tensed, causing the capsular bag to assume a relatively narrow width (in an anterior-posterior direction) and relatively large diameter. Thus shaped, the capsular bag squeezes the lens implant in the anterior-posterior direction. In contrast, in the fully-accommodated state shown in FIG. 17B, the ciliary muscle contracts, thereby releasing the tension of the zonular fibers on the capsular bag, causing the capsular bag to assume a relatively large width and relative small diameter. This shape of the capsular bag allows the lens implant to expand in the anterior-posterior direction. (As used herein, the diameter of the capsular bag means the greatest diameter of the capsular bag when viewed from its posterior aspect.)

Lens implant 210 further comprises an anterior rim complex 225 disposed such that anterior floating lens unit 218 is movable toward and away from anterior rim complex 225, in the anterior-posterior direction. Anterior rim complex 225 comprises an anterior ring 227 (optionally, only anterior ring 227). As the width (in the anterior-posterior direction) of the capsular bag changes, anterior rim complex 225 moves with respect to posterior lens unit 222, thereby changing the distance between anterior rim complex 225 and posterior lens unit 222.

As described in detail hereinbelow with reference to FIGS. 19A-B, lens implant 210 further comprises one or more levers 250, which are connected to anterior floating lens unit 218 and anterior rim complex 225, for example by respective anterior lens links 226 and anterior rim links 230 (shown more clearly in FIGS. 19A-B). Levers 250 are also in jointed connection with posterior lens unit 222 (shown more clearly in FIGS. 19A-B). Typically, lens implant 210 comprises at least six levers (e.g., exactly six levers), such as more than six levers, e.g., at least eight levers (e.g., exactly eight levers, as shown in the figures, exactly ten levers, or exactly 12 levers), and, typically, a corresponding number of each of links 226 and links 230. For some applications, as shown in the figures, levers 250 are evenly circumferentially distributed around lens implant 210.

Levers 250 are configured to magnify the relatively small change in the distance between anterior rim complex 225 and posterior lens unit 222, in order to move anterior floating lens unit 218 by a greater distance with respect to posterior lens unit 222. In other words, lens implant 210 is configured such that levers 250 move anterior floating lens unit 218 by a first anterior-posterior distance with respect to posterior lens unit 222 when anterior rim complex 225 moves a second anterior-posterior distance with respect to posterior lens unit 222, which first distance is greater than the second distance. Because of this distance magnification, the lens implant provides a high level of accommodation that mimics that of the natural eye. Typically, the first distance is at least 1.4 times the second distance, i.e., levers 250 provide a gain of at least 1.4. For example, the first distance may be at least 1.5 (e.g., at least 1.8, such as between 1.8 and 4, such as 3) times the second distance.

The anterior and posterior movement of anterior floating lens unit 218 changes the distance between the anterior and posterior lens units, thereby adjusting the focal length of the lens implant. In the fully-accommodated state, which provides near vision, lens implant 210 is relatively wide (in the anterior-posterior direction), with a large separation between the anterior and posterior lens units, creating a large free space between the complexes. In the fully-unaccommodated state, which provides distance vision, the implant is relatively narrow, with a small separation between anterior and posterior complexes. Anterior floating lens unit 218 typically shifts at least 1 mm between the fully-unaccommodated and fully-accommodated states. Typical movement of the anterior lens relative to the posterior lens is between 0.5 and 2.0 mm, such as between 1 and 1.5 mm, as the lens implant transitions between the fully-unaccommodated and fully-accommodated states.

Anterior floating lens unit 218 moves within an interior space of lens implant 210, which is typically open to the natural fluid within the eye. The anterior floating lens unit is configured to create minimum drag during movement, while maintaining the optical performance of the combined lens structure. For example, the anterior floating lens unit may have a smooth shape, and/or may be coated with a hydrophobic coating such as silicone. Typically, the anterior and posterior lens units are configured to together create an optical structure having a total power that varies between +15D and +25D, as selected by the physician implanting the lens implant.

As mentioned above, anterior floating lens unit 218 comprises anterior lens 220, and posterior lens unit 222 comprises posterior lens 224. Each of lens units 218 and 222 may comprise one or more additional optical elements, such as additional lenses (e.g., convex lenses, concave lenses, biconvex lenses, biconcave lenses, spherical lenses, aspheric lenses, and/or astigmatic lenses), fixed power optics, deformable optics, aberration free optics, doublets, triplets, filtered optics, or combinations of these lenses, as is known in the optical arts. For some applications, anterior lens 220 is the only optical element of anterior floating lens unit 218, and/or posterior lens 224 is the only optical element of posterior lens unit 222. For some applications, one or more of lens units 218 and 222 are attached to the implant during manufacture. Alternatively or additionally, one or more of the lens units may be attached by a healthcare worker either prior to or during the implantation procedure, such as to provide the lens unit most appropriate for the particular patient.

Reference is now made to FIGS. 18A and 18B, which are schematic illustrations of a two-part assembly configuration of lens implant 210, in disassembled and assembled states, respectively, in accordance with an application of the present invention. In this configuration, lens implant 210 comprises two components that are initially separate from each other, and are typically assembled together in situ during implantation of the lens implant: (1) posterior lens unit 222 and (2) an anterior component 217. Both components are shown in the fully-accommodated state in both FIGS. 18A and 18B. In this configuration, posterior lens unit 222 and anterior component 217 are distinct from each other and not permanently fixed to each other, and are shaped so as to be assemblable together (e.g., snapped together) in situ in a human eye.

Posterior lens unit 222 typically has an inner surface 270 that defines an interface region 272, such as described hereinbelow with reference to FIG. 20D. When posterior lens unit 222 and anterior component 217 are assembled together as shown in FIG. 18B, posterior lens unit 222 and anterior component 217 contact each other at one or more interfaces 219 (labeled in FIGS. 19A-B), typically at interface region 272 of posterior lens unit 222. Typically, when posterior lens unit 222 and anterior component 217 are assembled together, levers 250 are pivotable about the one or more interfaces 219. For some applications, the one or more interfaces 219 comprise exactly one circumferential interface 219, and posterior lens unit 222 and anterior component 217 contact each other at the exactly one circumferential interface 219 when posterior lens unit 222 and anterior component 217 are assembled together.

Reference is now made to FIGS. 19A-B, which are schematic cross-sectional illustrations of lens implant 210 in the fully-unaccommodated state and fully-accommodated state, respectively, in accordance with an application of the present invention. For some applications, lens implant 210 (typically anterior component 217 thereof) further comprises a circumferential rim 260. Levers 250:
- at respective first longitudinal sites 252 along levers 250, are in jointed connection with anterior floating lens unit 218, and
- at respective third longitudinal sites 256 along levers 250, are (a) fixed to circumferential rim 260 at respective, different circumferential locations 262 around rim 260 (labeled in FIG. 21A), and (b) in jointed connection with posterior lens unit 222.

Circumferential rim 260 maintains the circumferential positions of third longitudinal sites 256 of levers 250, and helps facilitate the assembly together of anterior component 217 and posterior lens unit 222.

For some applications, circumferential rim 260 contacts posterior lens unit 222 at the one or more interfaces 219 when posterior lens unit 222 and anterior components 217 are assembled together. Typically, circumferential rim 260 is pivotable about the one or more interfaces 219 when posterior lens unit 222 and anterior component 217 are assembled together. For some applications, the one or more interfaces 219 comprise exactly one circumferential interface 219, and circumferential rim 260 contacts posterior lens unit 222 at the exactly one circumferential interface 219 when posterior lens unit 222 and anterior component 217 are assembled together.

Alternatively, lens implant 210 is manufactured as a single piece, or is assembled immediately prior to implantation, rather than assembled in situ.

For some applications, the assembled resting state of lens implant 210 (i.e., the unconstrained as-manufactured slate before implantation into an eye, but after assembly) is the fully-accommodated state of lens implant 210.

Alternatively, for some applications, the assembled resting state of lens implant 210 is beyond the fully-accommodated state of lens implant 210, i.e., is an over-accommodated state. In other words, when in the assembled resting state, lens implant 210 is wider in the anterior-posterior direction (e.g., at least 25%, such as at least 50% wider) than the maximum anterior-posterior width of natural capsular bag 12 when the eye is fully accommodated. As a result, the lens implant presses the lens capsule open even when the lens implant is fully accommodated, thereby keeping the zonules in tension and pre-tensioning the zonules when the eye is fully accommodated. Such pre-tensioning generally causes lens implant 210 to remain in a radially central position, even without haptics.

For some applications, a greatest possible anterior-posterior stroke distance of anterior rim complex 225 between the resting, unconstrained (including unconstrained by the natural capsular bag) over-accommodated state and the fully-unaccommodated state is greater than (e.g., at least 25% greater than, such as at least 50% greater than) a greatest change in anterior-posterior width of the natural capsular bag between fully-accommodated and fully-unaccommodated states of the natural capsular bag. For example, in a typical adult human eye, the greatest change in anterior-posterior width of the natural capsular bag between fully-accommodated and fully-unaccommodated states is generally about 0.7 mm. Therefore, for some applications, the greatest anterior-posterior stroke distance of anterior rim complex 225 between the resting, unconstrained over-accommodated state and the fully-unaccommodated state is greater than 0.7 mm, e.g., at least 0.875 mm, such as at least 1.05 mm.

As the anterior-posterior width of the natural capsular bag changes, anterior rim complex 225 moves with respect to posterior lens unit 222, thereby changing the distance between anterior rim complex 225 and posterior lens unit 222.

Reference is made to FIGS. 18A-B and 19A-B. For some applications, anterior component 217 comprises the following components, each of which is described in detail hereinbelow (and perhaps can be seen most clearly in FIG. 19A):
- anterior floating lens unit 218, which comprises anterior lens 220;
- anterior rim complex 225, which comprises anterior ring 227;
- levers 250;
- optionally, anterior lens links 226; and
- optionally, anterior rim links 230.

For some applications, anterior component 217 is manufactured as single piece (such as by injection molding), and typically comprises a single material, such as silicone, acrylic, or Poly(methyl methacrylate) (PMMA). For some applications, anterior lens 220 and the other components of anterior component 217 comprise the same material (anterior lens 220 functions as a lens because of its shape). Alternatively, one or more components of anterior component 217 are separately formed and coupled together during manufacture. Likewise, for some applications, posterior lens unit 222 is manufactured as single piece (such as by injection molding), and typically comprises a single material, such as silicone, acrylic, or Poly(methyl methacrylate) (PMMA). Alternatively, one or more components of posterior lens unit 222 are separately formed and coupled together during manufacture. For some applications, posterior lens 224 and the other components of posterior lens unit 222 comprise the same material (posterior lens 224 functions as a lens because of its shape). (Although transparent, lens 220 and 224 are shaded in the figures for clarity of illustration; as mentioned above, the lenses may comprise the same material as the other components of the lens implant.)

For some applications, the material of posterior lens unit 222 has a hardness of between 20 and 60 Shore A, and the material of anterior component 217 has a hardness of between 20 and 60 Shore A. Thus, all components of lens implant 210 are typically flexible.

As mentioned above, posterior lens unit 222 and anterior component 217 are typically separately inserted into natural capsular bag 12 in a two-step insertion procedure, and assembled together in situ in the capsular bag. Posterior lens unit 222 is first inserted, and thereafter anterior component 217 is inserted. This two-step insertion procedure generally allows the use of a smaller incision than is necessary for a one-step insertion procedure of a single-piece implant. Typically, upon assembly, all of the rings and lenses of lens implant 210 are concentric.

For some applications, posterior lens unit 222 and anterior component 217 are preloaded into a single introducer, and separately introduced into the capsular bag from the single introducer, for example using techniques described hereinbelow. For other applications, posterior lens unit 222 and anterior component 217 are preloaded into separate first and second introducer tubes that are distinct and separate from each other, such as described hereinbelow. In either case, anterior component may optionally be preloaded into an introducer tube using the techniques described hereinbelow with reference to FIG. 24.

For some applications, for each individual patient a healthcare worker selects one of a plurality of available posterior lens units 222 having different respective optical properties, and/or selects one of a plurality of available anterior components 217 having different respective optical properties.

For some applications, posterior lens unit 222 is inserted, and reshapes natural capsular bag 12. The vision of the patient is then measured. Responsively to the measured vision, a healthcare worker selects one of a plurality of available anterior floating lens units 218 having the most appropriate optical properties for the patient. An anterior component 217 having the selected anterior floating lens unit 218 is inserted into posterior lens unit 222. This selection procedure may provide better vision for the patient.

For some applications, for treating astigmatism, both anterior floating lens unit 218 and posterior lens unit 222 have some cylinder for treating the astigmatism. During the two-stage implantation procedure, a healthcare worker adjusts a relative angular orientation of the two lens units in order to treat the patient's astigmatism. This combination of cylinders between the two lens units allows treatment of a variety of astigmatisms with fewer different lens implants than would be necessary if separate lens implants were to be provided for each cylinder power. More generally, for some applications, anterior floating lens unit 218 and/or posterior lens unit 222 are not rotationally symmetrical. For some applications, a healthcare worker adjusts the effective diopter of lens implant 210, by rotating the lens units with respect to each other.

As mentioned above, during the implantation procedure, posterior lens unit 222 is first inserted into natural capsular bag 12. Subsequently, anterior component 217 is inserted into the capsular bag. Posterior lens unit 222 is configured to receive and center anterior component 217. After insertion, anterior ring 227 of anterior rim complex 225 moves in response to natural motion of the anterior portion of natural capsular bag 12. Typically, anterior ring 227 is configured to come in contact with the natural capsular bag.

Reference is still made to FIGS. 19A-B. Levers 250 are in jointed connection with:
  anterior floating lens unit 218 at respective first longitudinal sites 252 along levers 250;
  anterior rim complex 225 at respective second longitudinal sites 254 along levers 250; and
  posterior lens unit 222 at respective third longitudinal sites 256 along levers 250.

Levers 250 are arranged to move anterior floating lens unit 218 toward and away from anterior rim complex 225, in an anterior-posterior direction.

As mentioned above with reference to FIGS. 16A-B and 17A-B, for some applications, lens implant 210 comprises a plurality of links 226 and 230. More particularly, for some applications, lens implant 210 comprises:
  a plurality of anterior lens links 226, which typically comprise respective anterior lens jointed elements 232 (which are described in greater detail hereinbelow); and
  a plurality of anterior rim links 230, which typically comprise respective anterior rim jointed elements 244 (which are described in greater detail hereinbelow).

For some applications, each of anterior rim links 230 comprises exactly one anterior rim jointed element 244. Further alternatively or additionally, for some applications, each of anterior lens links 226 comprises exactly one anterior lens jointed element 232. Typically, anterior rim complex 225 is not itself jointed, and/or posterior lens unit 222 is not itself jointed.

For some applications, levers 250 are in the jointed connection:
  at the respective first longitudinal sites 252 along levers 250, with anterior floating lens unit 218 by the respective anterior lens links 226, and
  at the respective second longitudinal sites 254 along levers 250, with anterior rim complex 225 (typically with anterior ring 227 of anterior rim complex 225) by the respective anterior rim links 230.

In addition, each of levers 250, at a third longitudinal site 256 along lever 250, is in jointed connection with posterior lens unit 222. (The phrase "along" lever 250 is to be understood as including the ends of the lever; for example, third longitudinal site 256 may be at one end of the lever, as shown.)

For some applications, each third longitudinal site 256 is at an end-most site of the respective lever 250. For some applications, each of levers 250 is in jointed connection with posterior lens unit 222 at an end-most site of the lever 250, when posterior lens unit 222 and anterior component 217 are assembled together (either in situ, immediately prior to implantation, or during manufacture).

As used in the present application, including in the claims, a "lever" is a beam that is used to move an object at a first point by a force applied at a second point, and that pivots about a fulcrum at a third point. For each of levers 250, second longitudinal site 254 is longitudinally between first and third longitudinal sites 252 and 256 along lever 250, such that third longitudinal site 256 serves as a fulcrum 264 for lever 250. Thus, first longitudinal site 252, second longitudinal site 254, and third longitudinal site 256 correspond with the first, second, and third points, respectively, in the definition above.

Force is applied to second longitudinal site 254 by anterior rim complex 225, and, as a result, first longitudinal site 252 (and anterior floating lens unit 218) moves more than an anterior-posterior distance that second longitudinal site 254 (and anterior rim complex 225) moves, typically between 1.5 and 4 times the anterior-posterior distance that second longitudinal site 254 (and anterior rim complex 225) moves. For some applications, a distance between second and third longitudinal sites 254 and 256 is 0.6 mm, and a distance between first and third longitudinal sites 252 and 256 is 1.8 mm, providing a gain of 3. Typically, second longitudinal sites 254 are disposed radially inward from third longitudinal sites 256, respectively. Typically, first longitudinal sites 252 are disposed radially inward from second longitudinal sites 254 and third longitudinal sites 256, respectively. The levers, including the location of the fulcrum, are typically configured to provide a gain of at least 1.4, as described hereinabove with reference to FIGS. 16A-B and 17A-B.

Each of jointed elements 232 and 244 joins respective pairs of elements of lens implant 210 so as to permit relative motion (particularly rotational motion) between the joined elements. Anterior lens jointed elements 232 are typically configured (e.g., are sufficiently long, as described below) to allow a small amount of radial motion between levers 250 and anterior floating lens unit 218. For some applications, each of anterior lens jointed elements 232 is configured to allow first longitudinal site 252 along lever 250 to move radially between 100 and 250 microns (and/or no more than 5% of a radius of anterior lens 220) with respect to an anterior-lens-complex-connection site 284 of anterior floating lens unit 218, as lens implant 210 transitions between the fully-accommodated and the fully-unaccommodated states. (As used in the present application, including in the claims, transitioning between the fully-accommodated and the fully-unaccommodated states is to be understood as meaning making a transition that begins at the fully-accommodated state and continues all the way to the fully-unaccommodated state, or vice versa.) Anterior lens jointed elements 232 are shaped and sized to rotate slightly to absorb this radial motion. In some configurations, each of anterior lens jointed elements 232 comprises a small, relatively thin shaft, typically having a length of between 500 and 1000 microns. Typically, each of anterior jointed elements 232 has a cross-sectional area measured along the joined element perpendicular to a longitudinal axis of the jointed element that is less than 0.04 mm2, such as less than 0.03 mm2.

For some applications, anterior lens jointed elements 232 are slightly tilted sideways around central optical axis 290 (clockwise or counterclockwise) from parallel with a central optical axis 290 of anterior lens 220, e.g., by between 10 and 60 degrees (configuration not shown. This tilting may allow anterior lens jointed elements 232 to be longer than would otherwise be possible because of the anterior-posterior size constraints of the natural capsular bag. For some applications, a portion (e.g., half) of the anterior lens jointed elements 232 tilt clockwise, and the remainder tilt counterclockwise, to allow for the radial motion while limiting the propensity of posterior lens unit 222 to rotate.

Typically, anterior rim jointed elements 244 are configured to minimize non-rotational motion, such as radial motion, between second longitudinal sites 254 of levers 250 and their respective anterior-rim-complex-connection sites 282 to the extent possible given other design constraints. Likewise, the one or more interfaces 219 are configured to minimize non-rotational motion, such as radial motion, between third longitudinal sites 256 of levers 250 and respective posterior-lens-complex-connection sites 280 of posterior lens unit 222.

Levers 250 are more rigid than anterior lens jointed elements 232 and anterior rim jointed elements 244 (even though levers 250, anterior lens jointed elements 232, and anterior rim jointed elements 244 may all comprise the same material, as described above).

As used in the present application, including the claims, "radial" means in a direction toward or away from central optical axis 290 of anterior lens 220.

Anterior rim links 230 are connected to anterior rim complex 225 at respective anterior-rim-complex-connection sites 282 of anterior rim complex 225. Anterior lens links 226 are connected to anterior floating lens unit 218 at respective anterior-lens-complex-connection sites 284 of anterior floating lens unit 218.

Typically, as lens implant 210 transitions between the fully-accommodated and the fully-unaccommodated states:
  a location of each of second longitudinal sites 254 relative to anterior rim complex 225 changes by less than 500 microns, e.g., less than 200 microns, and/or by less than 50% of a distance between second longitudinal site 254 and its respective anterior-rim-complex-connection sites 282 when the lens implant is in the fully-accommodated state;
  a location of each of first longitudinal sites 252 relative to anterior floating lens unit 218 changes by less than 500 microns, e.g., less than 200 microns, and/or by less than 50% of a distance first longitudinal site 252 and its respective anterior-lens-complex-connection site 284 when the lens implant is in the fully-accommodated state; and/or
  a location of each of third longitudinal sites 256 relative to posterior lens unit 222 changes by less than 500 microns, e.g., less than 200 microns, and/or by less than 50% of a distance third longitudinal site 256 and its respective posterior-lens-complex-connection site 280 when the lens implant is in the fully-accommodated state.

Alternatively or additional, for some applications, during a change in distance between posterior lens unit 222 and anterior ring 227 during accommodation of lens implant 210:
  a location of each of second longitudinal sites 254 relative to anterior rim complex 225 changes by less than 50% of the change in distance between posterior lens unit 222 and anterior ring 227;
  a location of each of first longitudinal sites 252 relative to anterior floating lens unit 218 changes by less than 50% of the change in distance between posterior lens unit 222 and anterior ring 227; and/or
  a location of each of third longitudinal sites 256 relative to posterior lens unit 222 changes by less than 50/of the change in distance between posterior lens unit 222 and anterior ring 227.

Lens implant 210 is typically configured such that levers 250 do not move, or move only slightly, radially toward or away from central optical axis 290 of anterior lens 220, as lens implant 210 transitions between the fully-accommodated and the fully-unaccommodated states. For example, lens implant 210 may be configured such that, as lens implant 210 transitions between the fully-accommodated and the fully-unaccommodated states:
  a greatest change in distance between any portion of each of levers 250 and central optical axis 290 is less than 500 microns, e.g., less than 250 microns, and/or less than 10%, e.g., less than 5%, of a diameter of anterior lens 220;
  a change in distance between each of second longitudinal sites 254 and central optical axis 290 is less than 500 microns, e.g., less than 250 microns, and/or less than 10%, e.g., less than 5%, of the diameter of anterior lens 220; and/or
  a change in distance between each of third longitudinal sites 256 and central optical axis 290 is less than 500 microns, e.g., less than 250 microns, and/or less than 10%, e.g., less than 5%, of the diameter of anterior lens 220.

Figure 20A:
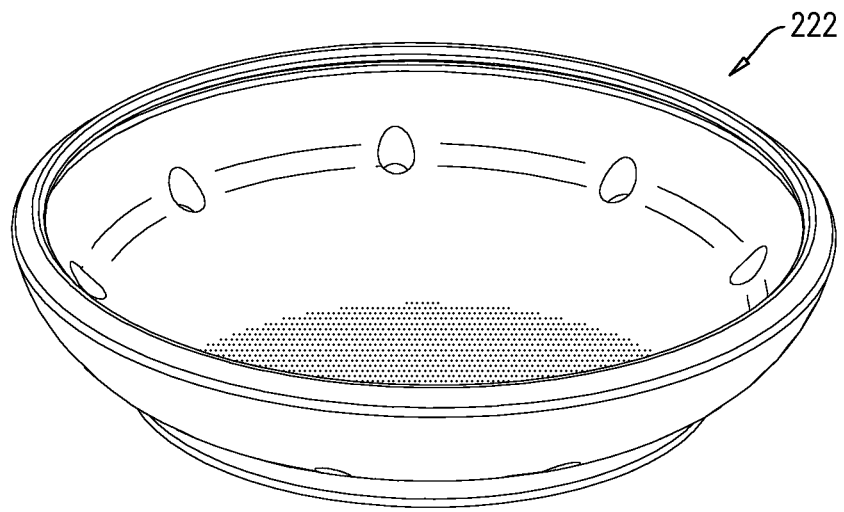
FIGS. 20A-D provide several views of a posterior lens unit of the lens implant of FIGS. 16A-B in a disassembled state, in accordance with an application of the present invention.
Figure 20B:
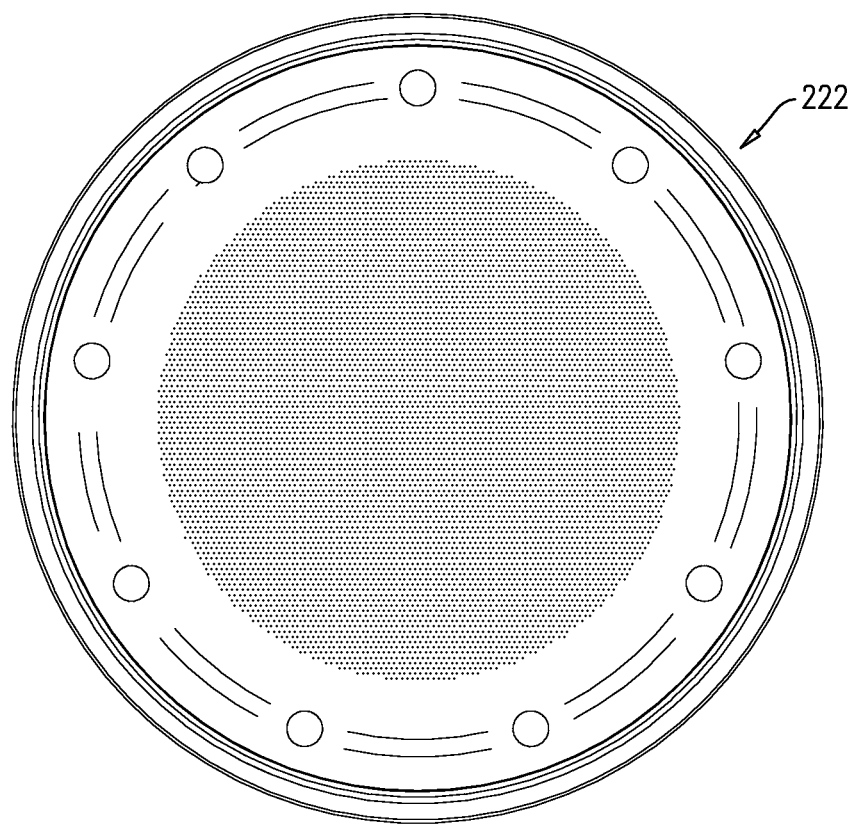
Figure 20C:
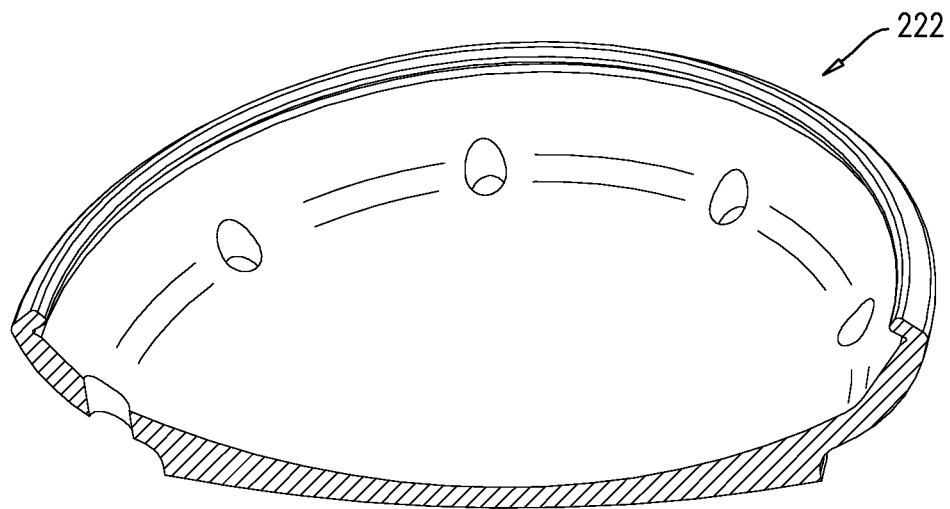
Figure 20D:
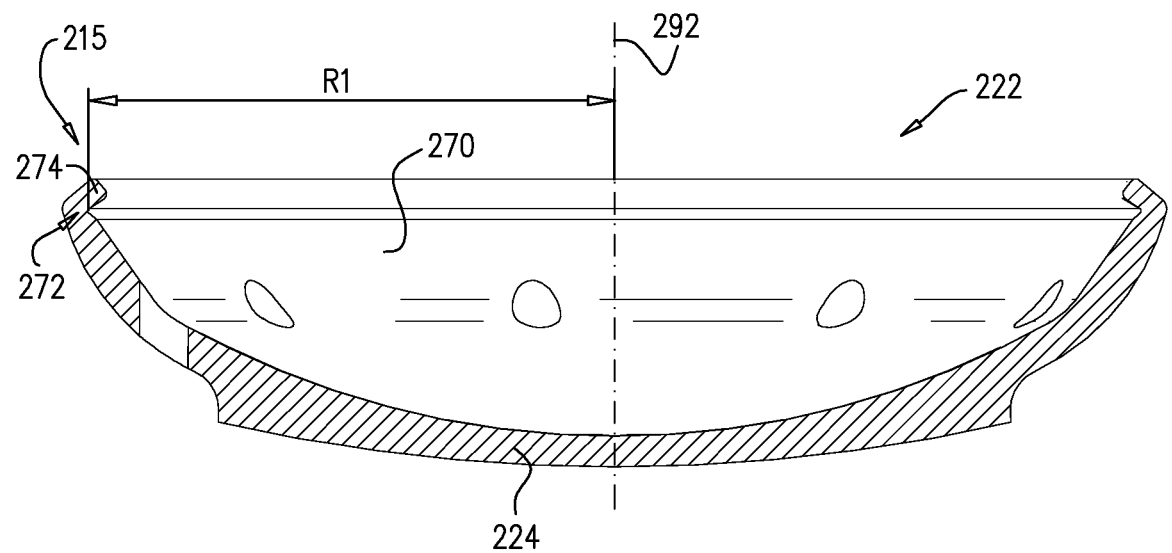

Reference is made to FIGS. 20A-D, which provide several views of posterior lens unit 222 of lens implant 210 in a disassembled state, in accordance with an application of the present invention. FIG. 20C-D are cross-sectional views.

For some applications, as labeled in FIG. 20D, posterior lens unit 222 is concave (e.g., bowl-shaped) and has inner surface 270 that defines interface region 272, a portion of which defines a local maximum radius R1 from a central optical axis 292 of posterior lens 224, optionally, a maximum radius from central optical axis 292. (Central optical axis 292 of posterior lens 224 is coaxial with central optical axis 290 of anterior lens 220 when posterior lens unit 222 and anterior component 217 are assembled together (either in situ, immediately prior to implantation, or during manufacture).) Typically, circumferential rim 260 is in jointed connection with interface region 272 of inner surface 270. For some applications, posterior lens unit 222 is shaped so as to define a lip 274 anteriorly adjacent to the portion of interface region 272. Lip 274 is shaped so as to inhibit anterior motion of circumferential rim 260. Typically, inner surface 270 slopes smoothly toward interface region 272.

Figure 21A:
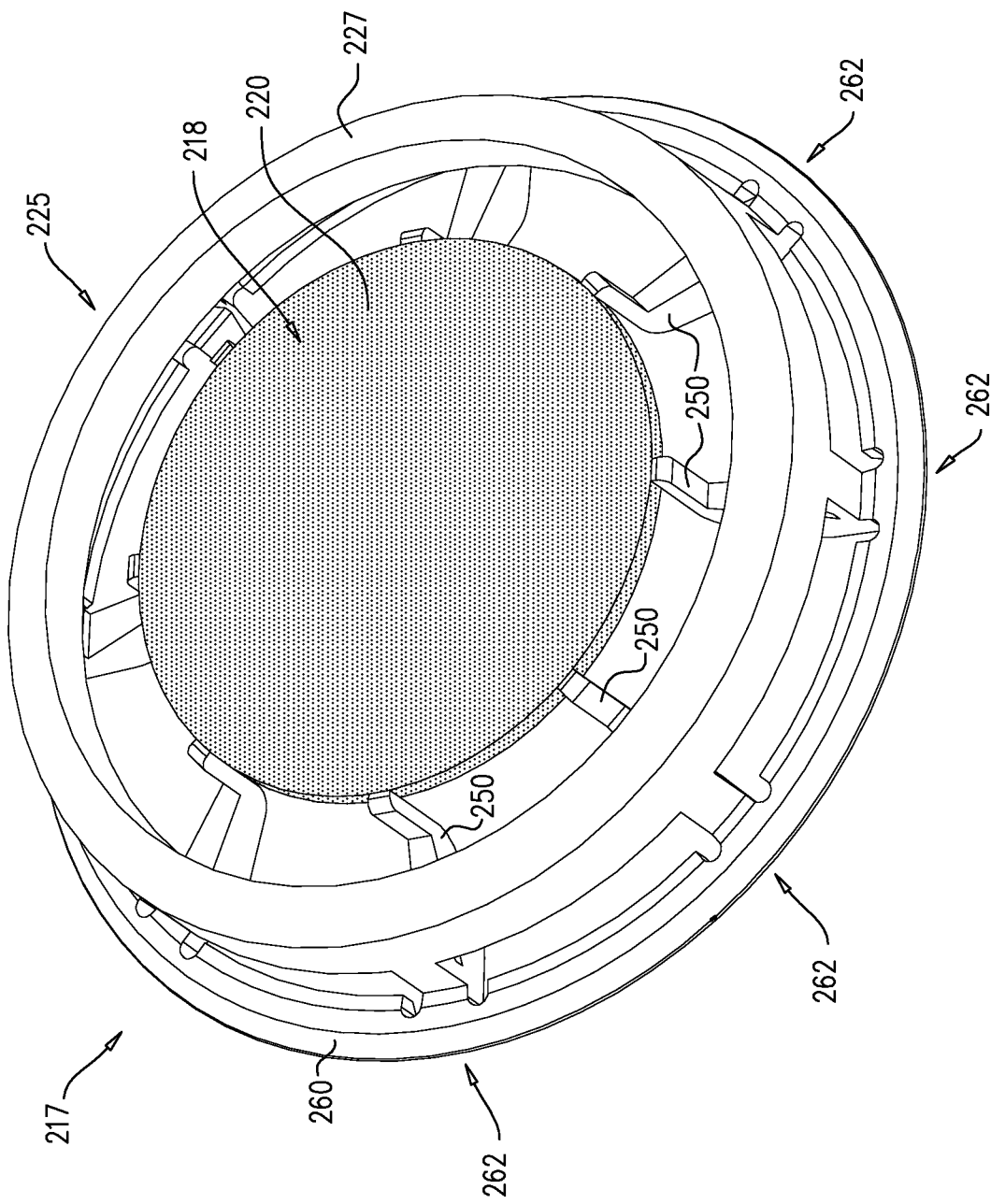
Figure 21B:
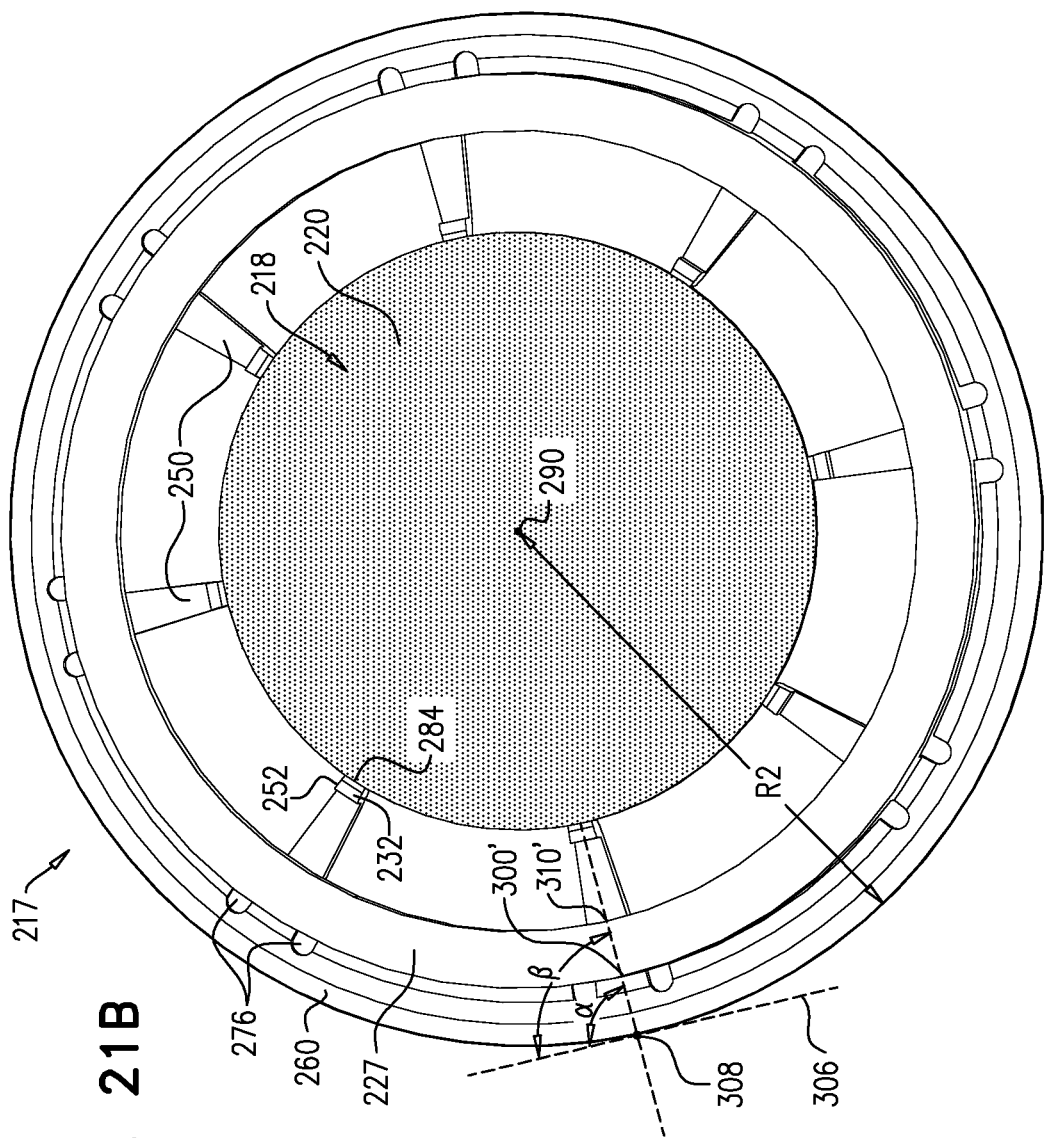

Reference is made to FIGS. 20D and 21B. For some applications, circumferential rim 260 has an outer radius R2 (labeled in FIG. 21B) that is greater than or equal to the local maximum radius R1 of inner surface 270 of posterior lens unit 222, such as between 100% and 105% of the local maximum radius R1.

Reference is made to FIGS. 19A-B and 20D. For some applications, lens implant 210 is shaped such that inner surface 270 limits posterior motion of anterior floating lens unit 218. For some applications, levers 250 and inner surface 270 of posterior lens unit 222 are shaped such that inner surface 270 limits the posterior motion of anterior floating lens unit 218 by inner surface 270 touching levers 250, such as shown in FIG. 19A.

Reference is made to FIGS. 21A-C, which are schematic illustrations of anterior component 217 of lens implant 210 in the fully-accommodated state, in accordance with an application of the present invention. FIG. 21A is an isometric view, FIG. 21B is a cross-sectional view, and FIG. 21C is viewed from the anterior direction. For some applications, circumferential rim 260 is shaped so as to define pairs of notches 276 on both circumferential sides of each of levers 250 at the site at which the lever is attached to the circumferential rim. These notches allow the levers to rotate about the respective joints with posterior lens unit 222, thereby obviating any need for the entire circumferential rim to rotate. Alternatively, circumferential rim 260 is not shaped so as to define notches 276.

Figure 22A:
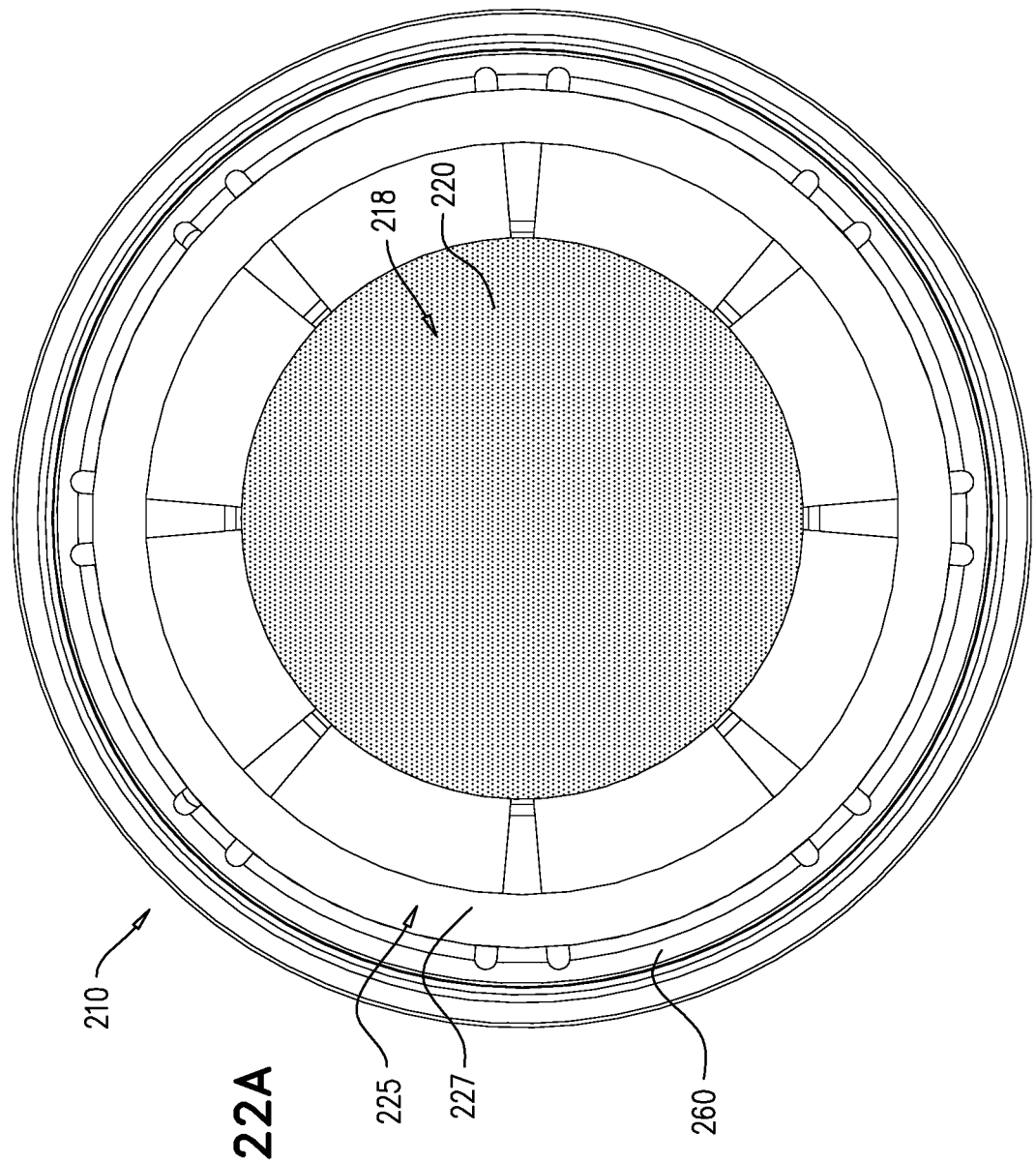
FIGS. 22A-C are schematic illustrations of the lens implant of FIGS. 16A-B in the fully-accommodated state, in accordance with an application of the present invention.
Figure 22B:
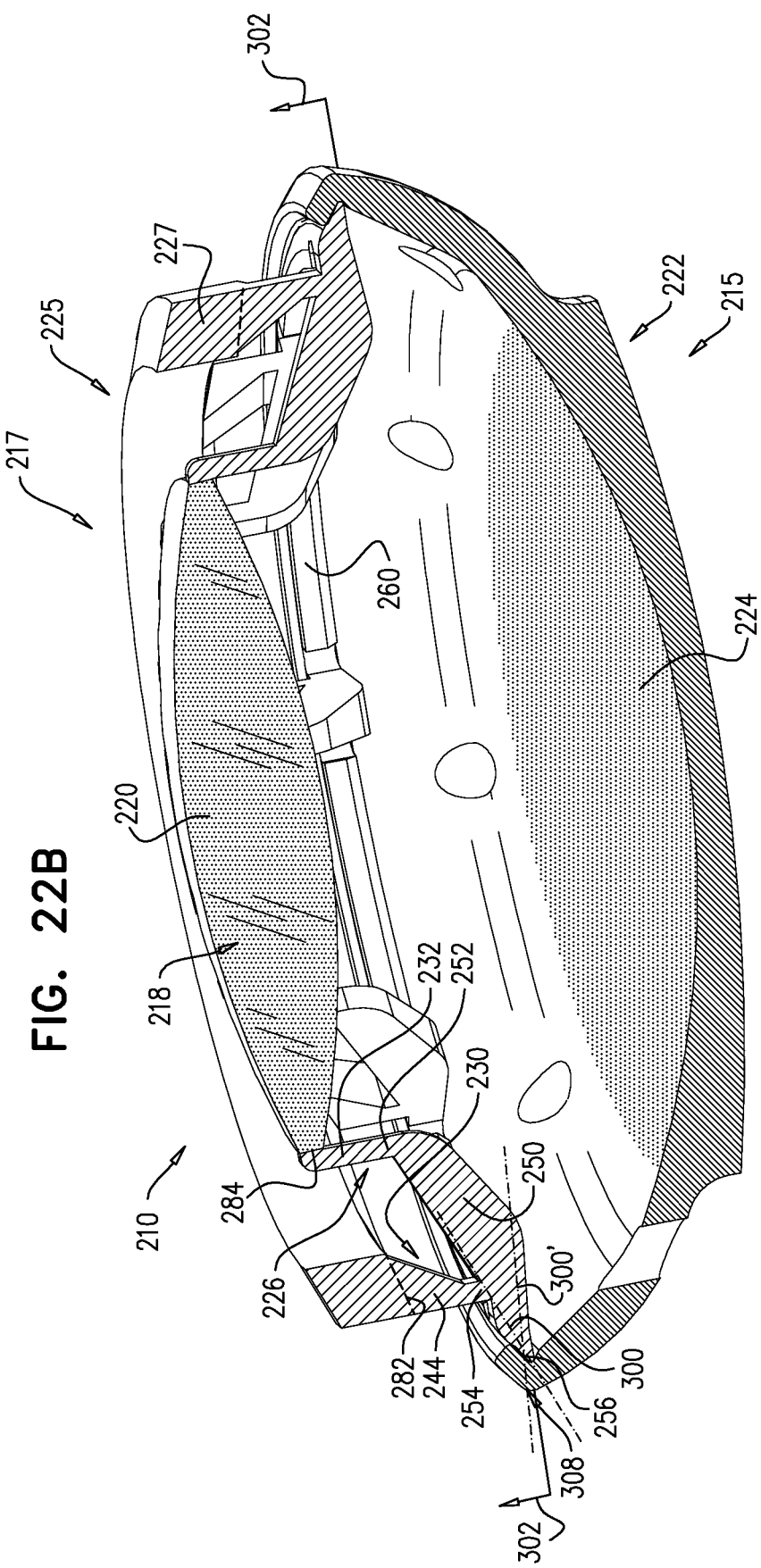
Figure 22C:
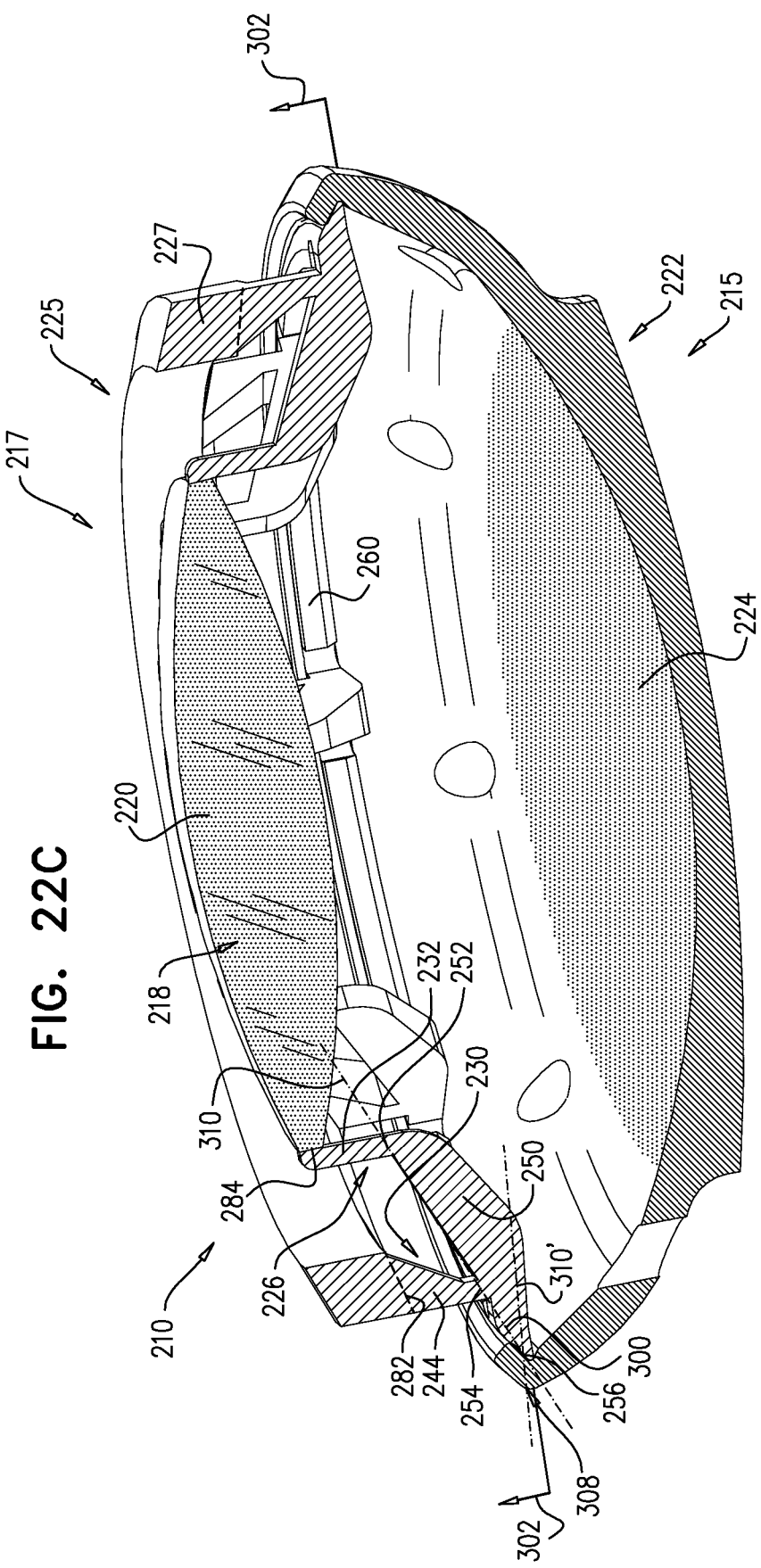

Reference is made to FIGS. 22A-C, which are schematic illustrations of lens implant 210 in the fully-accommodated state, in accordance with an application of the present invention. FIG. 22A shows lens implant 210 from the anterior direction, and FIGS. 22B-C are cross-sectional views.

Reference is made to FIGS. 21B and 22B. For some applications, for each of levers 250, (a) a line 300 defined by second longitudinal site 254 of lever 250 and third longitudinal site 256 of lever 250, if projected onto a plane 302 defined by a radially-outer perimeter 304 of lens implant 210 (resulting in a line 300'), and (b) a line 306 tangential to radially-outer perimeter 304 of lens implant 210 at a circumferential site 308 of perimeter 304 circumferentially corresponding to third longitudinal site 256 of lever 250, form an angle α (alpha) of between 75 and 105 degrees, such as between 85 and 95 degrees, e.g., 90 degrees. For some applications, as shown in the figures, radially-outer perimeter 304 of lens implant 210 is defined by posterior lens unit 222.

For some applications, each of levers 250 would not be curved if it were to be projected onto plane 302 defined by radially-outer perimeter 304 of lens implant 210. Alternatively or additionally, for some applications, for each of levers 250, first, second, and third longitudinal sites 252, 254, and 256 would lie along a single line if projected onto plane 302 defined by radially-outer perimeter 304 of lens implant 210.

Reference is made to FIGS. 21B and 22C. Alternatively or additionally to the configurations described in the preceding two paragraphs, for some applications, for each of levers 250, (a) a line 310 defined by first longitudinal site 252 of lever 250 and third longitudinal site 256 of lever 250, and (b) line 306 tangential to radially-outer perimeter 304 of lens implant 210 at circumferential site 308 of perimeter 304 circumferentially corresponding to third longitudinal site 256 of lever 250, form an angle β (beta) of between 75 and 105 degrees, such as between 85 and 95 degrees, e.g., 90 degrees.

Reference is again made to FIG. 21C. For some applications, first straight line segment 300 between second longitudinal site 254 along lever 250 and third longitudinal site 256 (which serves as fulcrum 264) along lever 250 is horizontal at some point during the transition between the fully-accommodated and fully-unaccommodated states, inclusive of the endpoints of the transition (i.e., the fully-accommodated and fully-unaccommodated states themselves). In other words, first line segment 300 is parallel to a plane perpendicular to central optical axis 290 during the transition. Alternatively, first line segment 300 is nearly horizontal at some point during the transition (inclusive of the endpoints of the transition), e.g., defines an angle of less than 15 degrees, such as less than 5 degrees, with the plane perpendicular to central optical axis 290. For some applications, first line segment 300) rotates at least 10 degrees, no more than 35 degrees, and/or between 10 and 35 degrees, such as at least 18 degrees, no more than 28 degrees, and/or between 18 and 28 degrees, as lens implant 210 transitions between the fully-accommodated and fully-unaccommodated states, e.g., 24 degrees (i.e., during a full stroke of the lever). Alternatively or additionally, for some applications, at a midpoint of the rotation of first line segment 300, as lens implant 210 transitions between the fully-accommodated and fully-unaccommodated states (i.e., during a full stroke of the lever), first line segment 100 defines an angle of less than 15 degrees, such as less than 5 degrees, the plane perpendicular to central optical axis 290, e.g., is parallel to the plane.

Alternatively or additionally, for some applications, a second straight line segment 301 between second longitudinal site 254 along lever 250 and first longitudinal site 252 along lever 250 is horizontal at some point during the transition between the fully-accommodated and fully-unaccommodated states, inclusive of the endpoints of the transition (i.e., the fully-accommodated and fully-unaccommodated states themselves). In other words, second line segment 301 is parallel to a plane perpendicular to central optical axis 290 during the transition. Alternatively, second line segment 301 is nearly horizontal at some point during the transition (inclusive of the endpoints of the transition), e.g., defines an angle of less than 15 degrees, such as less than 5 degrees, degrees with the plane perpendicular to central optical axis 290. Alternatively or additionally, for some applications, at a midpoint of the rotation of second line segment 301, as lens implant 210 transitions between the fully-accommodated and fully-unaccommodated states (i.e., during a full stroke of the lever), second line segment 301 defines an angle of less than 15 degrees, such as less than 5 degrees, the plane perpendicular to central optical axis 290, e.g., is parallel to the plane.

Typically, an angle between first line segment 300 and second line segment 301 is greater than 120 degrees, such as greater than 150 degrees, e.g., 180 degrees (i.e., the line segments are collinear to each other). In other words, the functional portion of lever 250 is generally straight.

Typically, second longitudinal site 254 is closer to third longitudinal site 256 than to first longitudinal site 252. For some applications, a first distance D1 between second longitudinal site 254 and third longitudinal site 256 is less than 70% of a second distance D2 between first longitudinal site 252 and second longitudinal site 254; such a location of anterior rim link 230 along lever 250 typically provides a gain of at least 1.4. For some applications, first distance D1 is less than 30% of second distance D2, which typically provides a gain of at least 3.3. For some applications, first distance D1 is at least 500 microns. Typically, first distance D1 is at least 10%, typically at least 33%, of second distance D2. Typically, first longitudinal site 252 is near a first end of lever 250, such as within 10% of a total length of lever 250, measured along the central longitudinal axis of the lever, from the first end. Typically, third longitudinal site 256 at a second end of lever 250. (First and second distances D1 and D2 are the lengths of straight line segments 300 and 301, respectively.)

(It is to be understood that first and second straight line segments 300 and 301 are not physical components of lens implant 210, but rather geometric constructs used to describe certain properties of the implant.)

Reference is now made to FIGS. 23A-B, which provide an additional view of anterior component 217 of lens implant 210, in the fully-unaccommodated and the fully-accommodated states, respectively, in accordance with an application of the present invention.

In accordance with an application of the present invention, posterior lens unit 222 and anterior component 217 are preloaded into a single introducer tube, and separately introduced into the capsular bag from the single introducer. Posterior lens unit 222 and anterior component 217 are removably disposed in the introducer tube, and a distal-most portion of anterior component 217 is proximal to a proximal-most portion of posterior lens unit 222.

In accordance with an application of the present invention, a two-introducer tube delivery system is provided, which comprises:
    a first introducer tube, in which posterior lens unit 222 is removably disposed; and
    a second introducer tube, in which anterior component 217 is removably disposed.

The first and the second introducer tubes are distinct and separate from each other.

Figure 24:
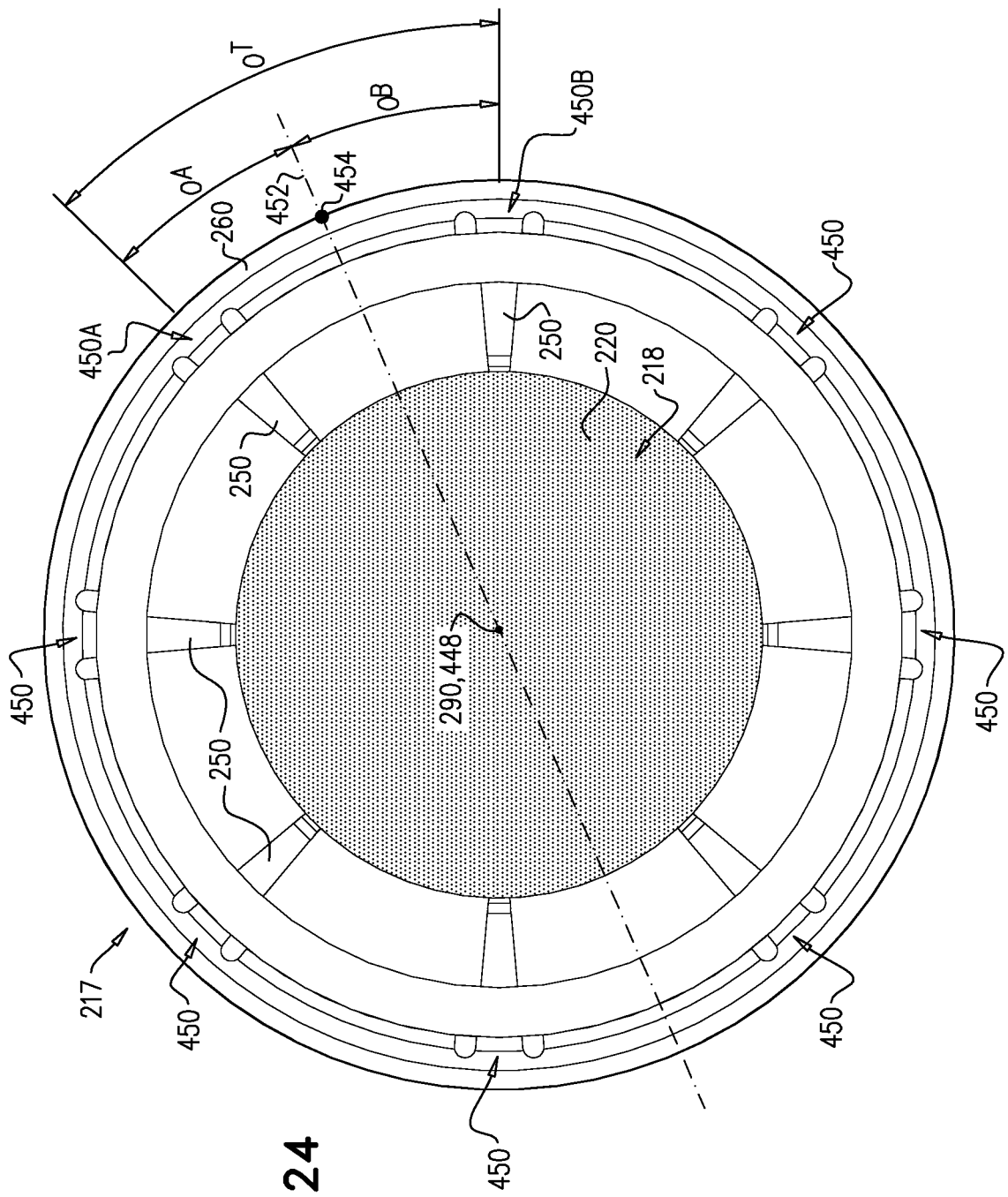
FIG. 24 is a schematic illustration of a technique for removably disposing an anterior component of the lens implant of FIGS. 16A-B in an introducer tube, in accordance with an application of the present invention.

Reference is now made to FIG. 24, which is a schematic illustration of a technique for removably disposing anterior component 217 of lens implant 210 in an introducer tube, in accordance with an application of the present invention. The introducer tube may comprise one of the introducer tubes described hereinabove. Anterior floating lens unit 218 has central optical axis 290 of anterior lens 220, which intersects a radial center 448 of anterior lens 220 and is perpendicular to a plane defined by circumferential rim 260 (and typically also defined by anterior lens 220). Levers 250 are fixed to circumferential rim 260 at respective circumferential sites 450, and (b) in jointed connection with anterior floating lens unit 218.

Anterior component 217 of lens implant 210 is removably disposed in the introducer tube while anterior component 217 is folded or rolled about a line 452 that:
    intersects (i) central optical axis 290 and (ii) a point 454 on circumferential rim 260 that is circumferentially between two circumferentially-adjacent ones 450A and 450B of circumferential sites 450, and
    is parallel to the plane defined by circumferential rim 260.
(Line 452 also intersects a second point on circumferential rim 260 at the opposite side of the ring.)

Typically, point 454 is circumferentially offset from each of the two circumferentially-adjacent circumferential sites 450A and 450B by at least 18 degrees (the circumferential offsets are labeled $O^A$ and $O^B$ in FIG. 24). Typically, point 454 is circumferentially offset from each of the two circumferentially-adjacent circumferential sites 450A and 450B by 40% to 60% of a circumferential offset $O^T$ between the two circumferentially-adjacent circumferential sites 450A and 450B (i.e., $O^A$ equals between 40% and 60%/n of $O^T$, and $O^B$ equals between 40% and 60% of $O^T$).

Reference is now made to FIGS. 16A-24. For some applications, as shown in the figures, lens implant 210 does not comprise any haptics.

Figure 25:
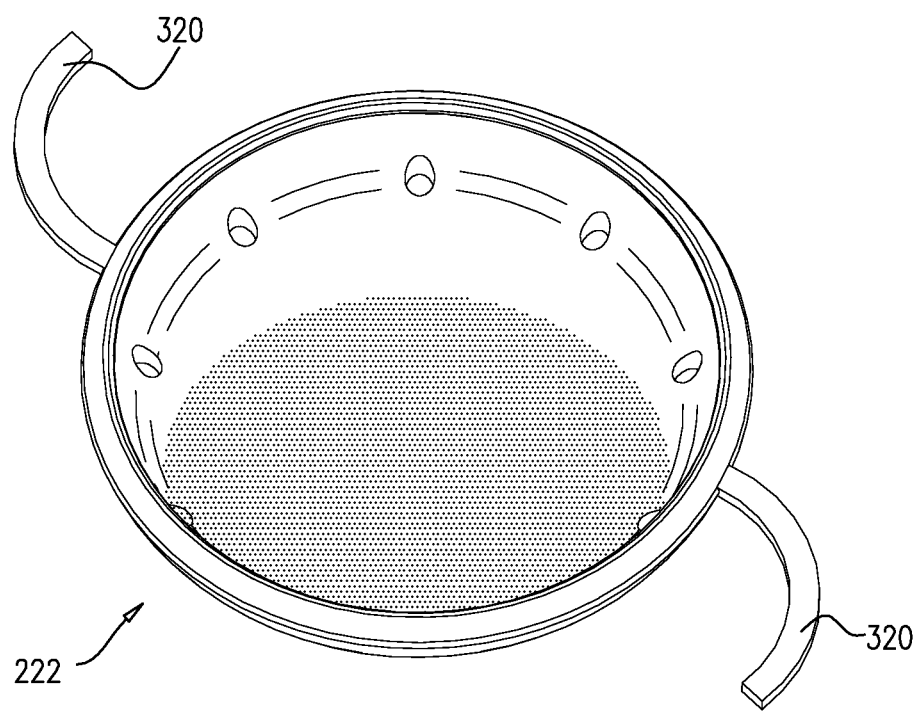
FIG. 25 is a schematic illustration of another configuration of the lens implant of FIGS. 16A-B, in accordance with an application of the present invention.

Reference is now made to FIG. 25, which is a schematic illustration of another configuration of lens implant 210, in accordance with an application of the present invention. In this configuration, lens implant 210 (e.g., posterior lens unit 222) comprises haptics 320, which are not configured to transmit motion to levers 250 (configuration not shown). For some of these latter applications, levers 250 are indirectly connected to the haptics by one or more other elements of lens implant 210.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. An apparatus comprising an accommodating intraocular lens implant, which comprises:
    an anterior floating lens unit, which comprises an anterior lens;
    a posterior lens unit, which is not itself jointed, and which comprises a posterior lens;
    an anterior rim complex disposed such that the anterior floating lens unit is movable toward and away from the anterior rim complex, in an anterior-posterior direction; and
    a plurality of levers, which are in jointed connection with:
        the anterior floating lens unit at respective first longitudinal sites along the plurality of levers,
        the anterior rim complex at respective second longitudinal sites along the plurality of levers, and
        the posterior lens unit at respective third longitudinal sites along the plurality of levers, such that the respective third longitudinal sites directly contact the posterior lens unit,
    wherein the respective second longitudinal sites are longitudinally between the respective first and the respective third longitudinal sites,
    wherein the third longitudinal sites are at greater distances from a central optical axis of the anterior lens than the second longitudinal sites are from the central optical axis, respectively, the distances measured perpendicular to the central optical axis, and wherein the levers are arranged (a) such that the third longitudinal sites serve as respective fulcrums for the plurality of levers, and (b) to move the anterior floating lens unit toward and away from the anterior rim complex, in the anterior-posterior direction.

2. The apparatus according to claim 1, wherein the accommodating intraocular lens implant further comprises anterior lens links, which comprise respective anterior lens jointed elements, and wherein the plurality of levers are in the jointed connection at the respective first longitudinal sites along the plurality of levers with the anterior floating lens unit by the respective anterior lens links.

3. The apparatus according to claim 1, wherein for each respective lever of the plurality of levers, an angle of between 75 and 105 degrees is formed by:

(a) a projection of a first line onto a plane defined by a radially-outer perimeter of the accommodating intraocular lens implant, the first line defined by the second longitudinal site of the respective lever and the third longitudinal site of the respective lever, and (b) a second line that is in the plane and that is tangential to the radially-outer perimeter of the accommodating intraocular lens implant at a circumferential site of the perimeter circumferentially corresponding to the third longitudinal site of the respective lever.

4. The apparatus according to claim 1, wherein for each respective lever of the plurality of levers, an angle of between 75 and 105 degrees is formed by:

(a) a projection of a first line onto a plane defined by a radially-outer perimeter of the accommodating intraocular lens implant, the first line defined by the first longitudinal site of the respective lever and the third longitudinal site of the respective lever, and (b) a second line that is in the plane and that is tangential to the radially-outer perimeter of the accommodating intraocular lens implant at a circumferential site of the perimeter circumferentially corresponding to the third longitudinal site of the respective lever.

5. The apparatus according to claim 1, wherein the accommodating intraocular lens implant comprises an anterior component, which comprises the anterior floating lens unit, the anterior rim complex, and the plurality of levers, wherein the posterior lens unit and the anterior component are distinct from each other and not permanently fixed to each other, and which are shaped so as to be assemblable together in situ in a human eye, and wherein when the posterior lens unit and the anterior component are assembled together, the posterior lens unit and the anterior component contact each other at one or more interfaces.

6. The apparatus according to claim 5, wherein when the posterior lens unit and the anterior component are assembled together, the plurality of levers are pivotable about one of the one or more interfaces, respectively.

7. The apparatus according to claim 1, wherein the plurality of levers comprises six levers.

8. The apparatus according to claim 1, wherein the plurality of levers comprises more than six levers.

9. The apparatus according to claim 1, wherein the accommodating intraocular lens implant comprises a circumferential rim, wherein the plurality of levers, at the respective third longitudinal sites along the plurality of levers, are (i) fixed to the circumferential rim at respective, different circumferential locations around the circumferential rim, and (ii) in jointed connection with the posterior lens unit.

10. The apparatus according to claim 1, wherein the third longitudinal sites are at respective end-most sites of the plurality of levers.

11. The apparatus according to claim 1, wherein respective straight line segments between the second longitudinal sites and the third longitudinal sites define respective angles of less than 15 degrees with a plane perpendicular to the central optical axis of the anterior lens at some point during a transition between fully-accommodated and fully-unaccommodated states of the accommodating intraocular lens implant.

12. The apparatus according to claim 1, wherein for each respective lever of the plurality of levers, the first, the second, and the third longitudinal sites lie along a single straight line when projected onto a plane defined by a radially-outer perimeter of the accommodating intraocular lens implant.

* * * * *